US009315583B2

(12) United States Patent
Fischer et al.

(10) Patent No.: US 9,315,583 B2
(45) Date of Patent: Apr. 19, 2016

(54) ASSAYS FOR DETECTING ANTIBODIES SPECIFIC TO THERAPEUTIC ANTI-IGE ANTIBODIES AND THEIR USE IN ANAPHYLAXIS

(75) Inventors: Saloumeh Fischer, Castro Valley, CA (US); Dana L. Baker, Half Moon Bay, CA (US); Henry B. Lowman, El Granada, CA (US); Gerald R. Nakamura, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 222 days.

(21) Appl. No.: 12/912,657

(22) Filed: Oct. 26, 2010

(65) Prior Publication Data

US 2011/0183363 A1 Jul. 28, 2011

Related U.S. Application Data

(60) Provisional application No. 61/255,052, filed on Oct. 26, 2009.

(51) Int. Cl.
*C07K 16/42* (2006.01)
*G01N 33/68* (2006.01)
*G01N 33/543* (2006.01)
*G01N 33/564* (2006.01)

(52) U.S. Cl.
CPC ......... *C07K 16/4291* (2013.01); *C07K 16/4208* (2013.01); *C07K 16/4241* (2013.01); *C07K 16/4283* (2013.01); *G01N 33/543* (2013.01); *G01N 33/564* (2013.01); *G01N 33/686* (2013.01); *G01N 33/6854* (2013.01); *C07K 2317/24* (2013.01); *C07K 2317/565* (2013.01); *C07K 2317/76* (2013.01); *G01N 2800/24* (2013.01)

(58) Field of Classification Search
CPC ........... C07K 16/4208; C07K 16/4241; C07K 16/4283; C07K 16/4291; C07K 2317/24; C07K 2317/565; C07K 2317/76; G01N 33/543; G01N 33/564; G01N 33/6854; G01N 33/686; G01N 2800/24
USPC ........ 435/7.1, 7.21, 7.24, 7.5, 7.8, 7.92, 7.94, 435/7.95, 69.3, 69.7, 975; 436/501, 513, 436/518, 536, 547; 530/387.3, 388.1, 530/388.25, 389.3, 391.1, 391.5, 413, 862, 530/867, 868
See application file for complete search history.

(56) References Cited

U.S. PATENT DOCUMENTS

| 3,645,090 A | 2/1972 | Mochizuki et al. |
| 3,645,852 A | 2/1972 | Axen et al. |
| 3,691,016 A | 9/1972 | Patel et al. |
| 3,720,760 A | 3/1973 | H:son et al. |
| 3,940,475 A | 2/1976 | Gross |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,376,110 A | 3/1983 | David et al. |
| 4,459,359 A * | 7/1984 | Neurath ............................. 435/5 |
| 4,518,584 A | 5/1985 | Mark et al. |
| 4,683,136 A * | 7/1987 | Milich et al. ............... 424/189.1 |
| 4,737,456 A | 4/1988 | Weng et al. |
| 4,737,462 A | 4/1988 | Mark et al. |
| 4,816,567 A | 3/1989 | Cabilly et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,661,016 A | 8/1997 | Lonberg et al. |
| 6,172,213 B1 | 1/2001 | Lowman et al. |
| 6,537,745 B2 * | 3/2003 | Chien et al. ........................ 435/5 |
| 6,875,432 B2 | 4/2005 | Liu et al. |
| 7,897,153 B1 * | 3/2011 | Braren et al. .............. 424/192.1 |
| 2004/0197324 A1 | 10/2004 | Liu et al. |
| 2005/0158303 A1 | 7/2005 | Liu et al. |
| 2007/0184501 A1 * | 8/2007 | Odegaard ..................... 435/7.92 |

FOREIGN PATENT DOCUMENTS

| CN | 101052653 A | 10/2007 |
| WO | WO-91/10741 A1 | 7/1991 |
| WO | WO-92/17207 A1 | 10/1992 |
| WO | WO-96/33735 A1 | 10/1996 |
| WO | WO-96/34096 A1 | 10/1996 |
| WO | WO-97/17852 A1 | 5/1997 |

(Continued)

OTHER PUBLICATIONS

Calogiuri et al., 2008. Hypersensitivity reactions to last generation chimeric, umanized and human recombinant monoclonal antibodies for therapeutic use. Curr. Pharm. Design 14: 2883-2891.*
Price et al., 2007. Anaphylactoid reactions in two patients after omalizumab administration after successful long-term therapy. Allergy Asthma Proc. 28: 313-319.*
Shankar et al., 2006. Scientific and regulatory considerations on the immunogenicity of biologics. Trends in Biotechnol. 24: 274-280.*
Stedman et al., 2001. Measurement of canine IgE using the alpha chain of the human high affinity IgE receptor. Vet. Immunol. Immunopathol. 78: 349-355.*
Bauer, C.E. et al. (1985). "A Genetic Enrichment for Mutations Constructed by Oligodeoxynucleotide-Directed Mutagenesis," *Gene* 37:73-81.
Brüggemann, M. et al. (1993). "Designer Mice: The Production of Human Antibody Repertoires in Transgenic Animals," *Year in Immunol.* 7:33-40.

(Continued)

*Primary Examiner* — Gail R Gabel
*Assistant Examiner* — James L Grun
(74) *Attorney, Agent, or Firm* — Morrison & Foerster LLP

(57) ABSTRACT

The invention provides methods and reagents useful for detecting anti-drug antibodies of IgE isotype to therapeutic anti-IgE antibodies, and methods for assessing risk of anaphylaxis to administration of a therapeutic anti-IgE antibody.

40 Claims, 23 Drawing Sheets

(56) References Cited

FOREIGN PATENT DOCUMENTS

| WO | WO-98/24893 | A2 | 6/1998 |
|----|----|----|----|
| WO | WO-98/24893 | A3 | 6/1998 |
| WO | WO 99/01556 | A2 | 1/1999 |
| WO | WO 99/01556 | A3 | 1/1999 |
| WO | WO-2004/070010 | A2 | 8/2004 |
| WO | WO-2004/070010 | A3 | 8/2004 |
| WO | WO-2004/070011 | A2 | 8/2004 |
| WO | WO-2004/070011 | A3 | 8/2004 |
| WO | WO-2006/028956 | A2 | 3/2006 |
| WO | WO-2006/028956 | A3 | 3/2006 |
| WO | WO-2006/028956 | A9 | 3/2006 |
| WO | WO-2008/028068 | A2 | 6/2008 |
| WO | WO-2008/028068 | A3 | 6/2008 |
| WO | WO-2008/028068 | A8 | 6/2008 |

OTHER PUBLICATIONS

Capel, P.J.A. et al. (1994). "Heterogeneity of Human IgG FC Receptors," *Immunomethods* 4: 25-34.

Casale, T.B. et al. (1997). "Use of an Anti-IgE Humanized Monoclonal Antibody in Ragweed-Induced Allergic Rhinitis," *Journal of Allergy and Clinical Immunology* 100(1):110-121.

Chen, Y. et al. (1999). "Selection and Analysis of an Optimized Anti-VEGF Antibody: Crystal Structure of an Affinity-Matured Fab in Complex with Antigen," *J. Mol. Biol.* 293:865-881.

Chothia, C. et al. (1987). "Canonical Structures for the Hypervariable Regions of Immunoglobulins," *J. Mol. Biol.* 196:901-917.

Clackson, T. et al. (Aug. 15, 1991). "Making Antibody Fragments Using Phage Display Libraries," *Nature* 352:624-628.

Corne, J. et al. (Mar. 1997). "The Effect of Intravenous Administration of a Chimeric Anti-IgE Antibody on Serum IgE Levels in Atopic Subjects: Efficacy, Safety, and Pharmacokinetics," *J. Clin. Invest.* 99(5):879-887.

Craik, C.S. (Jan. 1985). "Use of Oligonucleotides for Site-Specific Mutagenesis," *Bio Techniques* 3(2)12-19.

David, G.S. et al. (Feb. 26, 1974). "Protein Iodination with Solid State Lactoperoxidase," *Biochemistry*, 13(5):1014-1021.

De Haas, M. et al. (Oct. 1995.) "Fcγ Receptors of Phagocytes," *J. Lab. Clin. Med.* 126: 330-341.

Engvall, E. et al. (Sep. 1971). "Enzyme-linked Immunosorbent Assay (ELISA). Quantitative Assay of Immunoglobulin G," *Immunochemistry* 8(9):871-874.

Fellouse, F.A. et al (Aug. 24, 2004). "Synthetic Antibodies from a Four-Amino-acid Code: A Dominant Role for Tyrosine in Antigen Recognition," *Proc. Nat. Acad. Sci. USA* 101(34):12467-12472.

Fishwild, D.M. et al. (Jul. 1996). "High-avidity Human IgG Kappa Monoclonal Antibodies from a Novel Strain of Minilocus Transgenic Mice," *Nature Biotechnology* 14:845-851.

Hamers-Casterman, C. et al. (Jun. 3, 1993). "Naturally Occurring Antibodies Devoid of Light Chains," *Nature* 363:446-448.

Hammerling, G.J. et al. (1981). *Monoclonal Antibodies and T-Cell Hybridomas*, Elsevier, New York, New York, pp. 563-587.

Hunter, W.M. et al. (May 5, 1962). "Preparation of Iodine-131 Labelled Human Growth Hormone of High Specific Activity," *Nature* 144:495-496.

International Search Report mailed on Jan. 19, 2011, for PCT Application No. PCT/US2010/054160, filed on Oct. 26, 2010, three pages.

Jakobovits, A. et al. (Mar. 15, 1993). "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90:2551-2555.

Jakobovits, A. et al. (Mar. 18, 1993). "Germ-line Transmission and Expression of a Human-Derived Yeast Artificial Chromosome," *Nature* 362:255-258.

Johnson, G. et al. (2003). Chapter 2 in *Methods in Molecular Biology*, Human Press, Lo.vol. 248, Lo, B,K.C. ed., Human Press, Totowa, New Jersey, pp. 11-25.

Jones, P.T. et al. (May 29-Jun. 4, 1986). "Replacing the Complementarity-Determining Regions in a Human Antibody with Those from a Mouse," *Nature* 321:522-525.

Kinet, J.P. (1999). "The High-Affinity IgE Receptor (FC Epsilon RI): From Physiology to Pathology," *Annu. Rev. Immunol.* 17:931-972.

Kohler, G. et al. (Aug. 7, 1975). "Continuous Cultures of Fused Cells Secreting Antibody of Predefined Specificity," *Nature* 256:495-497.

Lee, C.V. et al. (Jan. 2004). "Bivalent Antibody Phage Display Mimics Natural Immunoglobulin," *J. Immunol. Methods* 284(1-2):119-132.

Lee, C.V. et al.(Jul. 23, 2004). "High-Affinity Human Antibodies From Phage-Displayed Synthetic Fab Libraries With a Single Framework Scaffold," *J. Mol. Biol.* 340(5):1073-1093.

Lonberg, N. et al. (Apr. 28, 1994) "Antigen-Specific Human Antibodies from Mice Comprising Four Distinct Genetic Modifications," *Nature* 368: 856-859.

Lonberg, N. et al. (1995). "Human Antibodies from Transgenic Mice," *Intern. Rev. Immunol.*, 13: 65-93.

Marks, J.D. et al. (Dec. 5, 1991). "By-Passing Immunization. Human Antibodies from V-gene Libraries Displayed on Phage," *J. Mol. Biol.* 222:581-597.

Marks, J.D et al. (Jul. 1992). "By-passing Immunization: Building High Affinity Human Antibodies by Chain Shuffling," *Bio/Technology*, 10:779-783.

Morrison, S.L. (Apr. 28, 1994). "Immunology. Success in specification," *Nature* 368: 812-813.

Morrison, S.L. (Nov. 1984). "Chimeric Human Antibody Molecules: Mouse Antigen-binding Domains with Human Constant region Domains," *Proc. Natl. Acad. Sci. USA* 81:6851-6855.

Neuberger, M. (Jul. 1996). "Generating High-avidity Human Mabs in Mice," *Nature Biotechnology* 14: 826.

Nygren, H. (May 1982). "Conjugation of Horseradish Peroxidase to Fab Fragments with Different Homobifunctional and Heterobifunctional Cross-linking Reagents. A Comparative Study," *J. Histochem and Cytochem.* 30:407-412.

O'Sullivan, M.J. et al. (1981). "Methods for the Preparation of Enzyme-antibody Conjugates for Use in Enzyme Immunoassay," Chapter 19, vol. 73 in *Methods in Enzymology*, Langone, J.J. et al., Academic Press, New York, N.Y., pp. 147-166.

Pain, D. et al. (1981). "Preparation of Protein A-peroxidase Monoconjugate Using a Heterobifunctional Reagent, and its Use in Enzyme Immunoassays," *J. Immunol Methods* 40:219-230.

Presta, L.G. et al. (Sep. 1, 1993). "Humanization of an Antibody Directed Against IgE," *J. Immunol.* 151(5):2623-2632.

Presta, L.G. et al. (Oct. 15, 1997). "Humanization of an Anti-vascular Endothelial Growth Factor Monoclonal Antibody for the Therapy of Solid Tumors and Other Disorders," *Cancer Res.* 57:4593-4599.

Presta, L.G. (1992). "Antibody Engineering," *Curr. Op. Struct. Biol.* 2:593-596.

Ravetch, J.V. et al. (1991). "Fc Receptors," *Annu. Rev. Immunol.* 9:457-492.

Reichmann, L. et al.(Mar. 24, 1988). "Reshaping Human Antibodies for Therapy," *Nature* 332:323-327.

Rotmans, J. P. et al. (Feb. 25, 1983). "Cross-linking of *Schistosoma mansoni* Antigens and Their Covalent Binding on the Surface of Polystyrene Microtitration Trays for Use in the ELISA," *J. Immunol. Methods* 57:87-98.

Sheriff, S. et al. (Sep. 1996). "Redefining the Minimal Antigen-binding Fragment," *Nature Struct. Biol.* 3:733-736.

Sidhu, S.S. et al. (Apr. 23, 2004). "Phage-displayed Antibody Libraries of Synthetic Heavy Chain Complementarity Determining Regions," *J. Mol. Biol.* 338(2):299-310.

Xu, J.L. et al. (Jul. 2000). "Diversity in the CDR3 Region of $V_H$ is Sufficient for Most Antibody Specificities," *Immunity* 13:37-45.

Walder, R.Y. et al. (1986). "Oligodeoxynucleotide-directed Mutagenesis Using the Yeast Transformation System," *Gene* 42:133.

Written Opinion mailed on Jan. 19, 2011, for PCT Application No. PCT/US2010/054160, filed on Oct. 26, 2010, four pages.

Fahy et al. "Effect of Aerosolized Anti-IgE (E25) on Airway Response to Inhaled Allergen in Asthmatic Subjects," *Am. J. Respir. Crit. Care Med.* 160:1023-1027, (1999).

Hamilton et al., "Immunological methods for quantifying free and total serum IgE levels in allergy patients receiving Omalizumab (Xolair) therapy," *Journal of Immunological Methods* 303:83-84, (Aug. 2005).

(56) References Cited

OTHER PUBLICATIONS

Pakula et al., "Genetic analysis of protein stability and function," *Annu. Rev. Genet.* (1989).
Rudikoff et al., "Single amino acid substitution altering antigen-binding specificity," *Proc. Nat. Acad. Sci. USA* 79:1979-1983, (Mar. 1982).
Brown, M. et al. "Tolerance of single, but not multiple, amino acid replacements in antibody $V_H$ CDR 2: a means of minimizing B cell wastage from somatic hypermutation?" *The Journal of Immunology* 156: 3285-91, (1996).
Ohno et al. "Antigen-binding specificities of antibodies are primarily determined by seven residues of $V_H$," *Proc. Natl. Acad. Sci. USA* 82:2945-2949, (May 1985).
Severin et al. "Biochemistry," textbook, M: Moscow, 2000, p. 7. (Russian) (English Translation of lines 6-8, p. 7).

\* cited by examiner

E25 light chain (V$_L$ and C$_L$ domains)

```
         10         20         30         40         50         60         70         80
DIQLTQSPSS LSASVGDRVT ITC[RASQSVD YDGDSYMN]WY QQKPGKAPKL LIY[AASYLES] GVPSRFSGSG SGTDFTLTIS
         90        100        110              C_L starts
SLQPEDFATY YC[QQSHEDPY T]FGQGTKVEI KRT VAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC
```

Figure 1A

E25 heavy chain (V$_H$ and C$_H$ domains)

```
         10         20         30         40       50 a         60         70         80         90
EVQLVESGGG LVQPGGSLRL SCAVSGYSIT S[GYSWNW]IRQ APGKGLEWVA [SITYDGSTNY NPSVKG]RITI SRDDSKNTFY LQMNSLRAED
        100        110ab      120 C_H starts
TAVYYCAR[GS HYFGHWHFAV] WGQGTLVTVSS ASTKGPSVFPLAPSSKSTSGGTAALGCLVKDYFPEPVTVSWNSGALTSGVHTFPAVLQSSGLYSLSS VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPGK
```

Figure 1B

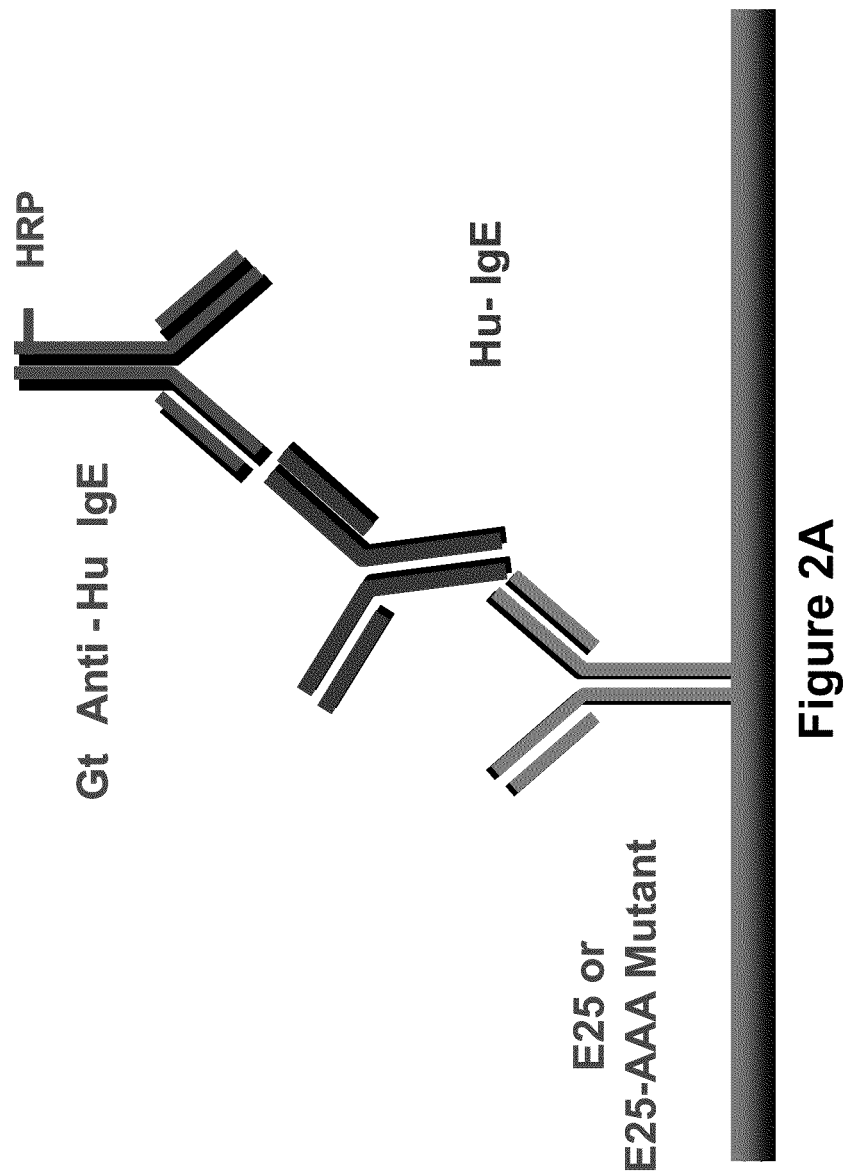

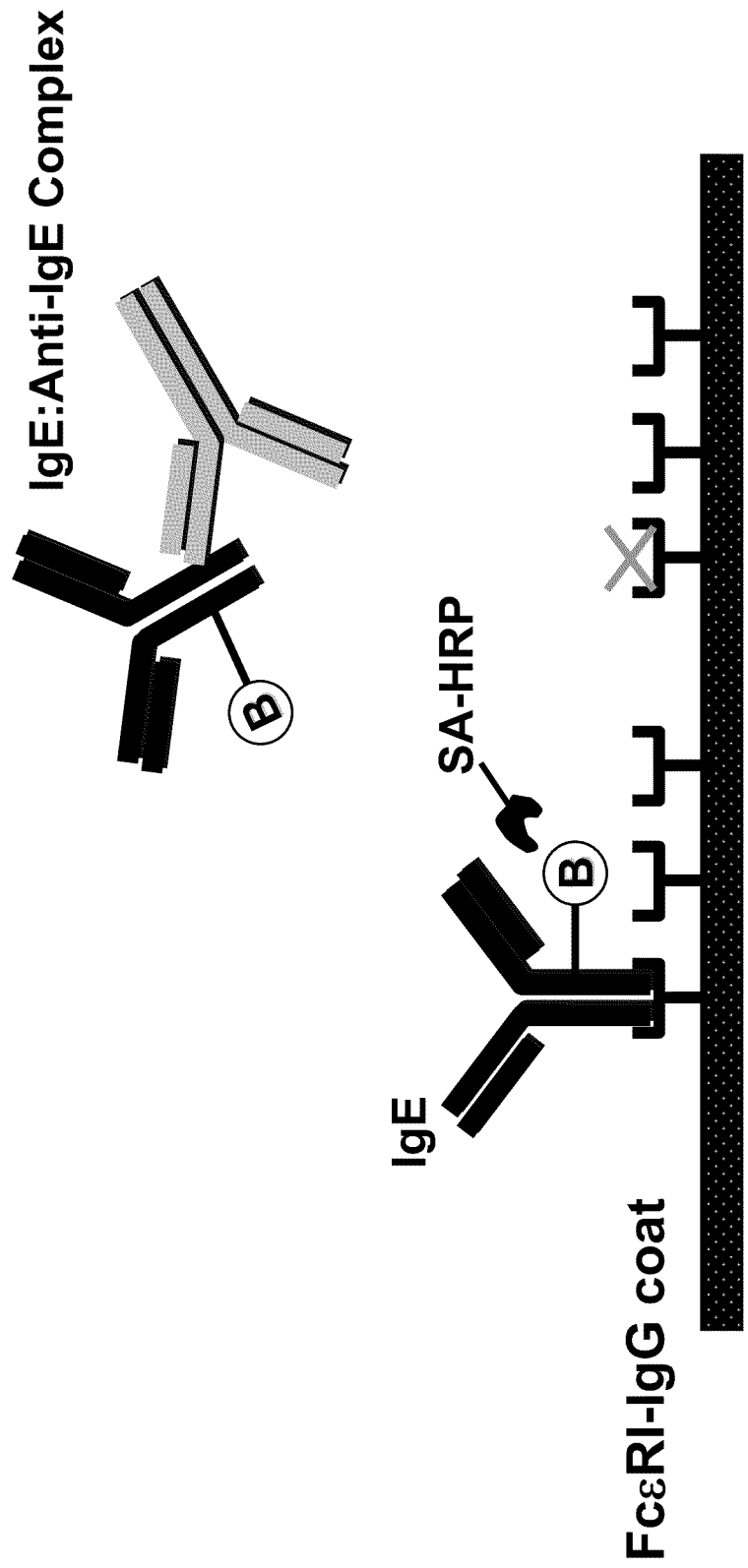

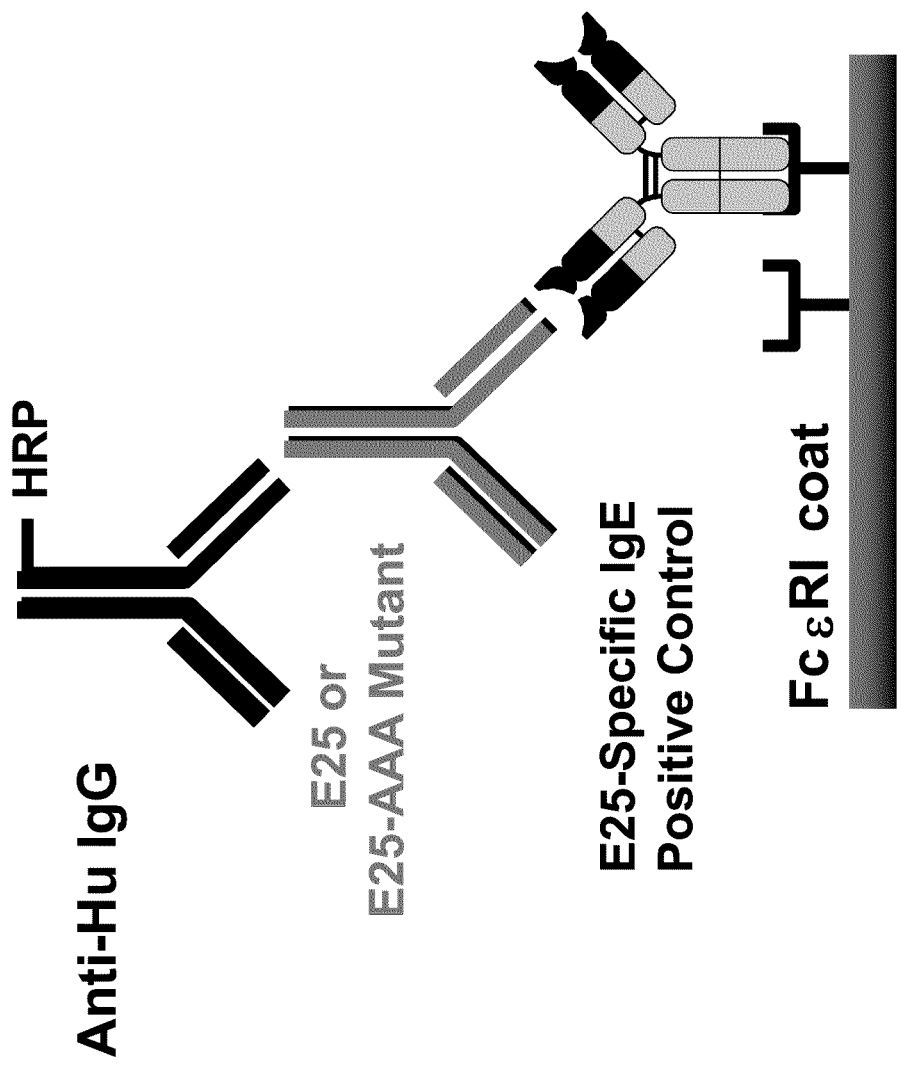

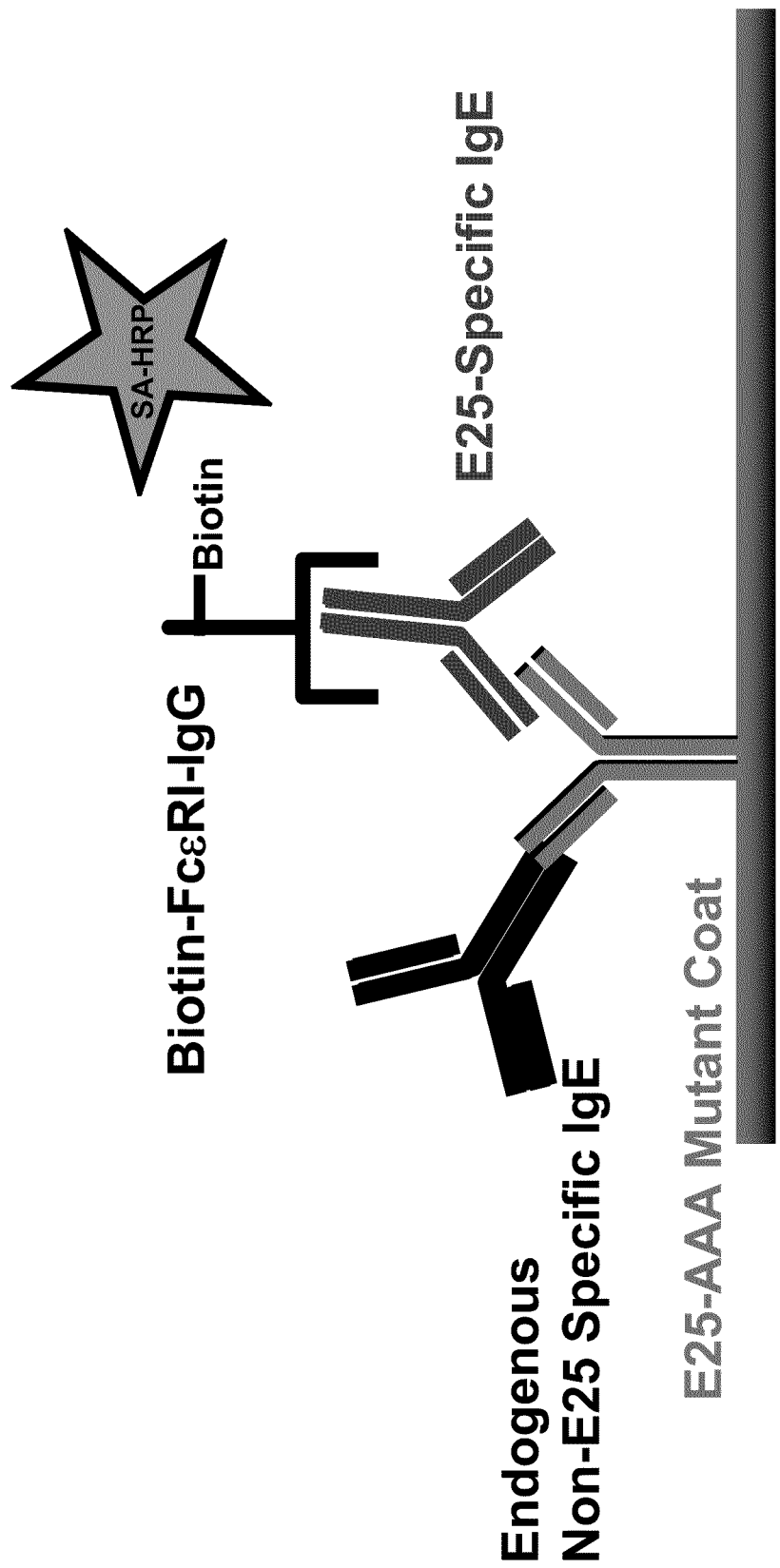

ASSAYS FOR DETECTING ANTIBODIES SPECIFIC TO THERAPEUTIC ANTI-IGE ANTIBODIES AND THEIR USE IN ANAPHYLAXIS

CROSS-REFERENCE TO RELATED APPLICATIONS

This application claims the priority benefit of U.S. provisional application Ser. No. 61/255,052, filed Oct. 26, 2009, which is incorporated herein by reference in its entirety.

TECHNICAL FIELD

The present invention relates generally to the fields of methods and reagents for detecting anti-drug antibodies of IgE isotype to therapeutic anti-IgE antibodies, and methods for assessing risk of anaphylaxis.

BACKGROUND

IgE is a member of the immunoglobulin family that mediates allergic responses such as asthma, food allergies, type I hypersensitivity and the familiar sinus inflammation suffered on a widespread basis. IgE is secreted by, and expressed on the surface of B-cells or B-lymphocytes. IgE binds to B-cells (as well as to monocytes, eosinophils and platelets) through its Fc region to a low affinity IgE receptor, known as FcεRII. Upon exposure of a mammal to an allergen, B-cells bearing a surface-bound IgE antibody specific for the antigen are "activated" and developed into IgE-secreting plasma cells. The resulting allergen-specific IgE then circulates through the bloodstream and becomes bound to the surface of mast cells in tissues and basophils in the blood, through the high affinity receptor also known as FcεRI. The mast cells and basophils thereby become sensitized for the allergen. Subsequent exposure to the allergen causes a cross linking of the basophilic and mast cellular FcεRI which results in degranulation of these cells and a release of histamine, leukotrienes and platelet activating factors, eosinophil and neutrophil chemotactic factors and the cytokines IL-3, IL-4, IL-5 and GM-CSF which are responsible for clinical hypersensitivity and anaphylaxis.

Antagonists that block IgE-Receptor complex formation are useful as therapeutic agents to prevent allergic response. Several therapeutic anti-IgE antibodies have been developed. These anti-IgE antibodies block IgE from binding to the high-affinity receptor FcεRI found on basophils and mast cells, and thereby prevent the release of histamine and other anaphylactic factors resulting in the pathological condition.

Anaphylaxis has been reported to occur in patients after receiving anti-IgE antibodies, such as omalizumab (e.g., Xolair®). Anaphylaxis is an acute systemic (multi-system) and very severe type I hypersensitivity allergic reaction. It is caused by degranulation of mast cells and basophils and mediated by IgE. Through 2006, 124 of 57,269 (about 0.2%) asthma patients had anaphylaxis after omalizumab administration. While there are no reports of fatal anaphylaxis as a result of omalizumab, some cases have been serious, and potentially life-threatening. For this reason, the FDA recommends that patients receiving omalizumab be monitored in the physician's office for a period of time after omalizumab administration, and health care providers administering omalizumab should be prepared to manage anaphylaxis that can be life-threatening. Sixty percent of the cases reported (124) has been after the first two doses of omalizumab. Therefore, it is possible that the reaction is from pre-existing antibodies in patients that recognize an epitope on omalizumab, as opposed to an anti-drug reaction that develops after drug administration. As anaphylaxis is associated with antibody of the IgE isotype, there is a need to develop an assay for detecting and quantitating the amount of IgE in a patient that is specific to the therapeutic anti-IgE antibody to assess the risk of anaphylaxis preferably before such anti-IgE antibody treatment and identify high risk patients.

All references cited herein, including patent applications and publications, are incorporated by reference in their entirety.

SUMMARY OF THE INVENTION

In one aspect, the invention provides methods for detecting an anti-drug antibody of IgE isotype that bind to a therapeutic anti-IgE antibody in a sample, comprising the steps of: a) contacting a sample that may contain the anti-drug antibody with a mutant therapeutic antibody comprising at least one amino acid mutation from the therapeutic anti-IgE antibody, wherein the relative binding affinity of the mutant therapeutic antibody to an IgE (such as human IgE) is about 10% or less of the relative binding affinity of the therapeutic anti-IgE antibody to the IgE; and b) detecting binding of the anti-drug antibody to the mutant therapeutic antibody.

In some embodiments, the relative binding affinity of the mutant therapeutic antibody is about 7.5% or less, about 5% or less, about 2.5% or less, about 2.0% or less, about 1.5% or less, about 1% or less, about 0.9% or less, about 0.8% or less, about 0.7% or less, about 0.5% or less, about 0.25% or less, about 0.1% or less of the relative binding affinity of the therapeutic anti-IgE antibody.

In another aspect, the invention provides methods for detecting anti-drug antibodies of IgE isotype that bind to a therapeutic anti-IgE antibody in a sample, comprising the steps of: a) contacting a sample that may contain the anti-drug antibodies with a mutant therapeutic antibody having at least one amino acid mutation from the therapeutic anti-IgE antibody, wherein the potency of the mutant therapeutic antibody to an IgE (such as human IgE) is about 10% or less of the potency of the therapeutic anti-IgE antibody to the IgE; and b) detecting binding of the anti-drug antibodies to the mutant therapeutic antibody.

In some embodiments, the potency of the mutant therapeutic antibody is about 7.5% or less, about 5% or less, about 2.5% or less, about 2.0% or less, about 1.5% or less, about 1% or less, about 0.9% or less, about 0.8% or less, about 0.7% or less, about 0.5% or less, about 0.25% or less, about 0.1% or less of the potency of the therapeutic anti-IgE antibody.

Any of the mutant therapeutic antibodies provided herein may be used. In some embodiments, the mutant therapeutic antibody comprises one, two, three, four, five, or six amino acid mutations in CDR sequences of the heavy and/or light chain of the therapeutic anti-IgE antibody. In some embodiments, the therapeutic anti-IgE antibody is omalizumab, and the mutant therapeutic antibody comprises one, two, or three amino acid mutations in the first CDR of the light chain of omalizumab. In some embodiments, the therapeutic anti-IgE antibody is omalizumab, and the mutant therapeutic antibody comprises an amino acid substitution at position 34 (Asp) in the light chain (SEQ ID NO:1) of omalizumab. In some embodiments, the mutant therapeutic antibody comprises the heavy chain amino acid sequence of SEQ ID NO:2 and the light chain amino acid sequence of SEQ ID NO:1, wherein amino acids at positions 30 (Asp) and 34 (Asp) or positions 32 (Asp) and 34 (Asp) in the light chain are substituted. In some embodiments, the mutant therapeutic antibody comprises the heavy chain amino acid sequence of SEQ ID NO:2 and the light chain amino acid sequence of SEQ ID NO:1, wherein amino acid D (Asp) at positions 30, 32, and 34 are substituted in the light chain. In some embodiments, amino acid Asp is substituted with Ala. In some embodiments, the mutant therapeutic antibody comprises the heavy chain amino acid sequence of SEQ ID NO:2 and the light chain amino acid sequence of SEQ ID NO:1 with amino acid substitutions of Asp to Ala at positions 30, 32, and 34 in the light chain. In some embodiments, the therapeutic anti-IgE antibody is omalizumab, and the mutant therapeutic antibody comprises one, two, or three amino acid mutations in the third CDR of the heavy chain of omalizumab. In some embodiments, the mutant therapeutic antibody comprises the heavy chain amino acid sequence of SEQ ID NO:2 and the light chain amino acid sequence of SEQ ID NO:1, wherein amino acids at positions 101 (His), 105 (His) and 107 (His) in the heavy chain (SEQ ID NO:2) are substituted. In some embodiments, amino acid His is substituted with Ala. In some embodiments, the mutant therapeutic antibody comprises the heavy chain amino acid sequence of SEQ ID NO:2 with amino acid substitutions of His to Ala at positions 101, 105, and 107 in the heavy chain and the light chain amino acid sequence of SEQ ID NO:1.

In some embodiments, the mutant therapeutic antibody is immobilized or captured to a surface. In some embodiments, the mutant therapeutic antibody is directly immobilized to a surface. In some embodiments, the mutant therapeutic antibody is conjugated to a label and is immobilized or captured to the surface through a capture agent that specifically binds to the label, wherein the capture agent is immobilized to the surface. In some embodiments, the label is biotin and the capture agent is streptavidin. In some embodiments, the label is digoxigenin and the capture agent is an anti-digoxigenin antibody.

In some embodiments, the sample is contacted with the mutant therapeutic antibody that is immobilized or captured to a surface. In some embodiments, the sample is contacted with the mutant therapeutic antibody before the mutant therapeutic antibody is captured to a surface. In some embodiments, the mutant therapeutic antibody is captured to a surface after the sample is contacted with the mutant therapeutic antibody and before detecting binding of the anti-drug antibody to the mutant therapeutic antibody.

In some embodiments, the binding of the anti-drug antibodies to the mutant therapeutic antibody is detected with a detecting agent. In some embodiments, the detecting agent is an FcεRIα polypeptide that binds to an Fc region of an IgE. Any of the FcεRIα polypeptides provided herein may be used. In some embodiments, the FcεRIα polypeptide comprises an extracellular domain of an FcεRIα subunit. In some embodiments, the FcεRIα polypeptide comprises an extracellular domain of an FcεRIα subunit fused to an IgG constant region. In some embodiments, the FcεRIα polypeptide is labeled. In some embodiments, the label is selected from the group consisting of biotin, digoxigenin, ruthenium, a radiologic label, a photoluminescent label, a chemiluminescent label, a fluorescent label, an electrochemiluminescent label, and an enzyme label. In some embodiments, the FcεRIα polypeptide is labeled with biotin, and the binding of the anti-drug antibody to the mutant therapeutic antibody is detected by streptavidin-HRP. In some embodiments, the FcεRIα polypeptide is labeled with digoxigenin, and the binding of the anti-drug antibody to the mutant therapeutic antibody is detected by a HRP conjugated anti-digoxigenin antibody. In some embodiments, the FcεRIα polypeptide is labeled with ruthenium, and the binding of the anti-drug antibody to the mutant therapeutic antibody is detected by an electrochemiluminescence assay.

In some embodiments, the sample contains human serum or plasma. In some embodiments, the sample contains the therapeutic anti-IgE antibody. In some embodiments, the sample does not contain the therapeutic anti-IgE antibody. In some embodiments, the serum or plasma contains omalizumab. In other embodiments, the serum or plasma does not contain omalizumab.

In some embodiments, the methods further comprise a step of comparing the binding of the anti-drug antibodies to the mutant therapeutic antibody to a reference. In some embodiments, the reference is the detected binding between the mutant therapeutic antibody and a control antibody. In some embodiments, the control antibody is a positive control antibody that binds both the therapeutic anti-IgE antibody and the mutant therapeutic antibody with similar affinity. In some embodiments, the positive control antibody comprises a heavy chain variable region comprising the amino acid sequence shown in SEQ ID NO:7 and a light chain variable region comprising the amino acid sequence shown in SEQ ID NO:8. In some embodiments, the positive control antibody further comprises the heavy chain and light chain constant regions from a human IgE.

In another aspect, the invention also provides kits for detecting an anti-drug antibody of IgE isotype that binds to a therapeutic anti-IgE antibody in a sample comprising (a) a mutant therapeutic antibody comprising at least one amino acid mutation from the therapeutic anti-IgE antibody, wherein the relative binding affinity of the mutant therapeutic antibody to an IgE (such as human IgE) is about 10% or less of the relative binding affinity of the therapeutic anti-IgE antibody to the IgE; and b) a detecting agent that binds to an Fc region of an IgE. Any of the mutant therapeutic antibodies provided herein may be used. In some embodiments, the detecting agent is an FcεRIα polypeptide. Any of the FcεRIα polypeptides provided herein may be included in the kit. In some embodiments, the FcεRIα polypeptide comprises an extracellular domain of an FcεRIα subunit. In some embodiments, the FcεRIα polypeptide comprises an extracellular domain of an FcεRIα subunit fused to an IgG constant region. In some embodiments, the FcεRIα polypeptide is labeled (such as labeled by biotin, digoxigenin, ruthenium, etc.). In some embodiments, the kit further comprises streptavidin-HRP or Amdex SA-HRP. In some embodiments, the kit further comprises HRP-conjugated anti-digoxigenin antibody for detecting digoxigenin labeled FcεRIα polypeptide. In some embodiments, the kit further comprises a positive control antibody that binds both the therapeutic anti-IgE antibody and the mutant therapeutic antibody with similar affinity. In some embodiments, the positive control antibody comprises a heavy chain variable region comprising the amino acid sequence shown in SEQ ID NO:7 and a light chain variable region comprising the amino acid sequence shown in SEQ ID NO:8. In some embodiments, the positive control antibody further comprises the heavy chain and light chain constant regions from a human IgE.

In another aspect, the invention also provides kits for detecting anti-drug antibodies of IgE isotype that bind to a therapeutic anti-IgE antibody in a sample comprising a) a mutant therapeutic antibody having at least one amino acid mutation from the therapeutic anti-IgE antibody, wherein the potency of the mutant therapeutic antibody to an IgE (such as human IgE) is about 10% or less of the potency of the therapeutic anti-IgE antibody to the IgE; and b) a detecting agent that binds to an Fc region of an IgE. Any of the mutant therapeutic antibodies provided herein may be used. In some embodiments, the detecting agent is an FcεRIα polypeptide. Any of the FcεRIα polypeptides provided herein may be included in the kit. In some embodiments, the FcεRIα polypeptide comprises an extracellular domain of an FcεRIα subunit. In some embodiments, the FcεRIα polypeptide comprises an extracellular domain of an FcεRIα subunit fused to an IgG constant region. In some embodiments, the FcεRIα polypeptide is labeled (such as labeled by biotin, digoxigenin, ruthenium, etc.). In some embodiments, the kit further comprises streptavidin-HRP or Amdex SA-HRP. In some embodiments, the kit further comprises HRP-conjugated anti-digoxigenin antibody for detecting digoxigenin labeled FcεRIα polypeptide. In some embodiments, the kit further comprises a positive control antibody that binds both the therapeutic anti-IgE antibody and the mutant therapeutic antibody with similar affinity. In some embodiments, the positive control antibody comprises a heavy chain variable region comprising the amino acid sequence shown in SEQ ID NO:7 and a light chain variable region comprising the amino acid sequence shown in SEQ ID NO:8. In some embodiments, the positive control antibody further comprises the heavy chain and light chain constant regions from a human IgG.

In another aspect, the invention also provides methods for detecting an anti-drug antibody of IgE isotype that binds to a therapeutic anti-IgE antibody in a sample, comprising the steps of: (a) contacting a sample that may contain the anti-drug antibody with (i) a mutant therapeutic antibody and (ii) an FcεRIα polypeptide that binds to an Fc region of a human IgE, wherein the mutant therapeutic antibody comprises at least one amino acid mutation from the therapeutic anti-IgE antibody, and the relative binding affinity of the mutant therapeutic antibody to human IgE is about 10% or less of the relative binding affinity of the therapeutic anti-IgE antibody to said human IgE; (b) capturing the mutant therapeutic antibody to a surface; and (c) detecting binding of the anti-drug antibody to the mutant therapeutic antibody.

In some embodiments, excess amount of FcεRIα polypeptide is contacted with the sample in step (a). In some embodiments, at least about 2-fold, at least about 3-fold, at least about 4-fold, at least about 5-fold, at least about 6-fold, at least about 7-fold, at least about 8-fold, at least about 9-fold, or at least about 10-fold excess of FcεRIα polypeptide is contacted with the sample in step (a). Any of the FcεRIα polypeptides provided herein may be used. In some embodiments, the FcεRIα polypeptide comprises an extracellular domain of an FcεRIα subunit. The FcεRIα polypeptide may be labeled or not labeled.

Any of the mutant therapeutic antibodies provided herein may be used. In some embodiments, the mutant therapeutic antibody is labeled and is captured to the surface by a capture agent that specifically binds to the label. In some embodiments, the label is biotin and the surface is coated with streptavidin. In some embodiments, the binding of the anti-drug antibody to the mutant therapeutic antibody is detected by a labeled anti-human IgE antibody. In some embodiments, the FcεRIα polypeptide is labeled and the binding of the anti-drug antibody to the mutant therapeutic antibody is detected by a detecting agent that specifically binds to the label on the FcεRIα polypeptide. In some embodiments, the FcεRIα polypeptide is labeled with digoxigenin, and the binding of the anti-drug antibody to the mutant therapeutic antibody is detected by a HRP conjugated anti-digoxigenin antibody. In some embodiments, the FcεRIα polypeptide is labeled with ruthenium, and the binding of the anti-drug antibody to the mutant therapeutic antibody is detected by an electrochemiluminescence assay.

In another aspect, the invention also provides kits for detecting an anti-drug antibody of IgE isotype that binds to a therapeutic anti-IgE antibody in a sample comprising: (a) a mutant therapeutic antibody comprising at least one amino acid mutation from the therapeutic anti-IgE antibody, wherein the relative binding affinity of the mutant therapeutic antibody to human IgE is about 10% or less of the relative binding affinity of the therapeutic anti-IgE antibody to human IgE; and (b) an FcεRIα polypeptide that binds to an Fc region of a human IgE. Any of the mutant therapeutic antibodies provided herein may be used. Any of the FcεRIα polypeptide described herein may be used. In some embodiments, excess amount of FcεRIα polypeptide is provided in the kit. In some embodiments, the FcεRIα polypeptide is labeled. In some embodiments, the kit further comprises a detecting agent that specifically binds to the label on the FcεRIα polypeptide. In some embodiments, the kit further comprises an anti-human IgE antibody. In some embodiments, the anti-human IgE antibody is labeled.

In another aspect, the invention also provides methods for detecting an anti-drug antibody of IgE isotype that binds to a therapeutic anti-IgE antibody in a sample, comprising the steps of: (a) preincubating a sample that may contain the anti-drug antibody with excess amount of an FcεRIα polypeptide that binds to an Fc region of a human IgE; (b) incubating the preincubated sample from step (a) with the therapeutic anti-IgE antibody or a mutant therapeutic antibody comprising at least one amino acid mutation from the therapeutic anti-IgE antibody, and the relative binding affinity of the mutant therapeutic antibody to a human IgE is reduced as compared to the relative binding affinity of the therapeutic anti-IgE antibody to said human IgE; and (c) detecting binding of the anti-drug antibody to the therapeutic anti-IgE antibody or the mutant therapeutic antibody.

Any of the mutant therapeutic antibodies provided herein may be used. In some embodiments, the mutant therapeutic antibody comprises at least one amino acid mutation from the therapeutic anti-IgE antibody, and the relative binding affinity of the mutant therapeutic antibody to human IgE is about 10% or less of the relative binding affinity of the therapeutic anti-IgE antibody to said human IgE.

In some embodiments, at least about 2-fold, at least about 3-fold, at least about 4-fold, at least about 5-fold, at least about 6-fold, at least about 7-fold, at least about 8-fold, at least about 9-fold, or at least about 10-fold excess of FcεRIα polypeptide is preincubated with the sample in step (a). Any of the FcεRIα polypeptides provided herein may be used.

In some embodiments, the therapeutic anti-IgE antibody or the mutant therapeutic antibody is captured to a surface before or after incubating with the sample in step (b). In some embodiments, the therapeutic anti-IgE antibody or the mutant therapeutic antibody is directly immobilized to a surface before incubating with the sample in step (b).

In some embodiments, the therapeutic anti-IgE antibody or the mutant therapeutic antibody is labeled and is captured to the surface through an immobilized capture agent that specifically binds to the label. In some embodiments, the therapeutic anti-IgE antibody or the mutant therapeutic antibody is labeled with biotin and is captured to a streptavidin coated surface.

In some embodiments, the binding of the anti-drug antibody to the therapeutic antibody or the mutant therapeutic antibody is detected by a HRP conjugated anti-human IgE antibody. In some embodiments, the FcεRIα polypeptide is labeled, and the binding of the anti-drug antibody to the therapeutic anti-IgE antibody or the mutant therapeutic antibody is detected by detecting the label. In some embodiments, the FcεRIα polypeptide is labeled with digoxigenin, and the binding of the anti-drug antibody to the therapeutic antibody or the mutant therapeutic antibody is detected by a HRP conjugated anti-digoxigenin antibody. In some embodiments, the FcεRIα polypeptide is labeled with ruthenium, and the binding of the anti-drug antibody to the therapeutic anti-IgE antibody or the mutant therapeutic antibody is detected by an electrochemiluminescence assay.

In another aspect, the invention also provides kits for detecting an anti-drug antibody of IgE isotype that binds to a therapeutic anti-IgE antibody in a sample comprising: (a) the therapeutic anti-IgE antibody or a mutant therapeutic antibody thereof, wherein the mutant therapeutic antibody comprises at least one amino acid mutation from the therapeutic anti-IgE antibody, wherein the relative binding affinity of the mutant therapeutic antibody to human IgE is reduced as compared to the relative binding affinity of the therapeutic anti-IgE antibody to human IgE; and (b) an FcεRIα polypeptide that binds to an Fc region of a human IgE. Any of the mutant therapeutic antibodies provided herein may be used. In some embodiments, the kit further comprises an anti-human IgE antibody. In some embodiments, the anti-human IgE antibody is labeled. Any of the FcεRIα polypeptide provided herein may be used. In some embodiments, the FcεRIα polypeptide is labeled. In some embodiments, the kit further comprises a detecting agent that specifically binds to the label on the FcεRIα polypeptide.

In another aspect, the invention provides methods of identifying a patient having a risk of anaphylactic reaction to a therapeutic anti-IgE antibody, comprising the steps of: (a) contacting a sample from the patient with a mutant therapeutic antibody comprising at least one amino acid mutation from the therapeutic anti-IgE antibody, wherein the relative binding affinity of the mutant therapeutic antibody to human IgE is about 10% or less of the relative binding affinity of the therapeutic anti-IgE antibody to said human IgE; and (b) detecting binding of an anti-drug antibody of IgE isotype to the mutant therapeutic antibody, wherein the presence and/or the level of the anti-drug antibody in the sample indicates that the patient has a risk of anaphylactic reaction to the therapeutic anti-IgE antibody.

In another aspect, the invention provides methods of identifying a patient having a risk of anaphylactic reaction to a therapeutic anti-IgE antibody, comprising the steps of: (a) contacting a sample from the patient with a mutant therapeutic antibody comprising at least one amino acid mutation from the therapeutic anti-IgE antibody, wherein the potency of the mutant therapeutic antibody to human IgE is about 10% or less of the potency of the therapeutic anti-IgE antibody to said human IgE; and (b) detecting binding of an anti-drug antibody of IgE isotype to the mutant therapeutic antibody, wherein the presence and/or the level of the anti-drug antibody in the sample indicates that the patient has a risk of anaphylactic reaction to the therapeutic anti-IgE antibody.

In another aspect, the invention provides methods of identifying a patient having a risk of anaphylactic reaction to a therapeutic anti-IgE antibody, comprising the steps of: (a) contacting a sample from a patient with (i) a mutant therapeutic antibody and (ii) an FcεRIα polypeptide that binds to an Fc region of a human IgE, wherein the mutant therapeutic antibody comprises at least one amino acid mutation from the therapeutic anti-IgE antibody, and the relative binding affinity of the mutant therapeutic antibody to human IgE is about 10% or less of the relative binding affinity of the therapeutic anti-IgE antibody to said human IgE; (b) capturing the mutant therapeutic antibody to a surface; and (c) detecting binding of an anti-drug antibody of IgE isotype to the mutant therapeutic antibody, wherein the presence and/or the level of the anti-drug antibody in the sample indicates that the patient has a risk of anaphylactic reaction to the therapeutic anti-IgE antibody.

In another aspect, the invention provides methods of identifying a patient having a risk of anaphylactic reaction to a therapeutic anti-IgE antibody, comprising the steps of: (a) preincubating a sample from a patient with excess amount of an FcεRIα polypeptide that binds to an Fc region of a human IgE; (b) incubating the preincubated sample from step (a) with the therapeutic anti-IgE antibody or a mutant therapeutic antibody comprising at least one amino acid mutation from the therapeutic anti-IgE antibody, and the relative binding affinity of the mutant therapeutic antibody to human IgE is reduced as compared to the relative binding affinity of the therapeutic anti-IgE antibody to said human IgE; and (c) detecting binding of an anti-drug antibody of IgE isotype to the therapeutic anti-IgE antibody or the mutant therapeutic antibody, wherein the presence and/or the level of the anti-drug antibody in the sample indicates that the patient has a risk of anaphylactic reaction to the therapeutic anti-IgE antibody.

In another aspect, the invention provides methods of treating a patient having an IgE-mediated disorder, comprising the steps of: (a) determining the level of an anti-drug antibody of IgE isotype to a therapeutic anti-IgE antibody in a sample from the patient; (b) administering an effective amount of the therapeutic anti-IgE antibody to the patient if the level of the anti-drug antibody in the sample do not indicate that the patient has a risk of anaphylactic reaction to the therapeutic anti-IgE antibody. The level of the anti-drug antibody may be determined by any of the methods provided herein.

It is to be understood that one, some, or all of the properties of the various embodiments described herein may be combined to form other embodiments of the present invention. These and other aspects of the invention will become apparent to one of skill in the art.

BRIEF DESCRIPTION OF THE FIGURES

FIG. 1A shows the light chain amino acid sequence of antibody E25 (SEQ ID NO:1).

FIG. 1B shows the heavy chain amino acid sequence of antibody E25 (SEQ ID NO:2). The CDR regions as defined by Chothia are shown in boldface, while the CDR regions as defined by Kabat are delineated with brackets.

FIG. 2A is a diagrammatic representation of an ELISA assay to compare the binding affinity of E25 and E25-AAA mutant to purified human IgE.

FIG. 3 is a diagrammatic representation of a potency assay for therapeutic anti-IgE antibodies.

FIG. 6A is diagrammatic representation of an assay system for testing binding of the chimeric E25-specific IgE positive control antibody to E25 antibody or E25-AAA mutant antibody.

FIG. 7 is a diagrammatic representation of an assay for detecting E25-specific antibodies of IgE isotype using E25-AAA mutant antibody.

Figure 2B:
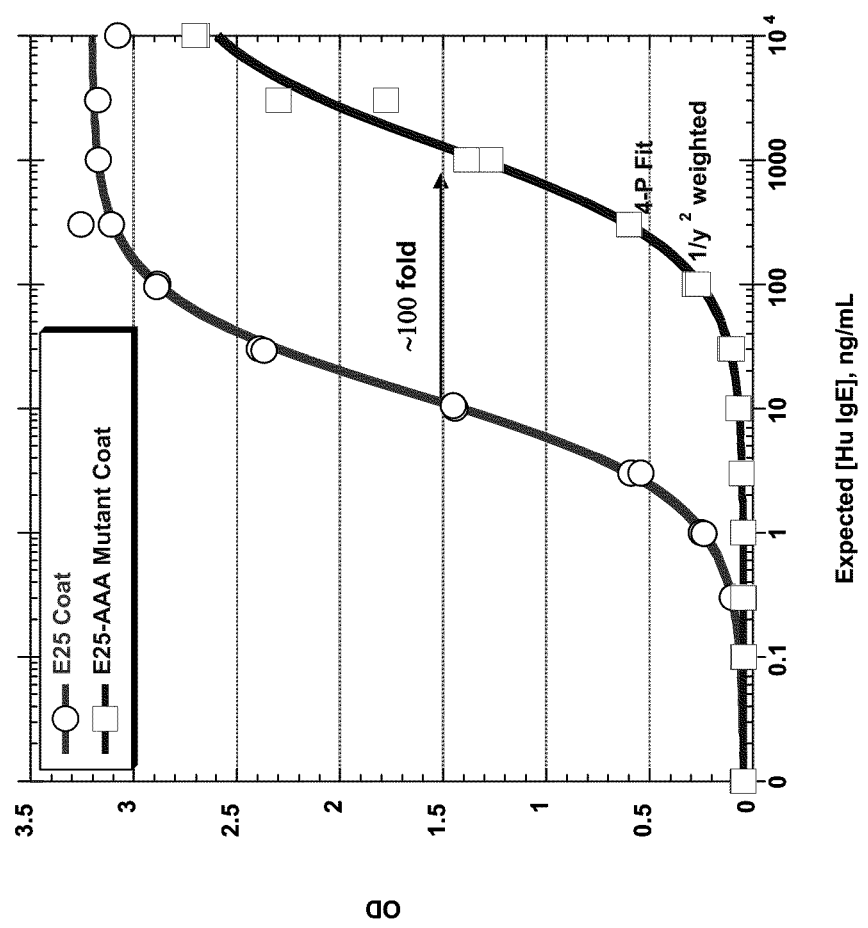
FIG. 2B is a graph showing binding of E25-AAA mutant to human IgE as compared to binding of E25 to human IgE. E25-AAA mutant had about 100× less affinity for IgE than E25.
Figure 4B:
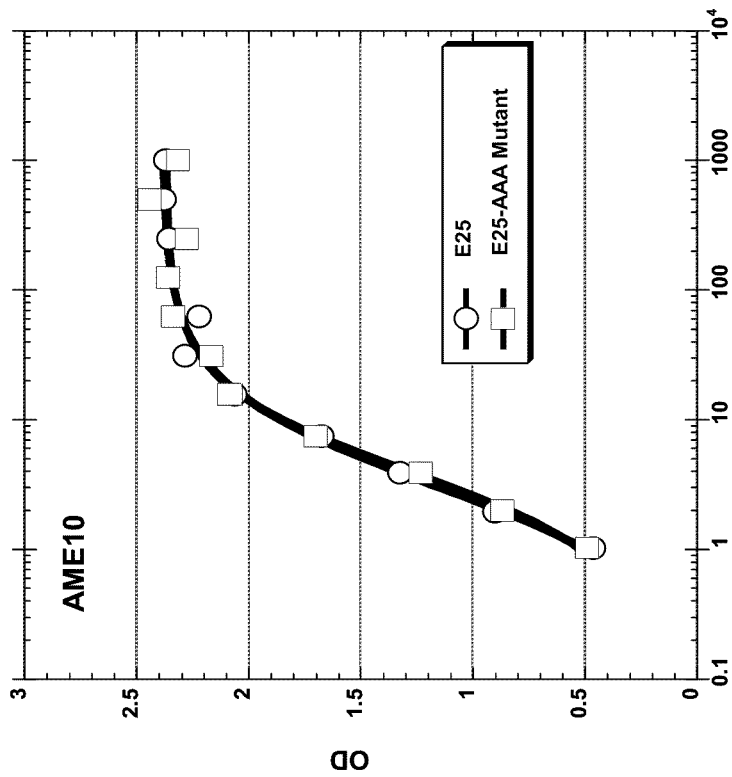
FIG. 4B is a graph showing binding of AME10 to E25 as compared to binding of AME10 to E25-AAA mutant.
Figure 4A:
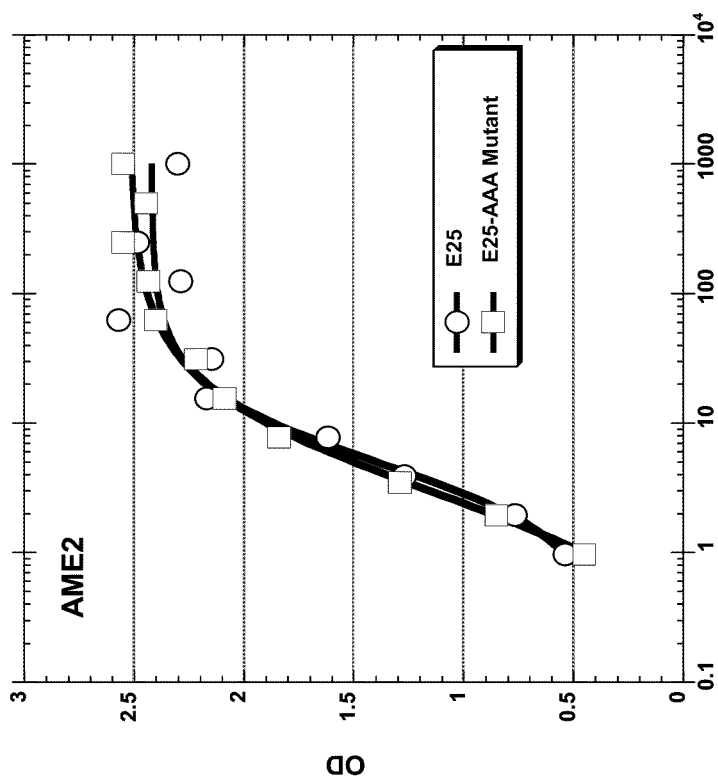
FIG. 4A is a graph showing binding of AME2 to E25 as compared to binding of AME2 to E25-AAA mutant.
Figure 4D:
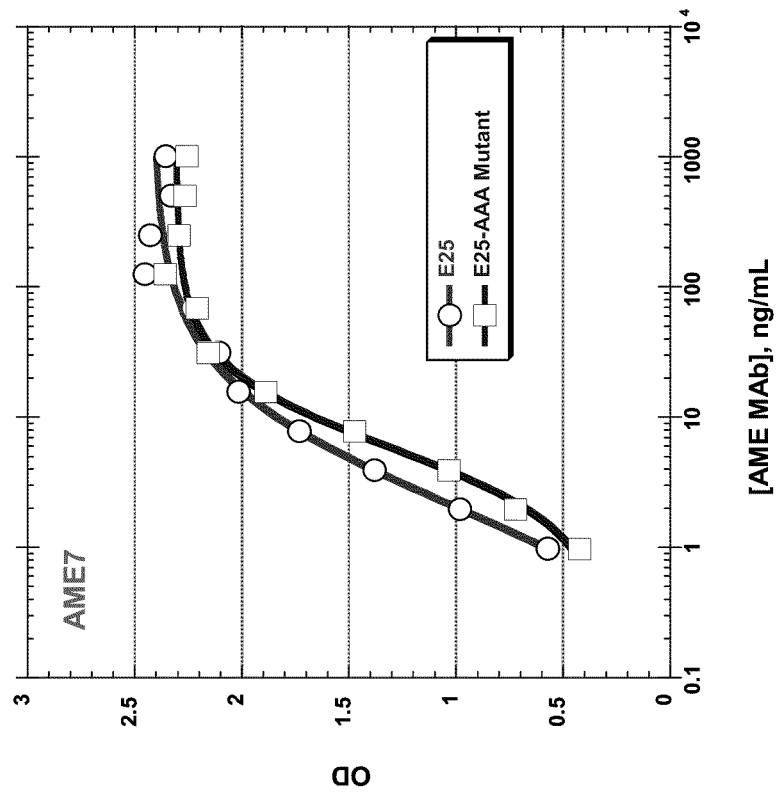
FIG. 4D is a graph showing binding of AME7 to E25 as compared to binding of AME7 to E25-AAA mutant.
Figure 4C:
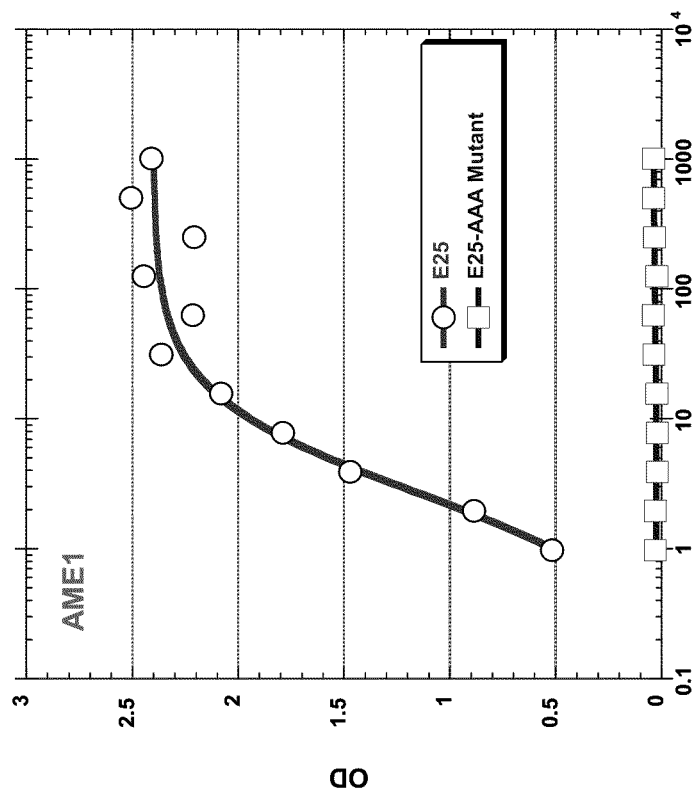
FIG. 4C is a graph showing binding of AME1 to E25 as compared to binding of AME1 to E25-AAA mutant.
Figures 4E, 4F:
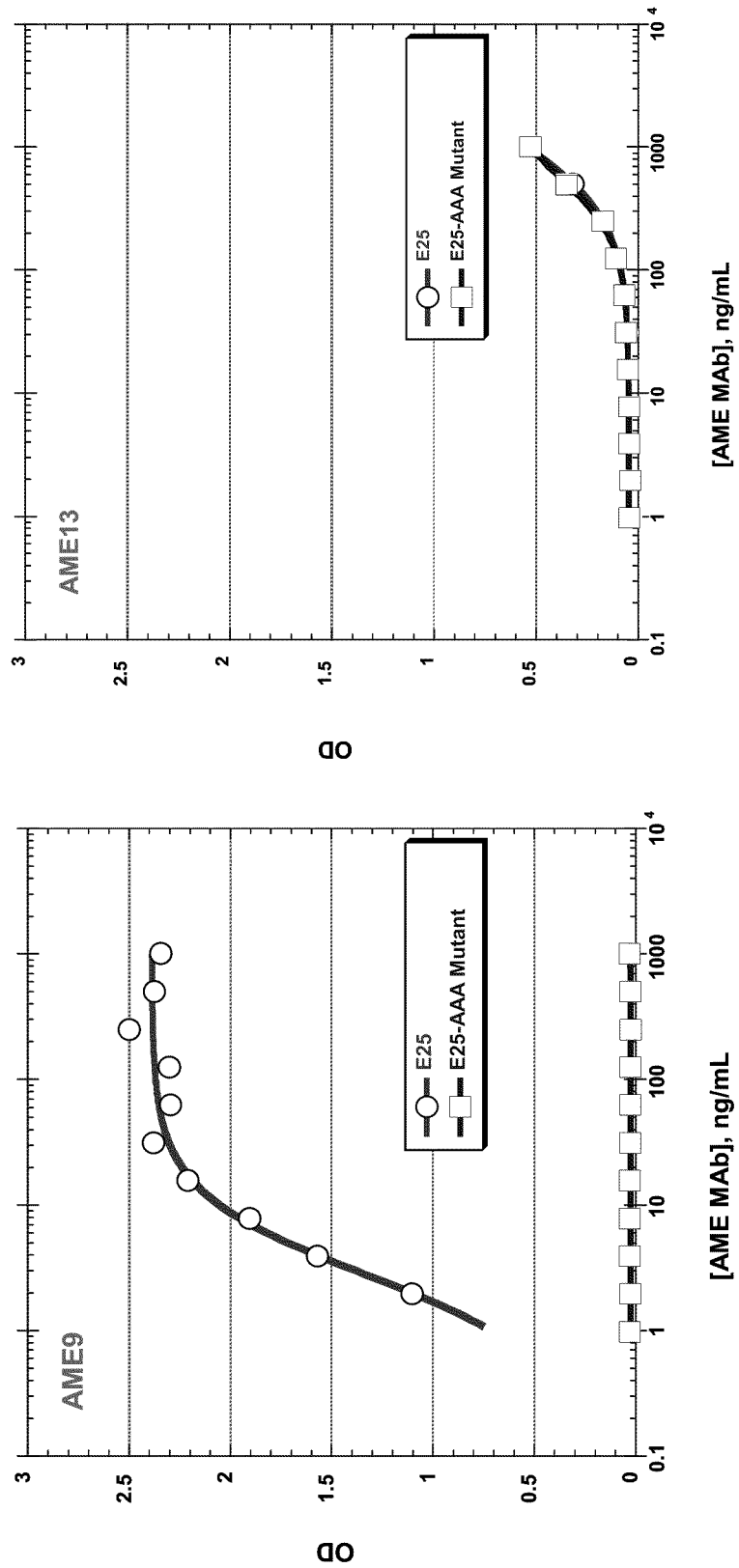
FIG. 4E is a graph showing binding of AME9 to E25 as compared to binding of AME9 to E25-AAA mutant.
FIG. 4F is a graph showing binding of AME13 to E25 as compared to binding of AME13 to E25-AAA mutant.
Figures 4G, 4H:
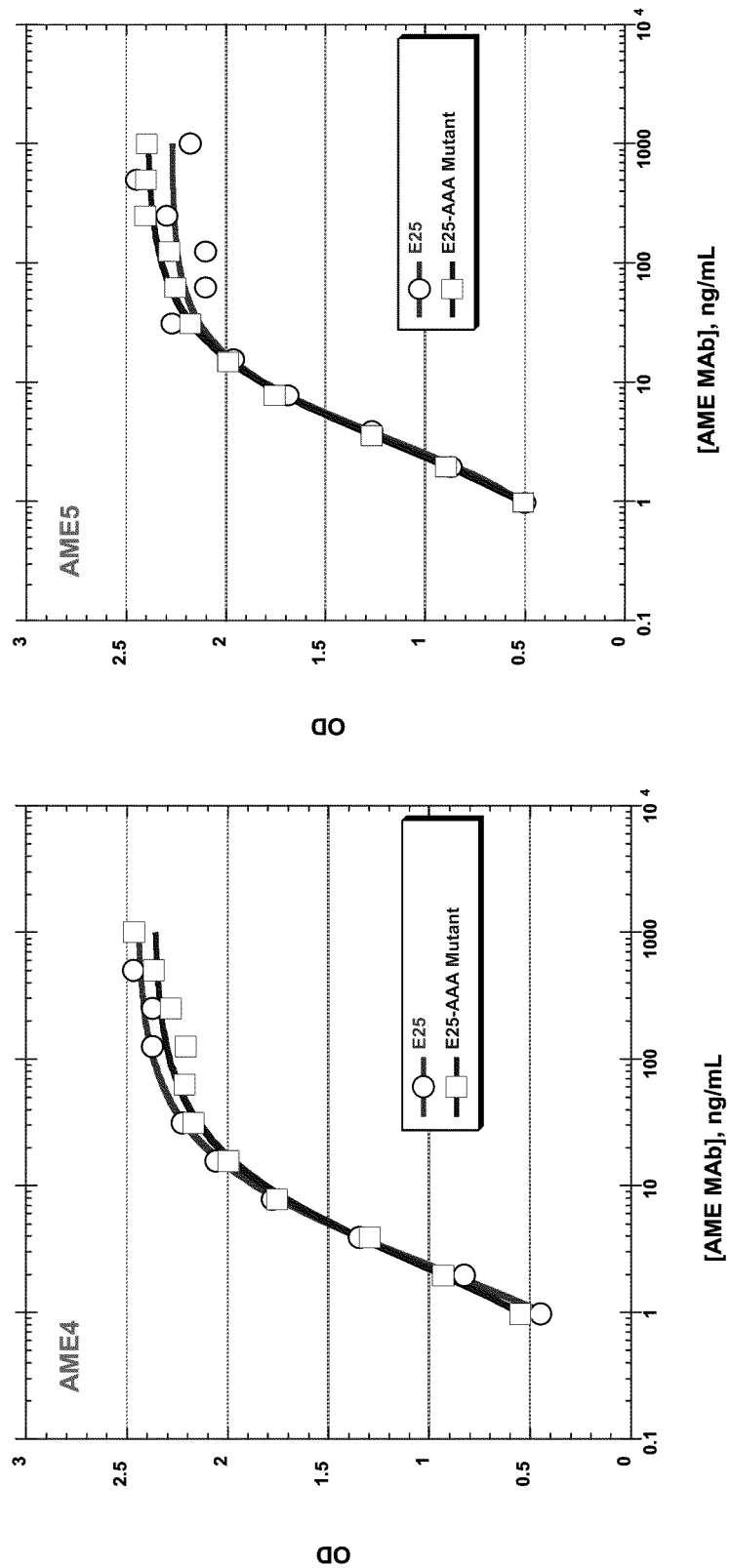
FIG. 4G is a graph showing binding of AME4 to E25 as compared to binding of AME4 to E25-AAA mutant.
FIG. 4H is a graph showing binding of AME5 to E25 as compared to binding of AME5 to E25-AAA mutant.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816, 567), phage display technologies (see, e.g., Clackson et al., *Nature*, 352:624-628 (1991); Marks et al., *J. Mol. Biol.*, 222: 581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/ 34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995).

The monoclonal antibodies herein specifically include "chimeric" antibodies. "Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the known techniques for making human antibodies. This definition of a human antibody specifically excludes a humanized antibody comprising non-human antigen-binding residues.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|   |   | (Kabat Numbering) |   |   |
| H1 | H31-H35 | H26-H35 | H26-H32 | H30-H35 |
|   |   | (Chothia Numbering) |   |   |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

"Binding" or "specific binding" generally refers to binding between two molecules (such as between an antibody and one or more targets, an anti-IgE antibody and an IgE, and an anti-drug antibody and the drug) with sufficient affinity. Preferably, the extent of binding of an antibody to an unrelated molecule is less than about 10% of the binding of the antibody to a target as measured, e.g., by a radioimmunoassay (RIA). In some embodiments, the antibody that binds to its target has a dissociation constant (Kd) of $\leq 1$ μM, $\leq 100$ nM, $\leq 10$ nM, $\leq 1$ nM, or $\leq 0.1$ nM.

"Binding affinity" generally refers to the strength of the sum total of monovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., J. Mol. Biol. 293:865-881 (1999)). To establish conditions for the assay, MICROTITER® multi-well plates (Thermo Scientific) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 μl/well of scintillant (MICROSCINT-20™; Packard) is added, and the plates are counted on a TOPCOUNT™ gamma counter (Packard) for ten minutes.

Concentrations of each Fab that give less than or equal to 20% of maximal binding are chosen for use in competitive binding assays.

According to another embodiment, the Kd or Kd value may be measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 ul/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293: 865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (Thermo-Spectronic) with a stirred cuvette.

An "on-rate," "rate of association," "association rate," or "kon" according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., relative binding affinity values). The difference between said two values is, for example, less than about 50%, less than about 40%, less than about 30%, less than about 20%, and/or less than about 10% as a function of the reference/comparator value The term "sample", as used herein, refers to a composition that is obtained or derived from a subject of interest. Samples include, but are not limited to, whole blood, serum, or plasma from an individual.

"Total IgE" refers to a total amount of IgE present in a sample, including free, unbound IgE and IgE complexed with a binding partner. "Free IgE" refers to IgE not bound to a binding partner.

A "subject", an "individual", or a "patient" used herein is a mammal, more preferably a human. Mammals include, but are not limited to, humans, primates, farm animal, sport animals (e.g., horses), rodents, and pets (e.g., dogs and cats).

As used herein, method for "aiding assessment" refers to methods that assist in making a clinical determination (e.g., risk of anaphylaxis), and may or may not be conclusive with respect to the definitive assessment.

As used herein, a "reference value" can be an absolute value; a relative value; a value that has an upper and/or lower limit; a range of values; an average value; a median value; a mean value; or a value as compared to a particular control or baseline value.

The term "detecting" or "detection" is used in the broadest sense to include both qualitative and quantitative measurements of a specific molecule, herein measurements of a specific analyte molecule such as an IgE or an anti-drug antibody. In one aspect, a detection method described herein is used to identify the mere presence of an analyte molecule of interest in a sample. In another aspect, a detection method can be used to quantify an amount of analyte molecule in a sample. In still another aspect, the method can be used to determine the relative binding affinity of an analyte molecule of interest for a target molecule.

The term "detecting agent", "detection agent", "detecting reagent", and "detection reagent" are used interchangeably to refer to an agent that detects an analyte molecule, either directly via a label, such as a fluorescent, enzymatic, radioactive, or chemiluminescent label, that can be linked to the detecting agent, or indirectly via a labeled binding partner, such as an antibody or receptor that specifically binds the detecting agent. Examples of detecting agents include, but are not limited to, an antibody, antibody fragment, soluble receptor, receptor fragment, and the like.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed.

The term "assay surface" or "surface" means a substrate on which a capture agent may be immobilized for use in an immunoassay. Suitable assay surfaces include polymeric assay plate, chips, fluidity cards, magnetic beads, resins, cellulose polymer sponge, and the like.

The term "binding domain" refers to the region of a polypeptide that binds to another molecule. In the case of an Fc receptor polypeptide or FcR, the binding domain can comprise a portion of a polypeptide chain thereof (e.g. the α-chain thereof) that is responsible for binding an Fc region of an immunoglobulin or other Fc region containing molecule. One useful binding domain is the extracellular domain (ECD) of an Fc receptor α-chain polypeptide. As described herein, the extracellular domain of the FcεRIα-chain contains a binding domain that binds the Fc region of an Ig, for example IgE.

The term "capture agent" or "capture reagent" refers to a agent capable of binding and capturing a target molecule or analyte molecule in a sample. Typically, a capture agent or reagent is immobilized, for example, on a solid substrate, such as a microparticle or bead, microtiter plate, column resin, chip, fluidity card, magnetic bead, cellulose polymer sponge, and the like. The capture agent can be an antigen, soluble receptor, antibody, a mixture of different antibodies, and the like.

"Chimeric" polypeptides are polypeptides in which a portion of the polypeptide sequence is derived from one species, while at least one other portion corresponds to a sequence derived from a different species.

The term "label" when used herein refers to a compound or composition which is conjugated or fused directly or indirectly to a reagent such as a nucleic acid probe, a polypeptide or an antibody and facilitates detection or capture of the reagent to which it is conjugated or fused. The label may itself be detectable (e.g., radioisotope, fluorescent, photoluminescent, chemiluminescent, or electrochemiluminescent labels), detectable after binding to another molecule, or in the case of an enzymatic label, may catalyze chemical alteration of a substrate compound or composition which is detectable.

The term "target molecule" refers to a specific binding target of an analyte molecule. A target molecule can be, for example, an antigen if the analyte molecule is an antibody. The target molecule can be, for example, a polypeptide or antibody having therapeutic activity. In one embodiment, the target molecule is a therapeutic antibody and the analyte molecule is an anti-drug antibody that binds the therapeutic antibody.

"Analyte" and "analyte molecule," as used herein, refer to a molecule that is analyzed by the methods of the invention, and includes, but is not limited to, anti-drug antibodies.

"Treating" or "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, the therapeutic antibodies described herein are used to delay development of a disease or disorder or to slow the progression of a disease or disorder.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

A "conservative substitution" as used herein, replaces a selected amino acid with another that is not substantially different in character. Amino acids grouped according to character include positively charged amino acids: Lys, Arg, His; negatively charged amino acids: Asp, Glu; amide amino acids: Asn, Gln; aromatic amino acids: Phe, Tyr, Trp; hydrophobic amino acids: Pro, Gly, Ala, Val, Leu, Ile, Met; and uncharged hydrophilic amino acids: Ser, Thr. Preferred conservative amino acid substitutions are shown below:

| Conservative Amino Acid Substitutions | | |
|---|---|---|
| Target AA | Replacement Selected From | Preferred Substitution |
| Ala | Pro, Gly, Ala, Val, Leu, Ile, Met, Ser, Thr | Ser |
| Arg | Lys, Arg, His, Ser, Ala Ser, Ala | Lys |
| Asn | Lys, Arg, His, Asn, Gln, Ser, Ala Ser, Ala | Gln, Ser, Ala |
| Asp | Asp, Glu, Asn, Gln, Ser, Ala | Glu, Ser, Ala |
| Cys | Pro, Gly, Ala, Val, Leu, Ile, Met, Ser, Thr | Ala, Ser |
| Gln | Lys, Arg, His, Asn, Gln, Ser, Ala | Asn, Ser, Ala |
| Glu | Asp, Glu, Asn, Gln Ser, Ala | Asp, Ser, Ala |
| Gly | Pro, Gly, Ala, Val, Leu, Ile, Met, Ser, Thr | Pro, Ala |
| His | Lys, Arg, His, Ser, Ala | Ser, Ala |
| Ile | Pro, Gly, Ala, Val, Leu, Met | Ala, Val, Leu |
| Leu | Pro, Gly, Ala, Val, Ile, Met | Ala, Val, Ile |
| Lys | Arg, His, Ser, Ala | Arg, Ser, Ala |
| Met | Pro, Gly, Ala, Val, Leu, Ile | Ala, Val, Leu, Ile |
| Phe | Lys, Arg, His, Tyr, Trp Ala, Val, Leu, Ile | Tyr, Ala, Val, Leu, Ile |
| Pro | Lys, Arg, His, Phe, Tyr, Trp, Gly, Ala | Phe, Gly, Ala |
| Ser | Lys, Arg, His, Thr, Ala | Thr, Ala |
| Thr | Lys, Arg, His, Ser, Ala | Ser, Ala |
| Trp | Phe, Tyr, Trp, Ala | Phe, Ala |
| Tyr | Phe, Tyr, Trp, Ala, Val, Leu, Ile | Phe, Ala, Val, Leu, Ile |
| Val | Pro, Gly, Ala, Val, Leu, Ile, Met, Ser, Ala | Leu, Ile, Ser, Ala |

The terms, "protein," "peptide," and "polypeptide" are used interchangeably to denote an amino acid polymer or a set of two or more interacting or bound amino acid polymers.

"Polypeptide" refers to a peptide or protein containing two or more amino acids linked by peptide bonds, and includes peptides, oligomers, proteins, and the like. Polypeptides can contain natural, modified, or synthetic amino acids. Polypeptides can also be modified naturally, such as by post-translational processing, or chemically, such as amidation acylation, cross-linking, and the like.

As used herein, "a", "an", and "the" can mean singular or plural (i.e., can mean one or more) unless indicated otherwise.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

C. Methods of the Invention

The invention provides methods and reagents that are useful to detected IgE isotype anti-drug antibodies that specifically bind to a therapeutic anti-IgE antibody. The invention also provides methods for identifying an individual having a risk of anaphylaxis to a therapeutic anti-IgE antibody treatment by measuring the presence and/or the level of IgE isotype anti-drug antibodies that bind to the therapeutic antibody in a sample from the individual, and assessing the risk of anaphylaxis based on the presence and/or the level of the IgE isotype anti-drug antibodies in the sample. The invention further provides methods for treating an individual having IgE-mediated disorders comprising determining the presence and/or level of anti-drug antibodies to a therapeutic anti-IgE antibody in a sample from the individual, and administering an effective amount of the therapeutic anti-IgE antibody to the individual if the level of the anti-drug antibodies in the sample indicates that the individual does not have a risk of analphylactic reaction to the therapeutic anti-IgE antibody.

Therapeutic Anti-IgE Antibodies and Mutant Therapeutic Antibodies

The methods of the invention is useful to detect anti-drug antibodies of IgE isotype that specifically bind to an anti-IgE therapeutic antibody. The difficulties of developing such an assay include the ability to distinguish binding to an endogenous IgE to which the anti-IgE antibody targets and to an IgE that specifically binds to the anti-IgE antibody (i.e., anti-drug antibody of IgE isotype). In some embodiments, the IgE is a human IgE.

As used herein, an "anti-IgE antibody" or a "therapeutic anti-IgE antibody" is an antibody that binds to an IgE in such a manner so as to inhibit or substantially reduce the binding of such IgE to the high affinity receptor (FcεRI). Exemplary anti-IgE antibodies, include, for example, E25 (omalizumab), E26, E27, as well as CGP-5101 (Hu-901) and the HA antibody. The amino acid sequences of the heavy and light chain variable domains and the full length heavy and light chain of the humanized anti-IgE antibodies E25, E26, and E27 are disclosed, for example in U.S. Pat. No. 6,172,213 (FIGS. 2 and 12) and WO 99/01556. The CGP-5101 (Hu-901) antibody is described in Come et al., 1997, *J. Clin. Invest.* 99(5): 879-887, WO 92/17207, and ATTC Deposit Nos. BRL-10706, 11130, 11131, 11132, and 11133. FIG. 1 shows the full-length amino acid sequences of anti-IgE antibody E25 (omalizumab). The HA antibody is antibody MAb2 (CL-2C) shown in Table 2, Example 10 in WO2004/070011, and WO2004/070010. The cell line that produces the HA antibody was deposited at American Type Culture Collection (ATCC) on Dec. 3, 2003 with ATCC No. PTA-5678.

In some embodiments, the methods of the invention use a mutant anti-IgE antibody that has a significant lower binding affinity (including relative binding affinity) and/or potency to an IgE (such as a human IgE) than the unmodified therapeutic anti-IgE antibody. The mutant therapeutic anti-IgE antibody may be designed to have one or more of the following characteristics: a) the binding affinity (including relative binding affinity) of the mutant antibody to an IgE is about 10% or less of the binding affinity (including relative binding affinity) of the therapeutic anti-IgE antibody to the IgE; b) the potency of the mutant antibody to an IgE is about 10% or less of the potency of the therapeutic anti-IgE antibody; c) the mutant antibody has the same or similar tertiary structure as the therapeutic anti-IgE antibody; d) the mutant antibody has the same or similar glycan levels as the therapeutic anti-IgE antibody; and e) the mutant antibody has the same or similar binding affinity to one or more control anti-drug antibodies as compared to the therapeutic anti-IgE antibody. A mutant therapeutic antibody having the minimum number of amino acid mutations in the variable regions effective to reduce relative binding affinity and/or potency to an IgE may be selected for use in the assays described herein. In some embodiments, the mutant antibody comprises one, two, three, four, five, or six amino acid mutations (e.g., substitutions, deletions, or additions) in one or more CDRs (such as one, two, or three of CDR1, CDR2, and CDR3) of the heavy and/or light chain of the therapeutic anti-IgE antibody.

In some embodiments, the potency of the mutant antibody to an IgE is about 10% or less, about 7.5% or less, about 5% or less, about 2.5% or less, about 2.0% or less, about 1.5% or less, about 1% or less, about 0.9% or less, about 0.8% or less, about 0.7% or less, about 0.5% or less, about 0.25% or less, or about 0.1% or less of the potency of the therapeutic anti-IgE antibody to the IgE.

In some embodiments, the relative binding affinity of the mutant therapeutic antibody to an IgE is about 10% or less, about 7.5% or less, about 5% or less, about 2.5% or less, about 2.0% or less, about 1.5% or less, about 1% or less, about 0.9% or less, about 0.8% or less, about 0.7% or less, about 0.5% or less, about 0.25% or less, or about 0.1% or less of the relative binding affinity of the therapeutic anti-IgE antibody to the IgE.

In some embodiments, the therapeutic anti-IgE antibody is omalizumab, and the mutant antibody comprises one, two, or three amino acid mutations in the first CDR of the light chain and/or one, two, or three amino acid mutations in the third CDR of the heavy chain. In some embodiments, the therapeutic anti-IgE antibody is omalizumab, and the mutant antibody comprises the heavy chain variable region amino acid sequence from SEQ ID NO:2 and the light chain variable region amino acid sequence from SEQ ID NO:1 wherein amino acid Asp at position 34, positions 30 and 34, positions 32 and 34, or positions 30, 32, and 34 of SEQ ID NO:1 are substituted. In some embodiments, amino acid Asp at position 30, 32, and/or 34 of SEQ 1N NO:1 are substituted by Ala. In some embodiments, the mutant antibody comprises the heavy chain amino acid sequence of SEQ ID NO:2 and the light chain amino acid sequence of SEQ ID NO:1 with amino acid substitutions from Asp to Ala at positions 30, 32, and 34 of SEQ ID NO:1. Any of the anti-IgE antibodies described in Presta et al. (*J. Immunol.* 151:2623-2632, 1993) having the relative binding affinity and/or the potency to IgE of about 10% or less of the relative binding affinity or the potency of therapeutic antibody E25 may be used as mutant therapeutic antibody in the methods described herein.

Anti-drug antibodies may be generated and used as a control to screen for mutant antibodies. These control antibodies may bind with similar affinity or equally well to the mutant antibody and unmodified therapeutic anti-IgE antibody. In some embodiments, the control anti-drug antibody binds to Fab fragment of the anti-IgE antibody. In some embodiments, the control anti-drug antibody binds to one or more CDRs of the anti-IgE antibody. A binding assay described in Example 2 may be used to test and screen mutant antibodies using a control anti-drug antibody (such as a control antibody shown in FIG. 5). See FIG. 6A for assay methods.

The potency of a therapeutic anti-IgE antibody or a mutant therapeutic antibody is determined by measuring the ability of the therapeutic anti-IgE antibody or the mutant therapeutic antibody to bind to IgE in competition with the high affinity receptor (FcεRI) as compared to a reference control. Typical assay methods include immunoassays, such as ELISA, ECLA, and the like that include a capture agent bound to an assay surface to capture and immobilize the desired target molecule. Captured target molecules are detected with a detection agent that binds the target molecule and provides a detection label for quantification.

In some embodiments, the potency of a therapeutic anti-IgE antibody or a mutant therapeutic antibody is determined by an inhibition ELISA as shown in FIG. 3. Increasing concentrations of an anti-IgE antibody or a mutant antibody is incubated with labeled IgE. The mixture is added to a plate containing an immobilized FcεRIα polypeptide as a capture agent. The anti-IgE antibody or the mutant antibody that binds labeled IgE effectively inhibits the binding of the labeled IgE to the capture agent, reducing the detectable signal. Thus, an anti-IgE potency of the sample is inversely correlated with the signal detected.

FcεRIα polypeptides described herein can be used in such assays as capture agents that bind IgE. The amount of captured IgE can be compared with a control, for example a standard lot or other standard having a known amount of an anti-IgE antibody; and/or with a control lacking an anti-IgE antibody. A reduced signal detected from the labeled IgE is compared with the control and the amount of inhibition is correlated to the potency of the anti-IgE antibody or the mutant antibody.

Binding affinity (including relative binding affinity) of a mutant therapeutic antibody or a therapeutic anti-IgE antibody to an IgE may be measured using ELISA or BIAcore™ surface plasmon resonance (SPR) system (BIAcore, INC, Piscataway N.J.). Relative binding affinity is a comparison of the binding of the drug to its target compared with another drug. For example, using an ELISA assay, a therapeutic anti-IgE antibody or a mutant antibody, or a fragment thereof (such as a Fab) is immobilized to a surface, and purified IgE (such as human IgE) with increased concentration (such as from 0.1 ng/ml to 10,000 ng/ml) is then incubated with the immobilized therapeutic anti-IgE antibody or the mutant antibody. A detecting agent (such as a goat anti-human IgE antibody) labeled with HRP is allowed to bind to any IgE bound to the immobilized therapeutic anti-IgE antibody or mutant antibody. The signal generated by the HRP is measured. See, e.g., FIGS. 2A and 2B. The relative reduction in binding affinity of the mutant therapeutic antibody as compared to the therapeutic anti-IgE antibody is determined. Additionally, the relative binding affinity may be measured by immobilizing IgE (such as human IgE) directly to a surface (ELISA plate), incubating with varying concentrations of an anti-IgE therapeutic antibody or mutant antibody, and then detecting the bound anti-IgE therapeutic antibody or mutant antibody using an HRP-labeled anti-human IgG antibody. Alternatively, BIAcore assays may be used to measure the binding affinity of human IgE to the immobilized therapeutic anti-IgE antibody or the mutant antibody (such as Fab fragments).

Other properties of the therapeutic anti-IgE antibody and the mutant antibody, such as primary and tertiary structures and glycan levels, are tested using known method.

FcεRIα Polypeptides

An FcεRIα polypeptide can be used as a capture agent, a detecting agent and/or a blocking agent in the assays described herein. The term "FcεRI polypeptide" is used to describe a polypeptide that binds to the Fc region of an IgE or IgE Fc-region containing molecule, and a polypeptide that forms a receptor that binds to the Fc region of an IgE or IgE Fc-region containing molecule. FcεRI receptor may include an Fc receptor polypeptide α-chain and an Fc receptor polypeptide homo- or heterodimer of the ε-chain. FcεRI α-chains contain an extracellular domain ("ECD") that binds to the Fc domain-containing agent, for example an immunoglobulin (Ig). FcRs are reviewed in Ravetch and Kinet, 1991, *Annu. Rev. Immunol.* 9: 457-492; Capel et al., 1994, *Immunomethods* 4: 25-34; and de Haas et al., 1995 *J. Lab. Clin. Med.* 126: 330-341. The physiology and pathology of the high affinity IgE receptor (FcεRI) are reviewed in Kinet, 1999, *Annu. Rev. Immunol.* 17: 931-972.

In some embodiments, the FcεRI polypeptide may comprise Fc binding domain sequences (such as extracellular domain sequences) from a human or a non-human primate (such as cynomolgus monkey, rhesus monkey, chimpanzee) FcεRIα polypeptide. FcεRIα polypeptide may also include synthetic FcεRIα polypeptide, variants of FcεRIα polypeptide, fusion proteins comprising FcεRIα polypeptide, and chimeric proteins comprising FcεRIα polypeptide. In some embodiments, the FcεRIα polypeptide binds human IgE with similar affinity as wild type human or non-human primate FcεRIα and does not block the CDR epitopes of human IgE from binding to the therapeutic anti-IgE antibody.

The immature FcεRIα polypeptides contain native signal sequence, and mature polypeptides lack signal sequence. The FcεRIα polypeptides include immature FcεRIα polypeptides containing native signal sequence and mature polypeptides lacking signal sequence. In some embodiments, the FcεRIα polypeptides may include those having the amino acid sequence of SEQ ID NO: 3 (cynomolgus), SEQ ID NO: 4 (rhesus), SEQ ID NO: 5 (chimpanzee), or SEQ ID NO: 6 (human) as well as variants thereof having at least 90% (for example, 90%, 91%, 92%, 93%, 94%, 95%, 96%, 97%, 98%, 99%) sequence identity with the sequence of SEQ ID NO: 3, 4, 5, or 6.

FcεRIα IgE-Binding Fragment Polypeptides

In some embodiments, the FcεRIα polypeptide comprises an IgE binding fragment of FcεRIα. IgE-binding fragments of FcεRIα preferably retain high affinity for IgE. In one example, the IgE-binding fragment comprises an extracellular domain ("ECD") of a human or a non-human primate FcεRIα, and can be the ECD of SEQ ID NO: 3, 4, 5, or 6, or of a variant thereof having at least 90% sequence identity to SEQ ID NO: 3, 4, 5 or 6.

The amino acid sequences of cynomolgus, rhesus, chimpanzee, and human FcεRIα are shown in Table 1 below. Any of the non-human primate FcεRIα polypeptides described in WO 08/028,068 may be used.

TABLE 1

Primate FcεRIα Mature Sequences

| | | | | | | |
|---|---|---|---|---|---|---|
| +1 | 10 | 20 | 30 | 40 | 50 | |
| Cyno | VPQKPTVSLN | PPWNRIFKGE | NVTLTCNGSN | FFEVSSMKWF | HNGSLSEVAN | (SEQ ID NO: 3) |
| Rhesus | VPQKPTVSLN | PPWNRIFKGE | NVTLTCNGSN | FFEVSSMKWF | HNGSLSEVAN | (SEQ ID NO: 4) |
| Chimp | VPQKPKVSLN | PPWNRIFKGE | NVTLTCNGNN | FFEVSSTKWF | HNGSLSEETN | (SEQ ID NO: 5) |
| Human | VPQKPKVSLN | PPWNRIFKGE | NVTLTCNGNN | FFEVSSTKWF | HNGSLSEETN | (SEQ ID NO: 6) |
| | 60 | 70 | 80 | 90 | 100 | |
| Cyno | SSLNIVNADF | EDSGEYKCQH | QQFDDSEPVH | LEVFSDWLLL | QASAEVVMEG | |
| Rhesus | SSLNIVNADF | EDSGEYKCQH | QQFDDSEPVH | LEVFSDWLLL | QASAEVVMEG | |
| Chimp | SSLNIVNAKF | EDSGEYKCQH | QQVNESEPVY | LEVFSDWLLL | QASAEVVMEG | |
| Human | SSLNIVNAKF | EDSGEYKCQH | QQVNESEPVY | LEVFSDWLLL | QASAEVVMEG | |
| | 110 | 120 | 130 | 140 | 150 | |
| Cyno | QPLFLRCHSW | RNWDVYKVIY | YKDGEALKYW | YENHNISITN | TTVEDSGTYY | |
| Rhesus | QPLFLRCHSW | RNWDVYKVIY | YKDGEALKYW | YENHNISITN | ATVEDSGTYY | |
| Chimp | QPLFLRCHGW | RNWDVYKVIY | YKDGEALKYW | YENHNISITN | ATVEDSGTYY | |
| Human | QPLFLRCHGW | RNWDVYKVIY | YKDGEALKYW | YENHNISITN | ATVEDSGTYY | |
| | 160 | 170 | * 180 | 190 | 200 | |
| Cyno | CTGKLWQLDC | ESEPLNITVI | KAQHDKYWLQ | FLIPLLVAIL | FAVDTGLFIS | |
| Rhesus | CTGKLWQLDC | ESEPLNITVI | KAQHDKYWLQ | FLIPLLVAIL | FAVDTGLFIS | |
| Chimp | CTGKVWQLDY | ESEPLNITVI | KAPREKYWLQ | FFIPLLVAIL | FAVDTGLFIS | |
| Human | CTGKVWQLDY | ESEPLNITVI | KAPREKYWLQ | FFIPLLVVIL | FAVDTGLFIS | |
| | 210 | 220 | 230 | 232 | | |
| Cyno | TQQQVTFLLK | IKRTRKGFKL | LNPHPKPNPK | SN | | |
| Rhesus | TQQQVTFLLK | IKRTRKGFKL | LNPHPKPNPK | SN | | |
| Chimp | TQQQVTFLLK | IKRTRKGFRL | LTPHPKPNPK | NN | | |
| Human | TQQQVTFLLK | IKRTRKGFRL | LNPHPKPNPK | NN** | | |

*ECD-residues V1-K176

**U.S. Pat. No. 6,602,983

The FcεRIα ECD can extend, for example, from residue V1 to K171, A172, P173, H/R174, D/E175, or K176 of the FcεRIα polypeptides, numbered as shown in Table 1. In some embodiments, the FcεRI polypeptide comprises any of the following FcεRIα ECD fragments: V1-K171, V1-A172, V1-Q/P173, V1-H/R174, V1-D/E175, or V1-K176. Exemplary FcεRIα ECD polypeptides thus include those polypeptides comprising residues V1 to K171, V1 to A172, V1 to P173, V1 to H/R174, V1 to D/E175, or V1 to K176 of SEQ ID NO: 3, 4, 5, or 6, and of variants thereof having at least 90% (for example, 90%, 91%, 92%, 93%, 94%, 95%, 96%, 97%, 98%, 99%) identity with SEQ ID NO: 3, 4, 5, or 6.

Additional fragments include truncations and deletion mutants of the ECDs that retain high affinity binding to IgE.

FcεRIα Variant Polypeptides

In some embodiments, the FcεRIα polypeptide comprises a variant FcεRIα polypeptide. Variant FcεRIα polypeptides are those having at least one amino acid substitution, deletion, or insertion as compared to a native polypeptide. FcεRIα variants can have one or more conservative amino acid substitution (as defined herein), replacing a target residue with a corresponding residue of the same general character, for example, a Lys for an Arg. Such amino acid substitutions can be made without altering the general function of the polypeptide. The FcεRIα variant polypeptide can also include non-conservative substitutions.

A variant FcεRIα polypeptide may have one or more substitution replacing an amino acid of a first species FcεRIα with a corresponding amino acid of a second species FcεRIα. For example, the encoded polypeptide can contain one or more (but no more than 14) amino acid substitutions at positions 29, 37, 48, 49, 59, 73, 74, 75, 80, 141, 155, 160, 173, 174, or 175, as shown in Table 1. The one or more substitutions can include, for example, one or more (and fewer than 14) of the following amino acid substitutions:

S29N M37T V48E A49T D59K
F73V D74N D75E H80V T141A
L155V C160Y Q173P H174R D175E

Structural information derived from the crystal structure of human FcεRI complexed with the Fc domain of human IgE indicates that Tyr 160 is located near the receptor:ligand interface. Because a Cys at this interface may impede binding, the FcεRIα polypeptides may be mutated to replace Cys160 with tyrosine to improve binding of cynomolgus and rhesus FcεRIα to human IgE. In some embodiments, the FcεRIα polypeptide comprises an FcεRIα polypeptide that has been mutated to include the Cys160 to Tyrosine mutation. For example, the mutated cyno sequence is shown below.

```
pRKgD cynoFcεRI.6xHisTyr160
                                                    (SEQ ID NO: 11)
    -55
    MGGAA ARLGAVILFV VIVGLHGVRG KYALADASLK MADPNRFRGK DLPVLDQLLE

+1  VPQKPTVSLN PPWNRIFKGE NVTLTCNGSN FFEVSSMKWF HNGSLSEVAN SSLNIVNADF

EDSGEYKCQH QQFDDSEPVH LEVFSDWLLL QASAEVVMEG QPLFLRCHSW RNWDVYKVIY

YKDGEALKYW YENHNISITN TTVDSGTYYC TGKLWQLDYE SEPLNITVIK AQHDK

HHHHHH
```

Chimeric FcεRIα Polypeptides

In some embodiments, the FcεRIα polypeptide is a chimeric polypeptide, for example, a chimeric polypeptide formed of two or more portions of different FcεRIα polypeptides. For example, a chimeric FcεRIα polypeptide can be formed of two or more portions derived from two or more of SEQ ID NO: 3, 4, 5, and 6. An exemplary chimeric polypeptide is the cynomolgus/rhesus chimeric polypeptide comprising residues 1-141 of the rhesus FcεRIα ECD and residues 142-171 of the cyno FcεRIα ECD, and having the amino acid sequence of SEQ ID NO: 12 (see right below). Additional chimeric polypeptides contemplated include human/cyno, human/rhesus, human/chimpanzee, cyno/chimpanzee, rhesus/chimpanzee, and the like chimeras, each comprising a portion of the named species FcεRIα ECD.

```
rhesusSScynoFcεRI.6xhis tyr160
                                                    (SEQ ID NO: 12)
         -25                          +1
         MAPAM ESPTLLCVAL LFFAPDGVLA VPQKPTVSLN PPWNRIFKGE NVTLTCNGSN

FFEVSSMKWF HNGSLSEVAN SSLNIVNADF EDSGEYKCQH QQFDDSEPVH LEVFSDWLLL

QASAEVVMEG QPLFLRCHSW RNWDVYKVIY YKDGEALKYW YENHNISITN TTVEDSGTYY

CTGKLWQLDY ESEPLNITVI KAQHDK  HHHHHH
```

Fusion Proteins

In some embodiments, the FcεRIα polypeptide is a fusion protein, for example, an FcεRIα polypeptide fused to one or more heterologous polypeptide. Such fusion proteins can comprise at least an FcεRIα IgE binding fragment, for example at least an FcεRIα ECD, fused at the carboxy or amino terminus, to a heterologous polypeptide. The heterologous polypeptide can be any polypeptide, and generally is a polypeptide that confers a specific property to the fusion protein.

Heterologous polypeptides can provide for secretion, improved stability, or facilitate purification of the FcεRIα polypeptides. Non-limiting examples of such peptide tags include the 6-His tag, Gly/His6/GST tag, thioredoxin tag, hemaglutinin tag, Glylh156 tag, and OmpA signal sequence tag. For example, an extracellular domain of an FcεRIα polypeptide can be fused to a His tag, for example (His)$_6$, including a Gly(His)$_6$-gst tag. The Gly(His)$_6$-gst tag provides for ease of purification of polypeptides encoded by the nucleic acid.

Using the ECD of each species as described above, different forms of FcεRIα polypeptide may be constructed and expressed in mammalian cells, for example, monomeric forms containing an extracellular domain (residues 1-176) of the receptor, six C-terminal histidine residues, and a signal sequence. For example, FcεRIα polypeptide may comprise a monomeric form containing a native signal sequence at the N-terminus for the ECD, and a HIS6 tag:

cyno FcεR1 (1-176) his monomer
(SEQ ID NO: 13)
<u>MAPAM ESPTLLCVAL LFFAPDGVLA</u> VPQKPTVSLN PPWNRIFKGE NVTLTCNGSN

FFEVSSMKWF HNGSLSEVAN SSLNIVNADF EDSGEYKCQH QQFDDSEPVH LEVFSDWLLL

QASAEVVMEG QPLFLRCHSW RNWDVYKVIY YKDGEALKYW YENHNISITN TTVEDSGTYY

CTGKLWQLDY ESEPLNITVI KAQHDK(176)HHHHHH

FcεRIα polypeptide may also comprise the ECD fused to the signal sequence and first 27 amino acids of the herpes simplex virus (HSV) gD protein shown below.

MGGAAARLGAVILFVVIVGLHGVRGKYALADASLKMADPNRFRGKDLPVLDQLLE(SEQ ID NO: 14)

In some embodiments, an FcεRIα polypeptide can be any of the three specific fusion proteins, each containing an HSV gD signal sequence (underlined below) fused to an FcεRIα ECD and a 6×His tag:
  gDcyno FcεRIα 1-176 6×his (SEQ ID NO: 15),
  gDrhesus FcεRIα 1-176 6×his (SEQ ID NO: 16), and
  gDchimp FcεRIα 1-176 6×his (SEQ ID NO: 17).

The FcεRIα polypeptides can also be fused to the immunoglobulin constant domain of an antibody to form immunoadhesin molecules. For example, a fusion polypeptide comprises an extracellular domain of an FcεRIα polypeptide and an Fc portion of an IgG, which may be used in any of the methods provided herein. In some embodiments, the fusion polypeptide FcεRIα-IgG comprises the following sequence:

gDcynoFcεRIα 1-176 6XHis
(SEQ ID NO: 15)
<u>MGGAA ARLGAVILFV VIVGLHGVRG KYALADASLK MADPNRFRGK DLPVLDQLLE</u>

+1  VPQKPTVSLN PPWNRIFKGE NVTLTCNGSN FFEVSSMKWF HNGSLSEVAN

SSLNIVNADF EDSGEYKCQH QQFDDSEPVH LEVFSDWLLL QASAEVVMEG

QPLFLRCHSW RNWDVYKVIY YKDGEALKYW YENHNISITN TTVEDSGTYY

CTGKLWQLDC ESEPLNITVI KAQHDK HHHHHH gDrhesus FcεRIα 1-176 6XHis
(SEQ ID NO: 16)
<u>MGGAA ARLGAVILFV VIVGLHGVRG KYALADASLK MADPNRFRGK DLPVLDQLLE</u>

+1  VPQKPTVSLN PPWNRIFKGE NVTLTCNGSN FFEVSSMKWF HNGSLSEVAN

SSLNIVNADF EDSGEYKCQH QQFDDSEPVH LEVFSDWLLL QASAEVVMEG

QPLFLRCHSW RNWDVYKVIY YKDGEALKYW YENHNISITN ATVEDSGTYY

CTGKLWQLDC ESEPLNITVI KAQHDKYWLQ FLIPLLVAIL FAVDTGLFIS

TQQQVTFLLK IKRTRKGFKL LNPHPKPNPK SN HHHHHH gDchimp FcεRIα 1-176 6XHis
(SEQ ID NO: 17)
<u>MGGAA ARLGAVILFV VIVGLHGVRG KYALADASLK MADPNRFRGK DLPVLDQLLE</u>

+1  VPQKPKVSLN PPWNRIFKGE NVTLTCNGNN FFEVSSTKWF HNGSLSEETN

SSLNIVNAKF EDSGEYKCQH QQVNESEPVY LEVFSDWLLL QASAEVVMEG

QPLFLRCHGW RNWDVYKVIY YKDGEALKYW YENHNISITN ATVEDSGTYY

CTGKVWQLDY ESEPLNITVI KAPREKYWLQ FFIPLLVAIL FAVDTGLFIS

TQQQVTFLLK IKRTRKGFRL LTPHPKPNPK NN HHHHHH

```
                                                       (SEQ ID NO: 18)
¹VPQKPKVSLN PPWNRIFKGE NVTLTCNGNN FFEVSSTKWF HNGSLSEETN SSLNIVNAKF⁶⁰

⁶¹EDSGEYKCQH QQVNESEPVY LEVFSDWLLL QASAEVVMEG QPLFLRCHGW RNWDVYKVIY¹²⁰

¹²¹YKDGEALKYW YENHNISITN ATVEDSGTYY CTGKLWQLDY ESEPLNITVI KAPREKYWLD¹⁸⁰

¹⁸¹KTHTCPPCPA PELLGGPSVF LFPPKPKDTL MISRTPEVTC VVVDVSHEDP EVKFNWYVDG²⁴⁰

²⁴¹VEVHNAKTKP REEQYNSTYR VVSVLTVLHQ DWLNGKEYKC KVSNKALPAP IEKTISKAKG³⁰⁰

³⁰¹QPREPQVYTL PPSREEMTKN QVSLTCLVKG FYPSDIAVEW ESNGQPENNY KTTPPVLDSD³⁶⁰

³⁶¹GSFFLYSKLT VDKSRWQQGN VFSCSVMHEA LHNHYTQKSL SLSPGK⁴⁰⁶
```

In some embodiments, the FcεRIα polypeptide is a fusion protein comprising an FcεRIα polypeptide fused to an Fc domain of IgG which forms a dimeric form of FcεRIα. Cysteine residues present in the IgG Fc domain permit dimerization of the fusion polypeptide. For example, the FcεRIα-encoding nucleic acid fragment may be fused into the Fc domain of IgG shown below:

```
Fc domain of IgG
                                                    (SEQ ID NO: 19)
VTDKTHTCPP CPAPELLGG  PSVFLFPPKP KDTLMISRTP EVTCVVVDVS HEDPEVKFNW

YVDGVEVHNA KTKPREEQYN STYRVVSVLT VLHQDWLNGK EYKCKVSNKA LPAPIEKTIS

KAKGQPREPQ VYTLPPSREE MTKNQVSLTC LVKGFYPSDI AVEWESNGQP ENNYKTTPPV

LDSDGSFFLY SKLTVDKSRW QQGNVFSCSV MHEALHNHYT QKSLSLSPGK
```

The FcεRIα polypeptide may contain a native rhesus signal sequence (SS), a portion of the rhesus FcεRIα ECD (residues V1-A141) and a portion of the cynomolgus FcεRIα ECD (residues T142-K171), fused to the Fc domain of immunoglobulin G protein. The cysteine residues of the IgG domain permit disulfide bonds to form an FcεRIα polypeptide dimer. In some embodiments, the FcεRI polypeptide comprises the FcεRIα-IgG fusion protein with the sequence shown below:

```
rhesus (1-141)/cyno (142-171) FcεRIα-IgG fusion protein (1-171)
                                                    (SEQ ID NO: 20)
    -25                 +1
    MAPAM ESPTLLCVAL LFFAPDGVLA VPQKPTVSLN PPWNRIFKGE NVTLTCNGSN

FFEVSSMKWF HNGSLSEVAN SSLNIVNADF EDSGEYKCQH QQFDDSEPVH LEVFSDWLLL

QASAEVVMEG QPLFLRCHSW RNWDVYKVIY YKDGEALKYW YENHNISITN ATVEDSGTYY

CTGKLWQLDY ESEPLNITVI KVTDKTHTCP PCPAPELLGG PSVFLFPPKP KDTLMISRTP

EVTCVVVDVS HEDPEVKFNW YVDGVEVHNA KTKPREEQYN STYRVVSVLT VLHQDWLNGK

EYKCKVSNKA LPAPIEKTIS KAKGQPREPQ VYTLPPSREE MTKNQVSLTC LVKGFYPSDI

AVEWESNGQP ENNYKTTPPV LDSDGSFFLY SKLTVDKSRW QQGNVFSCSV MHEALHNHYT

QKSLSLSPGK
```

Additional chimeric rhesus/cyno FcεRIα-IgG fusion proteins include the fusion proteins made by varying the length of the chimeric FcεRIα polypeptide from 1-171 to 1-178 with increasing lengths of the sequence 171KAQHDKYW178. These include:

rhesus/cyno FcεRIα-IgG fusion protein (1-172) (SEQ ID NO: 21)

rhesus/cyno FcεRIα-IgG fusion protein (1-173) (SEQ ID NO: 22)

rhesus/cyno FcεRIα-IgG fusion protein (1-174) (SEQ ID NO: 23)

rhesus/cyno FcεRIα-IgG fusion protein (1-175) (SEQ ID NO: 24)

rhesus/cyno FcεRIα-IgG fusion protein (1-176) (SEQ ID NO: 25)

rhesus/cyno FcεRIα-IgG fusion protein (1-177) (SEQ ID NO: 26)

rhesus/cyno FcεRIα-IgG fusion protein (1-178) (SEQ ID NO: 27)

For example, an FcεRIα polypeptide may be rhesus/cyno FcεRIα-IgG fusion protein (1-178) with the sequence shown below:

```
rhesus/cyno FcεRIα-IgG fusion protein (1-178)
                                                (SEQ ID NO: 27)
 -25 MAPAM ESPTLLCVAL LFFAPDGVLA VPQKPTVSLN PPWNRIFKGE NVTLTCNGSN
```

```
FFEVSSMKWF HNGSLSEVAN SSLNIVNADF EDSGEYKCQH QQFDDSEPVH LEVFSDWLLL

QASAEVVMEG QPLFLRCHSW RNWDVYKVIY YKDGEALKYW YENHNISITN ATVEDSGTYY

CTGKLWQLDY ESEPLNITVI KAQHDKYWVT DKTHTCPPCP APELLGGPSV FLFPPKPKDT

LMISRTPEVT CVVVDVSHED PEVKFNWYVD GVEVHNAKTK PREEQYNSTY RVVSVLTVLH

QDWLNGKEYK CKVSNKALPA PIEKTISKAK GQPREPQVYT LPPSREEMTK NQVSLTCLVK

GFYPSDIAVE WESNGQPENN YKTTPPVLDS DGSFFLYSKL TVDKSRWQQG NVFSCSVMHE

ALHNHYTQKS LSLSPGK
```

FcεRIα polypeptides include polypeptides made by various combinations of cyno, rhesus, chimp, and human FcεRIα polypeptides which produces a variety of chimeric FcεRIα polypeptides. For example, an FcεRIα polypeptide may comprise cyno/human FcεRIα-IgG (1-178) shown below:

```
cyno/HumanFcεRIα-IgG (1-178)
                                                (SEQ ID NO: 28)
MAPAM  ESPTLLCVAL  LFFAPDGVLA  VPQKPTVSLN  PPWNRIFKGE  NVTLTCNGSN

FFEVSSMKWF HNGSLSEVAN SSLNIVNADF EDSGEYKCQH QQFDDSEPVH LEVFSDWLLL

QASAEVVMEG QPLFLRCHSW RNWDVYKVIY YKDGEALKYW YENHNISITN ATVEDSGTYY

CTGKVWQLDY ESEPLNITVI KAPREKYWVT DKTHTCPPCP APELLGGPSV FLFPPKPKDT

LMISRTPEVT CVVVDVSHED PEVKFNWYVD GVEVHNAKTK PREEQYNSTY RVVSVLTVLH

QDWLNGKEYK CKVSNKALPA PIEKTISKAK GQPREPQVYT LPPSREEMTK NQVSLTCLVK

GFYPSDIAVE WESNGQPENN YKTTPPVLDS DGSFFLYSKL TVDKSRWQQG NVFSCSVMHE

ALHNHYTQKS LSLSPGK
```

In some embodiments, the FcεRIα polypeptide is labeled (such as a biotin, a digoxigenin, a ruthenium, a radiologic, a photoluminescent, a chemiluminescent, a fluorescent, or an electrochemiluminescent label).

The inventions also provide polynucleotides encoding any of FcεRIα polypeptides described herein. The inventions further provide variant polynucleotide sequences that can be at least about 90%, 91%, 92%, 93%, 94%, 95%, 96%, 97%, 98%, or 99% identical, to a nucleic acid sequence encoding a full length native sequence, a mature sequence lacking a signal sequence, or an extracellular domain of the polypeptide of SEQ ID NOs: 3, 4, 5, or 6, and are less than 100% identical to a nucleic acid sequence encoding a full length native sequence, mature sequence lacking a signal sequence, or an extracellular domain of a native sequence.

Alterations of the FcεRIα nucleic acid and amino acid sequences can be accomplished by a number of known techniques. For example, mutations can be introduced at particular locations by procedures known to the skilled artisan, such as oligonucleotide-directed mutagenesis, for example, described by Walder et al., 1986, Gene, 42:133; Bauer et al., 1985, Gene 37:73; Craik, 1985, BioTechniques, 12-19; Smith et al., 1981, Genetic Engineering: Principles and Methods, Plenum Press; U.S. Pat. No. 4,518,584, and U.S. Pat. No. 4,737,462.

Methods of making nucleotides encoding FcεRI polypeptides and expression of FcεRI polypeptides in mammalian cells are known to one of ordinary skill in the art. For example, plasmids encoding the constructed forms of FcεRI polypeptides described above can be transfected into 293S human embryonic kidney cells using either calcium phosphate precipitation or Fugene® (Roche, Indianapolis, Ind.) transfection methods. Supernatants from transfected cell cultures are collected after several days of growth and FcεRI polypeptide can be purified by affinity chromatography using column matrix immobilized antibodies directed against the HSV gD tag (MAb5B6 coupled to controlled pore glass), or using metal chelating resins directed against the 6× histidine fusion tag (Ni-NTA-Agarose, Qiagen, Valencia, Calif.).

Polypeptides and proteins (such as, anti-IgE antibodies, mutant antibodies, control anti-drug antibodies, FcεRI polypeptides, etc.) described herein may be produced and isolated or purified using methods known in the art. "Purified" means that a molecule is present in a sample at a concentration of at least 95% by weight, or at least 96%, 97%, 98%, or 99% by weight of the sample in which it is contained. Any recombinant DNA or RNA method can be used to create the host cell that expresses the target polypeptides of the invention, including, but not limited to, transfection, transformation or transduction. Methods and vectors for genetically engineering host cells with the polynucleotides of the present invention, including fragments and variants thereof, are well known in the art, and can be found, for example, in Current Protocols in Molecular Biology, Ausubel et al., eds. (Wiley & Sons, New York, 1988, and updates). Exemplary vectors and host cells are described in the Examples below.

Host cells are genetically engineered to express the polypeptides described herein. The vectors include DNA encoding any of the polypeptides described herein, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein.

Such polypeptides may be included to allow, for example, secretion, improved stability, or facilitated purification of the polypeptide. A polynucleotide sequence encoding an appropriate signal peptide can be incorporated into expression vectors. A DNA sequence for a signal peptide (secretory leader) may be fused in-frame to the target sequence so that target protein is translated as a fusion protein comprising the signal peptide. The DNA sequence for a signal peptide can replace the native nucleic acid encoding a signal peptide or in addition to the nucleic acid sequence encoding the native sequence signal peptide. A signal peptide that is functional in the intended host cell promotes extracellular secretion of the polypeptide. Preferably, the signal sequence will be cleaved from the target polypeptide upon secretion from the cell. Non-limiting examples of signal sequences that can be used in practicing the invention include the yeast I-factor and the honeybee melatin leader in Sf9 insect cells.

Selection of suitable vectors to be used for the cloning of polynucleotide molecules encoding the polypeptides will depend upon the host cell in which the vector will be transformed, and, where applicable, the host cell from which the target polypeptide is to be expressed. Suitable host cells for expression of the polypeptides include prokaryotes, yeast, and higher eukaryotic cells.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

The polypeptides or proteins produced from the host cells may be further purified using known methods.

Methods for Detecting Anti-Drug Antibodies of IgE Isotype that Bind to a Therapeutic Anti-IgE Antibody In one aspect, the invention provides methods for detecting anti-drug antibodies of IgE isotype that bind to a therapeutic anti-IgE antibody in a sample from an individual, comprising the steps of: (a) contacting a sample that may contain the anti-drug antibodies with a mutant therapeutic antibody comprising at least one amino acid mutation from the therapeutic anti-IgE antibody, wherein the relative binding affinity of the mutant therapeutic antibody to an IgE (such as a human IgE) is about 10% or less of the relative binding affinity of the therapeutic anti-IgE antibody to the IgE; and (b) detecting binding of the anti-drug antibodies to the mutant therapeutic antibody.

In another aspect, the invention provides methods for detecting anti-drug antibodies of IgE isotype that bind to a therapeutic anti-IgE antibody in a sample from an individual, comprising the steps of: (a) contacting a sample that may contain the anti-drug antibodies with a mutant therapeutic antibody comprising at least one amino acid mutation from the therapeutic anti-IgE antibody, wherein the potency of the mutant therapeutic antibody is about 10% or less of the potency of the therapeutic anti-IgE antibody; and (b) detecting binding of the anti-drug antibodies to the mutant therapeutic antibody.

Methods known in the art may be used to detect binding between the anti-drug antibodies and the mutant therapeutic antibody. ELISA, BIAcore®, Immunocap®, RIA (RadioImmunoAssay) assays may be used. The assays may be homogeneous, semi-homogeneous, or non-homogeneous. For example, most ELISAs utilize antibodies and/or ligands for capture and detection of a target protein. These ELISAs can utilize either homogeneous, semi-homogeneous, or non-homogeneous assay formats to maximize sensitivity or reduce matrix interference.

Homogeneous assays utilize a format where both the capture agent and detection agent (or ligands) are pre-incubated simultaneously with the matrix sample containing the target protein in a liquid-phase reaction. The capture agent-target protein-detection agent complex is then captured on a solid-phase (such as a streptavidin-coated ELISA plate), washed, and quantitated by detecting the amount of the detection agent captured to the surface (e.g., by the addition of an appropriate substrate solution if the detection agent is labeled with an enzyme). Semi-homogeneous assays utilize a format where the capture agent alone is pre-incubated with the matrix sample in a liquid-phase reaction. This capture agent-target protein complex is then captured on a solid phase, washed, then incubated with a detection agent, washed, and quantitated. Non-homogeneous assays do not utilize any liquid-phase pre-incubation step, but instead utilize sequential steps. The capture agent is captured to the solid-phase, washed, the matrix sample containing the target protein is then added and bound by the capture agent, washed, bound by the detection reagent, washed, and finally quantitated.

For example, in a non-homogeneous assay, a mutant therapeutic antibody described herein is immobilized to a surface and used as a capture agent for binding to the anti-drug IgE antibodies. The mutant therapeutic antibody may be directly or indirectly immobilized to the surface. In some embodiments, the mutant therapeutic antibody is conjugated to a label and is captured to the surface through a capture agent that specifically binds to the label, wherein the capture agent is immobilized to the surface. The directly or indirectly immobilized mutant therapeutic antibody is incubated with a sample from an individual that may contain anti-drug antibodies of IgE isotype. Since the mutant antibody is designed to have reduced binding affinity or potency to an IgE, the amount of the IgE antibodies bound to the mutant therapeutic antibody correlates with the anti-drug antibodies in the sample. Binding of the anti-drug IgE antibodies to the immobilized mutant antibody is detected using a detection agent (such as an FcεRI polypeptide that binds to the Fc region of an IgE). An example of such assays is shown in FIG. 7.

Figure 11:
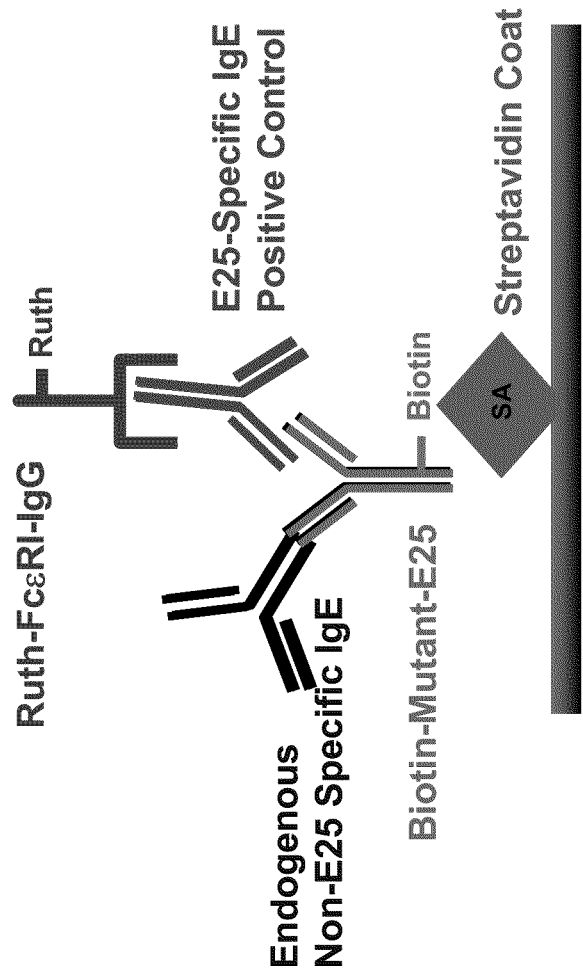
FIG. 11 is a diagrammatic representation of an assay for detecting E25-specific antibodies of IgE isotype using a semi-homogenous MSD-ECLA format.
Figure 12:
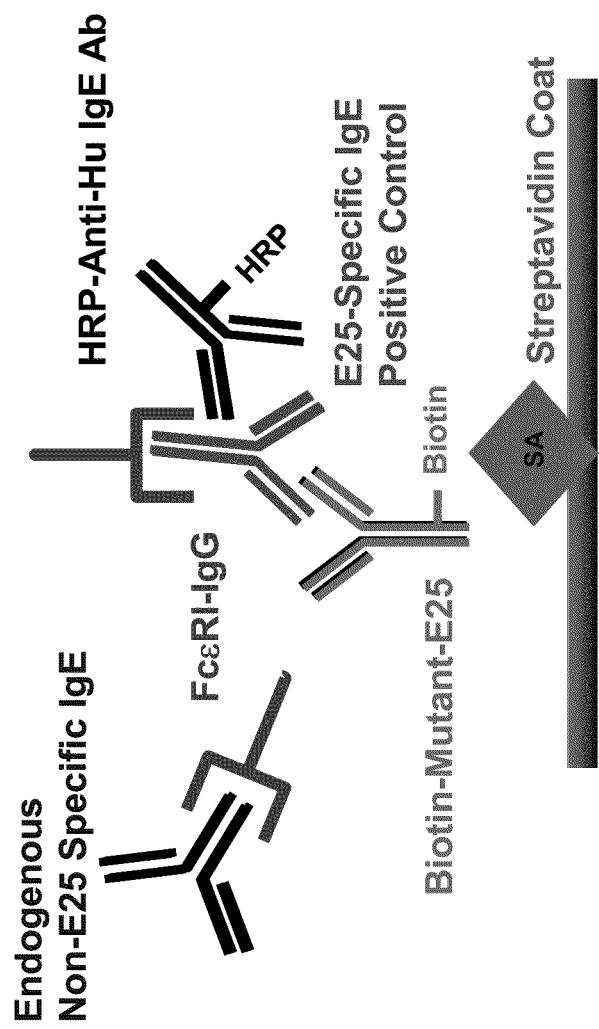
FIG. 12 is a diagrammatic representation of an assay for detecting E25-specific antibodies of IgE isotype using a "blocking" homogenous ELISA format.

Semi-homogenous assays may also be used for detecting anti-drug antibodies of IgE isotype in a sample. In some embodiments, the detection comprises the steps: 1) preincubating a sample from an individual that may contain anti-drug antibodies of IgE isotype with a labeled mutant therapeutic antibody; 2) incubating the preincubated sample with an immobilized molecule (such as streptavidin) that binds to the label on the mutant therapeutic antibody; and 3) detecting binding of the anti-drug antibodies of IgE isotype to the mutant therapeutic antibody using a detection agent (such as an FcεRI polypeptide that binds to the Fc region of an IgE). Washing steps may be included between the incubation steps to remove molecules unbound to the solid phase. Examples of such assays are shown in FIGS. 11 and 12.

"Blocking" homogenous assays may also be used for detecting anti-drug antibodies of IgE isotype in a sample. For example, the invention provides methods for detecting an anti-drug antibody of IgE isotype that binds to a therapeutic anti-IgE antibody in a sample, comprising the steps of: (a) preincubating a sample that may contain the anti-drug antibody with (i) the a mutant therapeutic anti-IgE antibody, and (ii) an FcεRIα polypeptide that binds to an Fc region of an IgE (such as an FcεRIα polypeptide comprising an extracellular domain of an FcεRIα subunit); (b) capturing the mutant therapeutic antibody in step (a) to a surface; and (c) detecting binding of the anti-drug antibody to the mutant therapeutic antibody.

"Blocking" semi-homogenous assays may also be used for detecting anti-drug antibodies of IgE isotype in a sample from an individual. For example, the invention provides methods for detecting an anti-drug antibody of IgE isotype that binds to a therapeutic anti-IgE antibody in a sample, comprising the steps of: (a) preincubating a sample that may contain the anti-drug antibody with an FcεRIα polypeptide that binds to an Fc region of an IgE, (b) incubating the preincubated sample from step (a) with the therapeutic anti-IgE antibody or a mutant thereof; and (c) detecting binding of the anti-drug antibody to the therapeutic anti-IgE antibody or the mutant antibody. The mutant therapeutic antibody may be captured to a surface before or after incubating with the preincubated sample.

In some embodiments, the sample is preincubated with excess amount of the FcεRIα polypeptide in the blocking assays. As used therein, "excess" amount of FcεRIα polypeptide means that the amount of the FcεRIα polypeptide added is higher than the highest level of baseline total IgE expected in a sample. For example, the baseline total IgE may be from 30 IU/mL to 700 IU/mL for patients with 30-150 kg body weight. In some embodiments, the amount of the FcεRIα polypeptide added is at least about 2-fold, at least about 3-fold, at least about 4-fold, at least about 5-fold, at least about 6-fold, at least about 7-fold, at least about 8-fold, at least about 9-fold, or at least 10-fold of the amount of the total IgE in the sample. In some embodiments, the mutant therapeutic antibody comprises at least one amino acid mutation from the therapeutic anti-IgE antibody, wherein the relative binding affinity of the mutant therapeutic antibody to an IgE is reduced as compared to the relative binding affinity of the therapeutic anti-IgE antibody to the IgE. In some embodiments, the relative binding affinity of the mutant therapeutic antibody to an IgE is about 10% or less of the relative binding affinity of the therapeutic anti-IgE antibody to the IgE. Any of the mutant therapeutic antibodies described herein may be used.

Figure 13:
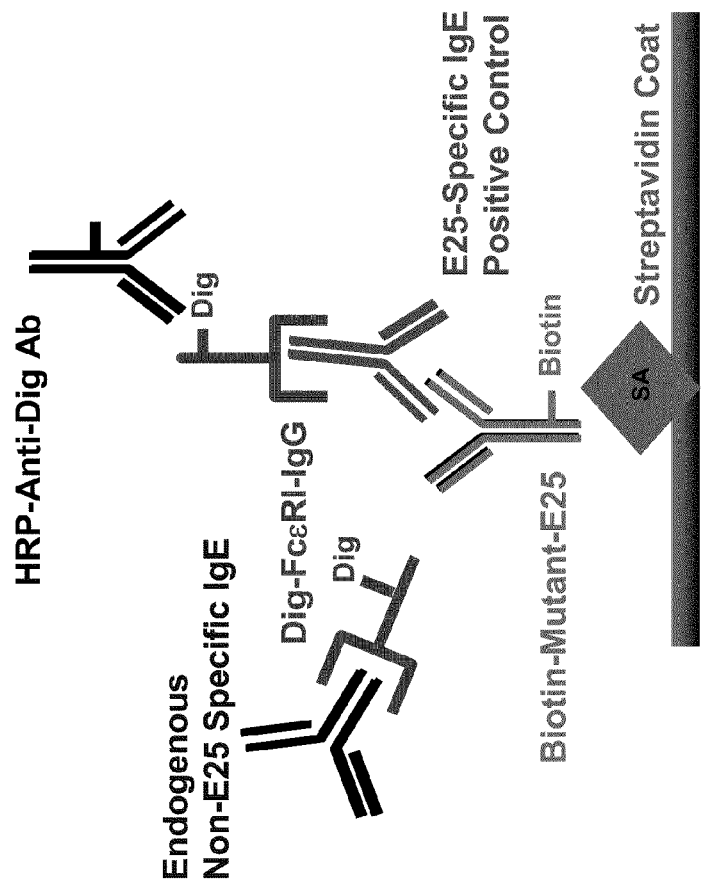
FIG. 13 is a diagrammatic representation of an assay for detecting E25-specific antibodies of IgE isotype using a "blocking" homogenous ELISA format.
Figure 14:
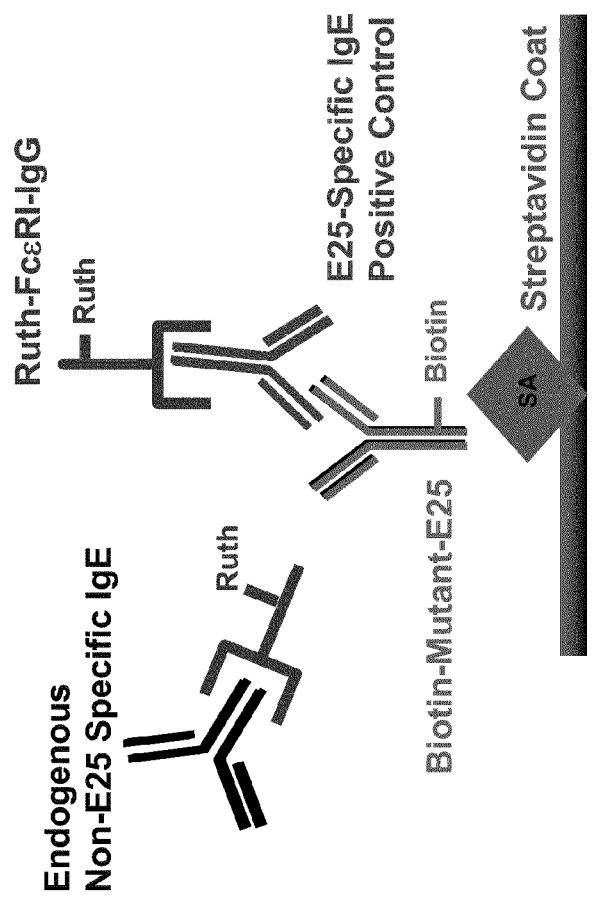
FIG. 14 is a diagrammatic representation of an assay for detecting E25-specific antibodies of IgE amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

In some embodiments, the method comprises the steps: 1) preincubating a sample from an individual that may contain anti-drug antibodies of IgE isotype with a labeled mutant therapeutic antibody in the presence of at least about 10-fold excess of either an unlabeled or labeled FcεRIα polypeptide; 2) incubating the preincubated sample to an immobilized molecule (such as streptavidin) that binds to the label (such as biotin) on the mutant therapeutic antibody; and 3) detecting binding of the anti-drug antibodies of IgE isotype to the mutant therapeutic antibody using a detection agent (such as a labeled anti-human IgE antibody or a labeled antibody specific for the label on the FcεRI polypeptide). Washing steps are included between the incubation steps to remove molecules unbound to the solid phase (such as endogenous non-drug specific IgE). Examples of such assays are shown in FIGS. 12, 13 and 14.

Figure 15:
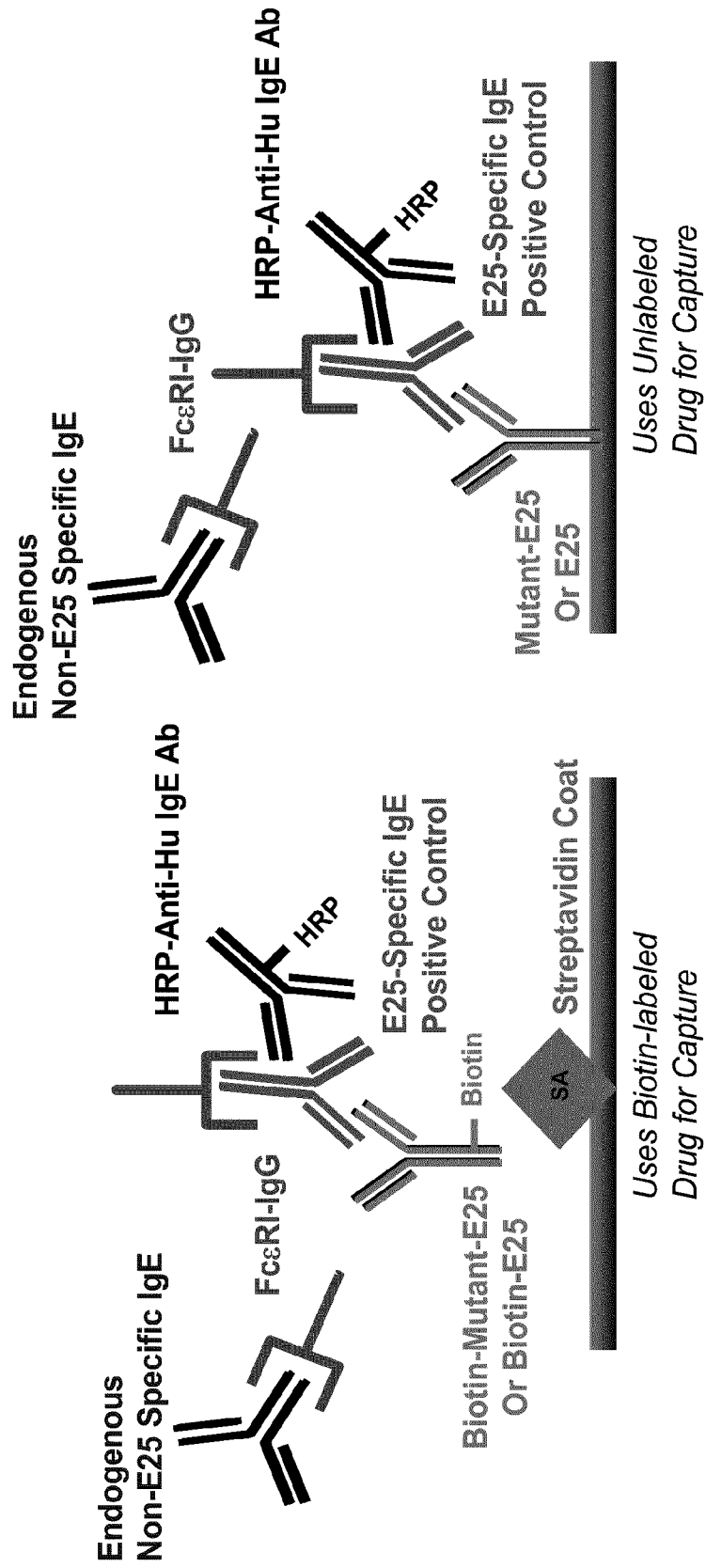
Figure 16:
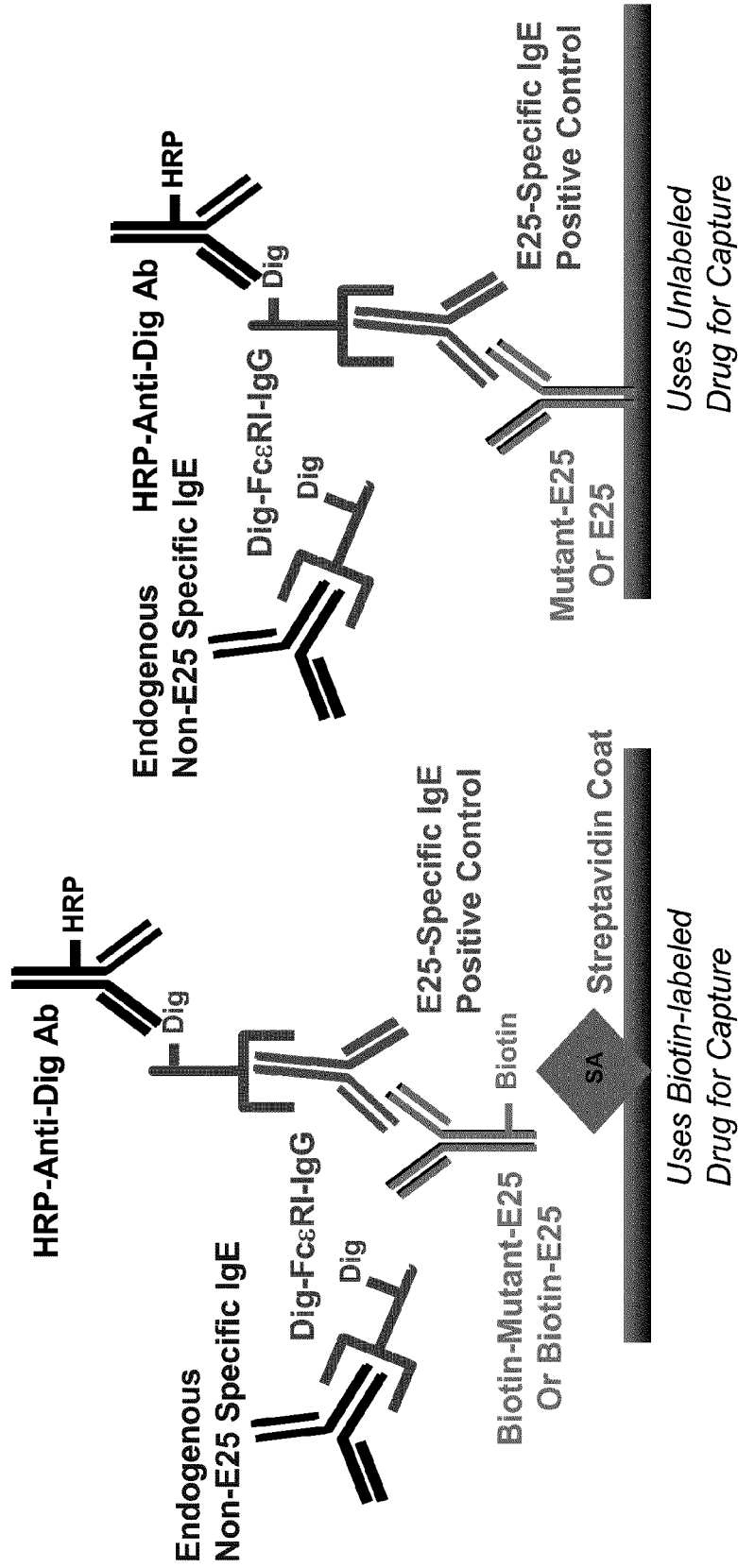
Figure 17:
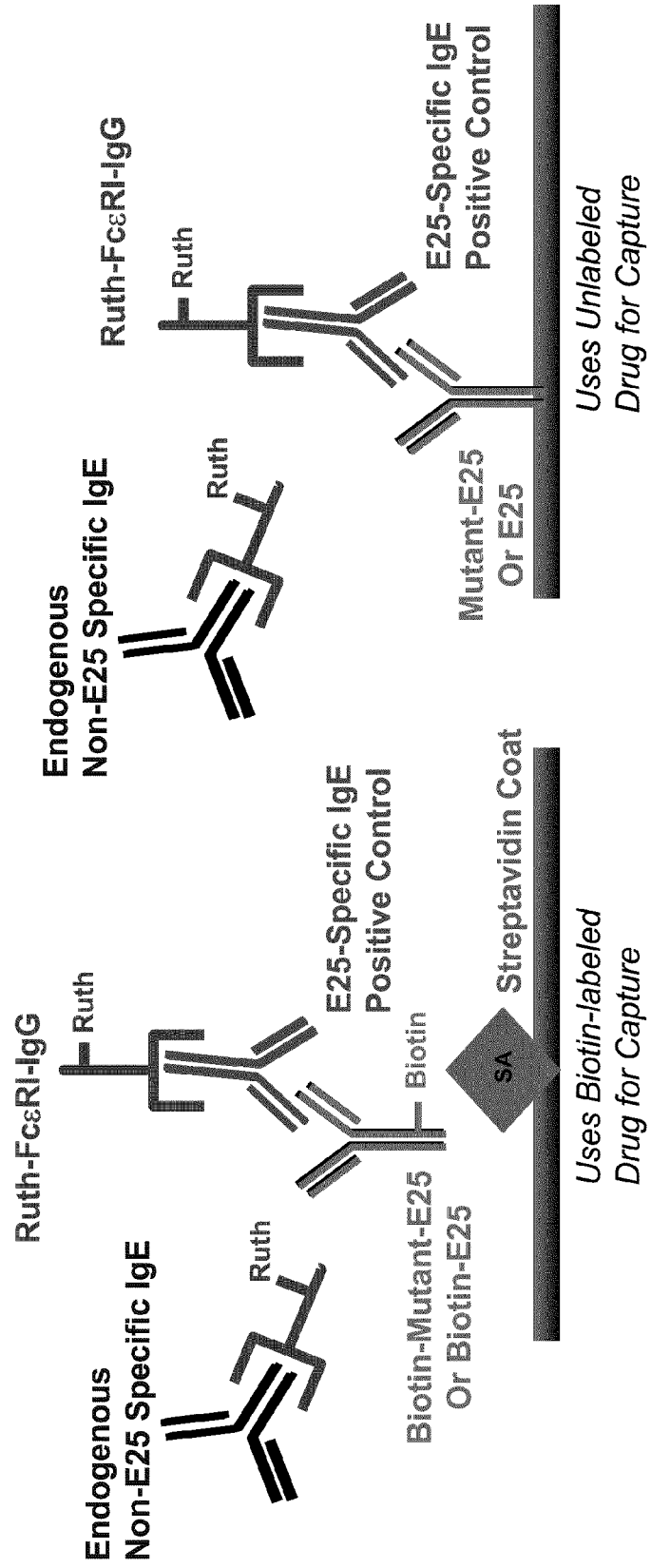

In some embodiments, the method comprises the steps: 1) preincubating a sample from an individual that may contain anti-drug antibodies of IgE isotype with at least about 10-fold excess of either an unlabeled or labeled FcεRIα polypeptide; 2) incubating the preincubated sample from step 1) with an immobilized anti-IgE therapeutic antibody or an immobilized mutant therapeutic antibody; 3) detecting binding of the anti-drug antibodies of IgE isotype to the therapeutic antibody or the mutant therapeutic antibody using a detection agent (such as a labeled anti-human IgE antibody or a labeled antibody specific for the label on the FcεRIα polypeptide that binds to the Fc region of an IgE). Washing steps are included between the incubation steps to remove molecules unbound to the solid phase (such as endogenous non-drug specific IgE). Examples of such assays are shown in FIGS. 15, 16, and 17.

In any of the methods described herein, the therapeutic anti-IgE antibody or a mutant antibody may comprise a label or may be conjugated to a label. In some embodiments, the methods comprising a step of capturing the labeled therapeutic anti-IgE antibody or the mutant antibody to a surface before detecting binding of the anti-drug antibody to the therapeutic anti-IgE antibody or the mutant antibody, wherein a capture agent that specifically binds to the label is immobilized to the surface. Any of the solid phase or surface (such as small sheets, Sephadex, polyvinyl chloride, plastic beads, microparticles, assay plates, or test tubes manufactured from polyethylene, and polystyrene) described herein may be used. In some embodiments, the surface is a cellulose polymer sponge (ImmunoCAP®, Phadia). In some embodiments, the surface is not a cellulose polymer sponge (ImmunoCAP®, Phadia). In some embodiments, the therapeutic anti-IgE antibody or the mutant antibody is labeled with biotin, and capture agent is streptavidin. In some embodiments, the FcεRIα polypeptide comprises a label, and the binding of the anti-drug antibody to the therapeutic anti-IgE antibody or the mutant antibody is detected by detecting binding of the FcεRIα polypeptide to the anti-drug antibody.

In some embodiments of the methods described herein, an FcεRIα polypeptide is used a detecting agent to detect binding of the anti-drug antibodies to the therapeutic anti-IgE antibody or the mutant therapeutic antibody. In some embodiments, the FcεRIα polypeptide comprises a label or is conjugated to a label. In some embodiments, the label on the FcεRIα polypeptide is digoxigenin, and the binding of the FcεRIα polypeptide to the anti-drug antibody is detected using a HRP conjugated anti-digoxigenin antibody. In some embodiments, the label on the FcεRIα polypeptide is ruthenium, and the binding of the FcεRIα polypeptide to the anti-drug antibody is detected using electrochemiluminescence.

In some embodiments of the methods described herein, an FcεRIα polypeptide is used as a blocking agent to block binding of the non-drug specific IgE in the sample to the therapeutic anti-IgE antibody or the mutant therapeutic antibody. In some embodiments, the binding of the anti-drug antibody to the therapeutic anti-IgE antibody or the mutant antibody is detected by detecting using a HRP conjugated anti-human IgE antibody.

The samples that may be used in the methods described herein include blood samples from individuals before treatment with an anti-IgE therapeutic antibody or after treatment with an anti-IgE therapeutic antibody. In some embodiments, blood samples are collected from individuals who have discontinued the anti-IgE antibody treatment for at least 16 weeks. In some embodiments, blood samples are collected from individuals who have discontinued the anti-IgE antibody treatment for at least 16 weeks but not more than 18 months since the last dose of the anti-IgE therapeutic antibody. In some embodiments, the samples are serum or plasma samples. The serum or plasma samples can be prepared using standard technology known in the art.

A positive control may be used to develop the assay, to evaluate assay sensitivity and drug tolerance, and/or used a control for the assay. A positive control may be used in any of the methods described herein. In some embodiments, the assay includes testing a positive control anti-drug antibody. A positive antibody that binds to both the therapeutic anti-IgE antibody and the mutant therapeutic antibody may be used. In some embodiments, the positive control anti-drug antibody binds to the Fab fragment of the anti-IgE antibody. In some embodiments, the positive control anti-drug antibody binds to one or more CDRs of the anti-IgE antibody. In some embodiments, the positive control antibody binds both the therapeutic anti-IgE antibody and the mutant therapeutic antibody with similar affinity. In some embodiments, the relative binding affinity of the positive control antibody to the therapeutic anti-IgE antibody is within about 10-fold, within about 9-fold, within about 8-fold, within about 7-fold, within about 6-fold, within about 5-fold, within about 4-fold, within about 3-fold, or within about 2-fold difference compared to relative binding affinity of the positive control antibody to the mutant therapeutic antibody. In some embodiments, the difference between the relative binding affinities of the positive control antibody to the therapeutic anti-IgE antibody and to the mutant therapeutic antibody is less than about 50%, less than about 40%, less than about 30%, less than about 20%, and/or less than about 10%. For example, a positive control antibody is a chimeric antibody comprising the variable regions from an anti-drug antibody (including a CDR-specific anti-drug antibody) and constant regions from an IgE (such as human IgE). In some embodiments, the control anti-drug antibody is a murine antibody against omalizumab (E25). Examples of anti-E25 antibodies that may be used as a positive control (such as AME2) are described in Example 2. In some embodiments, binding the anti-drug antibodies in a sample to the immobilized mutant antibody and binding of the positive control antibody to the immobilized mutant antibody are detected and compared.

The heavy and light chain variable region amino acid and nucleic acid sequences of antibody AME2 are shown below.

```
AME2 heavy chain variable region amino acid
sequence
                                      (SEQ ID NO: 7)
QVQLQQSGAELMKPGASVKISCKATGYTFSSHWIEWVKQRSGHGLEWIGE

ILPGSGSINYNEKFKGKATFTADTSSNTAYMQLSSLASEDSAVYYCGREG

ADYGYDVAMDYWGQGASVTVSS

AME2 light chain variable region amino acid
sequence
                                      (SEQ ID NO: 8)
QIVITQSPAIMSASPGEKVTITCSATSSVNYMHWFQQKPGTSPKLWIYGT

SHLASGVPARFSGSGSGTSYSLTISRMEAEDAATYYCQQRSYPFTFGSG

TKLEIKR

AME2 heavy chain variable region nucleic acid
sequence
                                      (SEQ ID NO: 9)
CAAGTTCAACTGCAGCAGTCTGGCGCTGAGCTGATGAAGCCTGGGGCCTC

AGTGAAGATATCCTGCAAGGCTACTGGCTACACATTCAGTAGCCACTGGA

TAGAGTGGGTGAAACAGAGGTCTGGACATGGCCTTGAGTGGATTGGAGAG

ATTCTACCTGGAAGTGGTAGTATTAATTACAATGAGAAGTTCAAGGGCAA

GGCCACATTCACAGCAGACACATCCTCCAACACAGCCTACATGCAACTCA

GCAGCCTGGCATCTGAGGACTCTGCCGTCTATTATTGTGGAAGAGAGGGG

GCCGACTATGGTTACGACGTTGCTATGGACTACTGGGGTCAAGGAGCCTC

GGTCACCGTCTCCTCG

AME2 light chain variable region nucleic acid
sequence
                                      (SEQ ID NO: 10)
CAAATTGTTATCACCCAGTCTCCAGCAATCATGTCTGCATCTCCAGGGGA

GAAGGTCACCATAACCTGTAGTGCCACCTCAAGTGTAAATTACATGCACT

GGTTCCAGCAGAAGCCAGGCACTTCTCCCAAACTCTGGATTTATGGCACA

TCCCACCTGGCTTCTGGAGTCCCTGCTCGCTTCAGTGGCAGTGGATCTGG

GACCTCTTACTCTCTCACAATCAGCCGAATGGAGGCTGAAGATGCTGCCA

CTTATTACTGCCAGCAAAGGAGTCGTTACCCATTCACGTTCGGCTCGGGG

ACAAAGCTCGAGATCAAACGG
```

In some embodiments, the heavy chain variable region of antibody AME2 is fused to a heavy chain constant region of a human IgE and the light chain variable region of antibody AME2 is fused to a light chain constant region of a human IgE to form a chimeric antibody. For the example, the following heavy and light chain constant regions of a human IgE may be used in a chimeric antibody.

```
A human IgE heavy chain constant region amino acid
sequence
                                      (SEQ ID NO: 29)
ASTQSPSVFPLTRCCKNIPSNATSVTLGCLATGYFPEPVMVTWDTGSLNG

TTMTLPATTLTLSGHYATISLLTVSGAWAKQMFTCRVAHTPSSTDWVDNK

TFSVCSRDFTPPTVKILQSSCDGGGHFPPTIQLLCLVSGYTPGTINITWL

EDGQVMDVDXSTASTTQEGELASTQSELTLSQKHWLSDRTYTCQVTYQGH

TFEDSTKKCADSNPRGVSAYLSRPSPFDLFIRKSPTITCLVVDLAPSKGT

VNLTWSRASGKPVNHSTRKEEKQRNGTLTVTSTLPVGTRDWIEGETYQCR

VTHPHLPRALMRSTTKTSGPRAAPEVYAFATPEWPGSRDKRTLACLIQNF

MPEDISVQWLHNEVQLPDARHSTTQPRKTKGSGFFVFSRLEVTRAEWEQK

DEFICRAVHEAASPSQTVQRAVSVNPGK

A human IgE light chain constant region amino acid
sequence
                                      (SEQ ID NO: 30)
ADAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVKS

FNRNEC
```

In some embodiments, a capture reagent (e.g., a mutant antibody, an anti-IgE antibody, an FcεRIα polypeptide, or streptavidin) is immobilized to a solid phase by insolubilizing the capture reagent either before the assay procedure, as by adsorption to a water-insoluble matrix or surface (U.S. Pat. No. 3,720,760) or non-covalent or covalent coupling, for example, using glutaraldehyde or carbodiimide cross-linking, with or without prior activation of the support with, for example, nitric acid and a reducing agent as described in U.S. Pat. No. 3,645,852 or in Rotmans et al., 1983, J. Immunol. Methods, 57:87-98, or after the assay procedure. In some embodiments, the capture reagent (e.g., the mutant antibody) after immobilization is available to bind a target molecule (e.g., the anti-drug antibodies) from a sample.

The solid phase or surface used for immobilization can be any inert support or carrier that is essentially water insoluble and useful in immunoassays, including supports in the form of, for example, surfaces, particles, porous matrices, cellulose polymer sponge (ImmunoCAP®, Phadia), and the like. Examples of commonly used supports include small sheets, Sephadex, polyvinyl chloride, plastic beads, microparticles, assay plates, or test tubes manufactured from polyethylene, polypropylene, polystyrene, and the like. In some embodiments, the solid phase or surface is a cellulose polymer sponge (ImmunoCAP®, Phadia). In some embodiments, the solid phase or surface is not a cellulose polymer sponge (ImmunoCAP®, Phadia). Such supports include 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. In an embodiment the immobilized capture reagent is coated on a microtiter plate. The preferred solid phase is a multi-well microtiter plate that can be used to analyze several samples at one time.

The solid phase is coated with the capture reagent (such as a mutant therapeutic antibody described herein) that can be linked by a non-covalent or covalent interaction or physical linkage, as desired. Techniques for attachment include those described in U.S. Pat. No. 4,376,110 and the references cited therein. If covalent attachment of the capture reagent to the plate is utilized, the plate or other solid phase can be incubated with a cross-linking agent together with the capture reagent. Commonly used cross-linking agents for attaching the capture reagent to the solid phase substrate include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates capable of forming cross-links in the presence of light.

If polystyrene plates are utilized, the wells in the plate are preferably coated with the capture reagent (typically diluted in a buffer such as 0.05 M sodium carbonate or 0.15 M phosphate buffered saline (PBS), pH 7.2 or 7.4) by incubation for at least about 10 hours, more preferably at least overnight, at temperatures of about 4-20° C., more preferably about 4-8° C., and at a pH of about 8-12, more preferably about 9-10, and most preferably about 9.6. If shorter coating times (1-2 hours) are desired, the plate is coated at 37° C. or plates with nitrocellulose filter bottoms such, as for example, Millipore MULTISCREEN™. The plates can be stacked and coated in advance of the assay, allowing for an immunoassay to be carried out simultaneously on several samples in a manual, semi-automatic, or automatic fashion, such as by using robotics. Polystyrene plates can be coated with streptavidin using the method described above.

The coated plates are typically treated with a blocking agent that binds non-specifically to, and saturates, the binding sites to prevent unwanted binding of free analyte molecules to excess binding sites on the wells of the plate. Examples of appropriate blocking agents include, for example, gelatin, bovine serum albumin, egg albumin, casein, and non-fat milk. The blocking treatment typically takes place under conditions of ambient temperatures for about 1-4 hours, preferably about 1.5 to 3 hours.

After coating and blocking, the sample to be analyzed is diluted as necessary and added to the immobilized phase. The preferred dilution rate is about 5-15%, preferably about 10%, by volume. Buffers that can be used for dilution include for example (a) phosphate buffered saline (PBS) containing 0.5% BSA, 0.05% TWEEN 20™, detergent (P20), 5 mM EDTA, 0.25% Chaps surfactant, 0.2% beta-gamma globulin, and 0.35M NaCl, pH 7.0; (b) PBS containing 0.5% BSA and 0.05% P20; (c) PBS containing 0.5% BSA, 0.05% P20, 5 mM EDTA, and 0.35 M NaCl, pH 6.35; (d) PBS containing 0.5% BSA, 0.05% P20, 5 mM EDTA, 0.2% beta-gamma globulin, and 0.35 M NaCl; (e) PBS containing 0.5% BSA, 0.05% P20, 5 mM EDTA, 0.25% Chaps, and 0.35 M NaCl; and (f) PBS containing 0.5% P20.

For sufficient sensitivity, it is preferred that the immobilized capture reagent is in molar excess of the maximum molar concentration of the analyte (such as anti-drug antibodies of IgE isotype) anticipated in the sample after appropriate dilution. Depending on the analyte, the capture reagent can compete for binding sites with the detecting antibody yielding inaccurate results. Therefore, the final concentration of the capture reagent will normally be determined empirically to maximize the sensitivity of the assay over the range of interest.

In some embodiments, the assay system has a sensitivity for anti-drug IgE of about 0.1 IU/ml to about 0.5 IU/ml (such as about 0.1 IU/ml, about 0.2 IU/ml, about 0.3 IU/ml, about 0.4 IU/ml, or about 0.5 IU/ml). In some embodiments, the assay system has total IgE tolerance of 700 IU/ml or higher. In some embodiments, the assay system has total IgE tolerance of 800 IU/ml or higher. In some embodiments, the assay system has drug tolerance (such as omalizumab tolerance) of at least about 50 ng/ml (such as about 50 ng/ml to about 200 ng/ml). In some embodiments, the drug tolerance for the assay system is at least about 50 ng/ml, at least about 75 ng/ml, at least about 100 ng/ml, at least about 125 ng/ml, or at least about 150 ng/ml.

Conditions for incubation of sample and capture reagent are selected to maximize sensitivity of the assay and to minimize dissociation. Incubation time depends primarily on the temperature. For example, the incubation time is from about 0.5 to 3 hours (including 1.5-3 hours) at 20-38° C. (including 36-38° C.), or overnight at room temperature. To maximize the anti-drug IgE sensitivity and the anti-IgE drug tolerance of the assay, incubation times greater than about 10 hours are used if possible. If the sample is a biological fluid (such as blood or serum) incubation times can be lengthened by adding a protease inhibitor to the sample to prevent proteases in the biological fluid from degrading the analyte.

The pH of the incubation buffer is chosen to maintain a significant level of specific binding of the capture reagent to the analyte being captured. In some embodiments, the pH of the incubation buffer is about 6-9.5 (including pH about 6-7). In some embodiments, the pH of the incubation buffer is about 7.2. Various buffers can be employed to achieve and maintain the desired pH during this step, including borate, phosphate, carbonate, Tris-HCl or Tns-phosphate, acetate, barbital, and the like. The particular buffer employed is usually not critical, however, and in individual assays one buffer may be preferred over another.

The sample is separated from the immobilized capture reagent with a wash solution to remove uncaptured analyte (such as anti-drug antibodies) from the system. The wash solution is generally a buffer. The incubation buffers described above are suitable wash solutions. The pH of the wash solution is determined as described above for the incubation buffer. In an embodiment, the pH of the wash solution is about 6-9, more preferably about 6-7. Washes can be done one or more times. Minimizing the number of washes, however, to retain molecules that bind the target molecule with low affinity increases the background noise of the assay. In some embodiments, the system is washed three times. The temperature of the wash solution is typically from about 0-40° C., more preferably about 4-30° C. An automated plate washer can be utilized. A cross-linking agent or other suitable agent can be added to the wash solution to covalently attach the captured analyte to the capture reagent.

Following removal of uncaptured analyte molecules from the system, the captured analyte molecules are contacted with a detecting agent, such as an antibody or an FcεRIα polypeptide, such as at a temperature of about 20-40° C., about 36-38° C., or room temperature. In some embodiments, the analyte is an anti-drug antibody of the IgE isotype, the detecting agent is a labeled FcεRIα-IgG chimeric receptor.

The temperature and time for contacting the analyte molecule with the detecting agent is dependent primarily on the detection means employed. For example, when horseradish peroxidase (HRP) conjugated to streptavidin (SA-HRP) is used as the means for detection, the detecting agent is preferably incubated with the captured analyte for about 0.5-2 hours, more preferably about 1 hour. The system is washed as described above to remove unbound detecting agent from the system and developed by adding peroxidase substrate and incubating the plate for about 15 minutes at room temperature or until good color is visible. In an embodiment, a molar excess of the detecting agent is added to the system after the unbound analyte has been washed from the system.

The affinity of the detecting agent must be sufficiently high such that small amounts of analyte can be detected. A fluorimetric or chemilimunescent label moiety has greater sensitivity in immunoassays compared to a conventional colorimetric label. The binding affinity of the selected detecting agent must be considered in view of the binding affinity of the capture agent, such that the detecting agent does not strip the analyte from the capture reagent.

The label moiety is any detectable functionality that does not interfere with the binding of the captured analyte to the detecting agent. Examples of suitable label moieties include moieties that can be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737, 456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HPP, lactoperoxidase, or microperoxidase, biotin/avidin, biotin/streptavidin, biotin/Streptavidin-beta-galactosidase with MUG, digoxigenin, ruthenium, spin labels, bacteriophage labels, stable free radicals, and the like.

Conjugation of the label moiety to the detecting agent, such as for example an antibody or an FcεRIα polypeptide, is a standard manipulative procedure in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Conventional methods are available to bind the label moiety covalently to proteins or polypeptides. For example, coupling agents such as dialdehydes, carbodiimides, dimaleimides, bis-imidates, bis-diazotized benzidine, and the like can be used to label antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., 1962, Nature, 144:945; David et al., 1974, Biochemistry, 13:1014-1021; Pain et al., 1981, J. Immunol. Methods, 40:219-230; and Nygren J., 1982, Histochem. and Cytochem., 30:407-412. Preferred labels herein are fluorescent or chemiluminescent to increase amplification and sensitivity to about 5-10 pg/ml. In an embodiment, the label moiety is HRP.

The amount of analyte bound to the capture reagent is determined by washing away unbound detecting agent from the immobilized phase and measuring the amount of detecting agent bound to the analyte using a detection method appropriate to the label. In an embodiment, the label moiety is an enzyme. In the case of enzyme moieties, the amount of developed color is a direct measurement of the amount of captured analyte. For example, when HRP is the label moiety, color is detected by quantifying the optical density (O.D.) absorbance (e.g., at 450 nm). In another embodiment, the quantity of analyte bound to the capture reagent is determined indirectly. The signal of an unlabeled detecting agent can be amplified for detection with an anti-detecting agent antibody conjugated to a label moiety. For example, the signal of an unlabeled mouse antibody that binds the target molecule can be amplified with a sheep anti-mouse IgG antibody labeled with HRP. The label moiety is detected using a detection method appropriate to the label. For example, HRP can be detected by reacting HRP with a calorimetric substrate and measuring the optical density of the reacted substrate at 450 nm absorbance.

The pH and/or temperature of the system can be varied to identify molecules that bind the target molecule.

Methods for Assessing or Aiding Assessment of Risk for Anaphylaxis to a Therapeutic Anti-IgE Antibody Treatment The methods described herein may be used to assess or aid assessment of risk for an anaphylactic reaction to the administration of a therapeutic anti-IgE antibody. The methods described herein may also be used for identifying patients having a risk for anaphylactic reaction to the administration of a therapeutic anti-IgE antibody.

Blood samples from patients treated with a therapeutic anti-IgE antibody (such as E25, omalizumab) with anaphylaxis and patients without hypersensitivity reactions are collected. Data including clinical histories, allergy skin test results and immunogenicity evaluations are collected. The amount of anti-drug antibodies of IgE isotype in the samples are tested using the assays described herein. A correlation between the allergy skin test, anaphylaxis and the level of anti-drug antibodies of IgE isotype is established. Samples will be collected after anaphylaxis or after all participants including controls have discontinued anti-IgE treatment for at least 16 weeks but no more than 18 months. The established correlation can be used to establish a reference level, and can be used to assess or aid assessment of risk of anaphylaxis to a therapeutic anti-IgE antibody before a patient is treated with the therapeutic anti-IgE antibody.

In one aspect, the invention provides a method for assessing or aiding assessment of risk in a patient for an anaphylactic reaction to the administration of a therapeutic anti-IgE antibody, comprising the steps of: a) detecting the level of anti-drug antibodies of IgE isotype that bind to the therapeutic anti-IgE antibody in a sample from the patient before anti-IgE antibody treatment; and b) comparing the level detected in step a) to a reference level. In some embodiments, patients having the level of anti-drug antibodies of IgE isotype higher than a reference level is excluded from the anti-IgE antibody treatment.

In another aspect, the invention provides methods of identifying a patient having a risk of anaphylactic reaction to a therapeutic anti-IgE antibody, comprising detecting the presence and/or the level of anti-drug antibodies of IgE isotype in a sample from the patient using any of the methods described herein, wherein the presence and/or the level of the anti-drug antibody in the sample indicates that the patient has a risk of anaphylactic reaction to the therapeutic anti-IgE antibody.

Methods for Treating IgE-Mediated Disorders

The anti-drug antibodies of IgE isotype in a patient may be assessed using the assay methods described herein before or after the patient is treated with an anti-IgE antibody. The invention provides a method for treating an IgE-mediated disorder in an individual with an anti-IgE antibody comprising comparing the level of anti-drug antibodies of IgE isotype in a sample from the individual to a reference level; and administering an effective amount of the anti-IgE antibody to the individual if the level of anti-drug antibodies in the sample is lower than a reference level. In one aspect, the invention provides a method for identifying patient having high-risk of anaphylaxis comprising comparing the level of anti-drug antibodies of IgE isotype in a sample from an individual to a reference level, wherein the individual is identified as having high-risk of anaphylaxis if the level of anti-drug antibodies in the sample is higher than a reference level. In another aspect, the invention provides methods of treating a patient having an IgE-mediated disorder, comprising the steps of: (a) determining the level of an anti-drug antibody of IgE isotype to a therapeutic anti-IgE antibody in a sample from the patient using any of the methods described herein; (b) administering an effective amount of the therapeutic anti-IgE antibody to the patient if the level of the anti-drug antibody in the sample do not indicate that the patient has a risk of anaphylactic reaction to the therapeutic anti-IgE antibody.

For the prevention or treatment of IgE-mediated disorders, the appropriate dosage of an anti-IgE antibody, will depend on the type of disease to be treated, the severity and course of the disease, whether the anti-IgE antibody is administered for preventive or therapeutic purposes, previous therapy, the patient's clinical history and response to the agent, and the discretion of the attending physician. The anti-IgE antibody is suitably administered to the patient at one time or over a series of treatments. In some embodiments, the anti-IgE antibody is omalizumab. The anti-IgE antibody may be in liquid formulations or is reconstituted from lyophilized formulations. Formulations suitable for anti-IgE antibodies are described in U.S. Pat. No. 6,875,432; and U.S. Pub. Nos. 2004/0197324 and 2005/0158303.

The anti-IgE antibody is administered to an individual in need of treatment, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

The IgE-mediated disorders include allergic rhinitis, asthma (e.g., allergic asthma and non-allergic asthma), atopic dermatitis, allergic gastroenteropathy, hypersensitivity (e.g., anaphylaxis, urticaria, food allergies etc.), allergic bronchopulmonary aspergillosis, parasitic diseases, interstitial cystitis, hyper-IgE syndrome, ataxia-telangiectasia, Wiskott-Aldrich syndrome, thymic alymphoplasia, IgE myeloma and graft-versus-host reaction. In yet a further specific aspect, the IgE-mediated disorder is food allergy, anaphylaxis, contact dermatitis and allergic purpura.

The IgE-mediated disorders treatable by the method of the invention also include ataxia-telangiectasia, Churg-Strauss Syndrome, eczema, enteritis, gastroenteropathy, graft-versus-host reaction, hyper-IgE (Job's) syndrome, hypersensitivity (e.g., anaphylactic hypersensitivity, candidiasis, vasculitis), IgE myeloma, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis, parasitic diseases (e.g., trypanosomiasis), hypersensitivity vasculitis, urticaria and Wiskott-Aldrich syndrome.

The IgE-mediated disorders treatable by the method of the invention also include Addison's disease (chronic adrenocortical insufficiency), alopecia, hereditary angioedema, anigioedema (Bannister's disease, angioneurotic edema), ankylosing spondylitis, aplastic anemia, arteritis, amyloidosis, immune disorders, such as autoimmune hemolytic anemia, autoimmune oophoritis, autoimmune orchitis, autoimmune polyendocrine failure, autoimmune hemolytic anemia, autoimmunocytopenia, autoimmune glomerulonephritis, Behcet's disease, bronchitis, Buerger's disease, bullous pemphigoid, Caplan's syndrome (rheumatoid pneumoconiosis), carditis, celiac sprue, Chediak-Higashi syndrome, chronic obstructive lung Disease (COPD), Cogan-Reese syndrome (iridocorneal endothelial syndrome), CREST syndrome, dermatitis herpetiformis (Duhring's disease), diabetes mellitus, eosinophilic fasciitis, eosinophilic nephritis, episcleritis, extrinsic allergic alveolitis, familial paroxysmal polyserositis, Felty's syndrome, fibrosing alveolitis, glomerulonephritis, Goodpasture's syndrome, granulocytopenia, granuloma, granulomatosis, granuloma myositis, Graves' disease, Guillain-Barre syndrome (polyneuritis), Hashimoto's thyroiditis (lymphadenoid goiter), hemochromatosis, histocytosis, hypereosinophilic syndrome, irritable bowel syndrome, juvenile arthritis, keratitis, leprosy, lupus erythematosus, Lyell's disease, Lyme disease, mixed connective tissue disease, mononeuritis, mononeuritis multiplex, Muckle-Wells syndrome, mucocutaneous lymphoid syndrome (Kawasaki's disease), multicentric reticulohistiocystosis, multiple sclerosis, myasthenia gravis, mycosis fungoides, panninculitis, pemphigoid, pemphigus, pericarditis, polyneuritis, polyarteritis nodoas, psoriasis, psoriatic arthritis, pulmonary arthritis, pulmonary adenomatosis, pulmonary fibrosis, relapsing polychondritis, rheumatic fever, rheumatoid arthritis, rhinosinusitis (sinusitis), sarcoidosis, scleritis, sclerosing cholangitis, serum sickness, Sezary syndrome, Sjogren's syndrome, Stevens-Johnson syndrome, systemic mastocytosis, transplant rejection, thrombocytopenic purpura, thymic alymphoplasia, uveitis, vitiligo, Wegener's granulomatosis.

The IgE-mediated disorders may be treated by an anti-IgE antibody in combination with known methods of treatments for IgE-mediated disorders, either as combined or additional treatment steps or as additional components of a therapeutic formulation. For example, the treatment includes an anti-IgE antibody in combination with an antihistamine, a sympathomimetic, a bronchodilator, a glucocorticoid, a non-steroidal anti-inflammatory drug, a decongestant, a cough suppressant or an analgesic. In another specific aspect, the anti-IgE antibody is administered in combination with a treatment regimen of allergen desensitization.

D. Kits

The invention also provide kits for use in the methods described herein.

In one aspect, the invention provides kits for detecting anti-drug antibodies of IgE isotype that bind to a therapeutic anti-IgE antibody in a sample, comprising a mutant therapeutic antibody comprising at least one amino acid mutation from the therapeutic anti-IgE antibody, wherein the relative binding affinity of the mutant therapeutic antibody to an IgE (such as human IgE) is about 10% or less of the relative binding affinity of the therapeutic anti-IgE antibody to the IgE. In some embodiments, the kits further comprise a detecting agent that binds to an Fc region of a human IgE (such as an FcεRIα polypeptide described herein).

In another aspect, the invention provides kits for detecting anti-drug antibodies of IgE isotype that bind to a therapeutic anti-IgE antibody in a sample, comprising a mutant therapeutic antibody comprising at least one amino acid mutation from the therapeutic anti-IgE antibody, wherein the potency of the mutant therapeutic antibody to an IgE is about 10% or less of the potency of the therapeutic anti-IgE antibody to the IgE. In some embodiments, the kits further comprise a detecting agent that binds to an Fc region of a human IgE (such as an FcεRIα polypeptide described herein).

In another aspect, the invention provides kits for detecting anti-drug antibodies of IgE isotype that bind to a therapeutic anti-IgE antibody in a sample, comprising (a) a mutant therapeutic antibody comprising at least one amino acid mutation from the therapeutic anti-IgE antibody, wherein the relative binding affinity of the mutant therapeutic antibody to an IgE (such as human IgE) is about 10% or less of the relative binding affinity of the therapeutic anti-IgE antibody to the IgE; and (b) an FcεRIα polypeptide that binds to an Fc region of a human IgE.

In another aspect, the invention provides kits for detecting anti-drug antibodies of IgE isotype that bind to a therapeutic anti-IgE antibody in a sample, comprising (a) the therapeutic anti-IgE antibody or a mutant therapeutic antibody thereof, wherein the mutant therapeutic antibody comprises at least one amino acid mutation from the therapeutic anti-IgE antibody, wherein the relative binding affinity of the mutant therapeutic antibody to an IgE (such as human IgE) is reduced as compared to the relative binding affinity of the therapeutic anti-IgE antibody to the IgE; and (b) an FcεRIα polypeptide that binds to an Fc region of a human IgE.

In some embodiments, the kits further comprise a positive control antibody that binds both the therapeutic anti-IgE antibody and the mutant therapeutic antibody. In some embodiments, the positive control antibody binds both the therapeutic anti-IgE antibody and the mutant therapeutic antibody with similar affinity. In some embodiments, the positive control antibody comprises the heavy and light variable regions from an antibody that specific binds to Fab fragment of the anti-IgE antibody and constant regions from a human IgE. In some embodiments, the positive control antibody comprises a heavy chain variable region comprising the amino acid sequence shown in SEQ ID NO:7, and a light chain variable region comprising the amino acid sequence shown in SEQ ID NO:8. In some embodiments, the positive control antibody binds to the complex of Fab fragment of the anti-IgE antibody and IgE.

The reagents of the kits (such as therapeutic anti-IgE antibody, the mutant therapeutic antibody, the positive control antibody, and/or the FcεRIα polypeptide) may be in a container. In some embodiments, the therapeutic anti-IgE antibody, the mutant therapeutic antibody, positive control antibody, and/or the FcεRIα polypeptide comprise a label.

In some embodiments, the therapeutic anti-IgE antibody or the mutant therapeutic antibody is immobilized directly or indirectly to a surface. In some embodiments, the therapeutic anti-IgE antibody or the mutant therapeutic antibody is conjugated to a label (such as a biotin). In some embodiments, the therapeutic anti-IgE antibody or the mutant therapeutic antibody is conjugated to a label is captured to a surface through an immobilized capture agent that specifically binds to the label. In some embodiments, the label is biotin and the capture agent is streptavidin.

In some embodiments, the detecting agent or FcεRIα polypeptide is conjugated to a label (such as a biotin, digoxigenin, or ruthenium). In some embodiments, the detecting agent is a labeled FcεRI polypeptide. In some embodiments, the kit further comprises streptavidin-HRP or Amdex SA-HRP. In some embodiments, the kit further comprises HRP-conjugated anti-digoxigenin antibody for detecting digoxigenin labeled FcεRI polypeptide. In some embodiments, the kit further comprises labeled anti-human IgE antibody (such as a polyclonal antibody or a monoclonal antibody). In some embodiments, the labeled anti-human IgE antibody is a HRP-conjugated anti-human IgE antibody.

The kits of the invention may further comprise any instructions for use in accordance with any of the methods described herein. In some embodiments, these instructions comprise a description of testing the amount of anti-drug antibodies of IgE isotype in a patient sample according to any methods described herein. The kits may further comprise a description of assessing risk of anaphylaxis of a patient before treatment with the anti-IgE antibody. The instructions may be provided on a label or package insert. Kits may optionally comprise additional components such as buffers and reagents for carrying out the methods described herein.

The kits of the invention are in suitable packaging. Suitable packaging includes, but is not limited to, vials, bottles, jars, flexible packaging (e.g., sealed Mylar or plastic bags), and the like. Also contemplated are packages for use in combination with a specific device, such as a device for signal detection in an ELISA assay.

The following are examples of the methods and compositions of the invention. It is understood that various other embodiments may be practiced, given the general description provided above.

EXAMPLES

Example 1

Preparation of a Mutant Antibody from Anti-IgE Antibody Omalizumab

The antibody omalizumab (E25 or rhuMAbE25) is a humanized anti-human IgE antibody described in U.S. Pub. No. 2005/0158303 and U.S. Pat. No. 6,172,213. The amino acid sequences of the heavy and light chain variable region of E25 are provided in FIG. 2 in U.S. Pat. No. 6,172,213, and the amino acid sequences of the full length heavy and light chain of E25 are provided in FIG. 12 in U.S. Pat. No. 6,172,213. The heavy chain and light chain amino acid sequences of antibody E25 are shown in FIGS. 1A and 1B. A mutant E25, referred to as E25-AAA mutant, containing three amino acid substitutions in the light chain CDR1 was generated. The mutations are substitutions from D to A at positions 30, 32, 34 shown in SEQ ID NO:1. This mutant antibody is described in Presta et al., J. Immunol. 151:2623-2632, 1993.

The binding affinity of this mutant antibody to human IgE relative to E25 was tested as shown in FIG. 2A. E25 or E25-AAA mutant was immobilized on an ELISA plate, increasing concentration of purified human IgE was added to the plate. Binding of human IgE to E25 or to E25-AAA mutant was detected by a goat anti-human IgE conjugated with a HRP. The OD at 450 nm was measured. These experiments were carried out using known methods. See, e.g., Engvall et al., Immunochemistry 8:871-4, 1971; Presta et al., J. Immunol. 151:2623-2632, 1993. As shown in FIG. 2B, E25-AAA mutant has about 100× less binding affinity to human IgE than E25.

To compare the primary structure of E25 with E25-AAA mutant, Lys-C peptide mapping was used. Lys-C enzyme was used for digestion so that the 3 amino acid substitutions were all in the same peptide (light chain 1-43). The peptide map profiles showed only two peak differences in the mutant, the parent peptide LC 1-43 that disappeared, and a new peak not present in E25. LC-MS was run and the mass of the new peak in the mutant was confirmed as LC 1-43 with the 3 Ala replacing the 3 Asp. Therefore this analysis confirmed the mutant had the same primary structure of E25, with the exception of the 3 Ala substituting the 3 Asp in the LC.

AME14, AME4, or AME5) was added to the plate. Binding of the anti-drug antibody to E25 or E25-AAA mutant was detected by an anti-mouse IgG antibody conjugated with a HRP. The OD at 450 nm was measured. As shown in FIGS. 4A-4H and Table 2 below, AME2, AME10, AME4 and AME5 are specific for E25 Fab and are specific for E25 framework region; AME1, AME7, and AME 9 are specific for E25 CDRs; AME13 is specific for E25 framework region. Since AME2, AME10, AME13, AME4, AME5, and AME7 bind to both E25 and E25-AAA mutant, these antibodies may be used to test and screen mutant anti-IgE antibodies that may be used in assay described herein.

TABLE 2

Mouse antibodies that bind to E25 and E25-AAA mutant

| Ab | E25 Full-Length | E25 Fab | Control Ab Full-Length | MAE11c | MAE1 | E25 Fab/IgE Complex | E25 Full-Length | E25-AAA Mutant Full-Length |
|---|---|---|---|---|---|---|---|---|
| AME1 | + | + | - | + | - | - | + | - |
| AME7 | + | + | - | + | - | - | + | +/- |
| AME9 | + | + | - | + | - | - | + | - |
| AME2 | + | + | - | - | - | + | + | + |
| AME10 | + | + | - | - | - | - | + | + |
| AME13 | + | - | + | - | - | - | + | + |
| AME4 | + | + | + | - | - | - | + | + |
| AME5 | + | + | + | - | - | + | + | + |

The charge distribution of E25-AAA mutant was also studied. The charge distribution of monoclonal antibodies is usually specific to the molecule. In this case the amino acid substitutions in the mutant changed the pI of the molecule significantly (from 7.6 to ~9), therefore the migration time of the mutant was very different. Additionally, differences in the profiles are expected due to the substitution of Asp32 which contributes to the heterogeneity (it isomerizes) of the charge distribution of E25. The iCIEF (imaged capillary isoelectric focusing) profiles for E25 and E25-AAA mutant were similar, though not identical, with similar amounts of acidic and basic variants.

Example 2

Comparison of Binding of Anti-Drug Antibodies to E25 and E25-AAA Mutant

Murine monoclonal antibodies specific to E25 were generated. As shown in Table 2 below, AME1, AME7, AME9, AME2, AME10, AME13, AME4, and AME5 are antibodies that bind to E25. AME1, AME7, AME9, AME2, AME10, AME4, and AME5 are mouse IgG1, and AME13 is a mouse IgG2 antibody. E25 is a humanized antibody derived from MAE11 as described in Example 1 and in Presta et al., *J. Immunol.* 151:2623-2632, 1993. MAE1 is a control anti-human IgE monoclonal antibody, and has different CDRs from MAE11. MAE 1 and MAE11 are mouse IgG antibodies. Control antibody (full length) is an IgG antibody with framework residues similar to E25, but binds a different antigen. Negative binding to MAE1 demonstrated that AMEs were specific to E25 sequences only. To test whether these anti-drug antibodies bind equally well to E25 and E25-AAA mutant, binding assays were carried out using methods known in the art. See, e.g., Engvall et al., *Immunochemistry* 8:871-4, 1971. E25 or E25-AAA mutant was immobilized on a ELISA plate, increasing concentration of a purified anti-drug antibody (AME1, AME7, AME9, AME2, AME10, Example 3

Preparation of an E25-Specific IgE Positive Control Antibody

Figure 5:
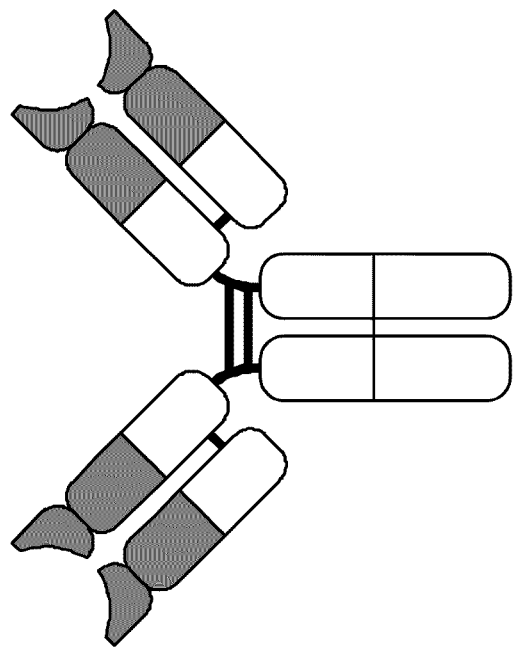
FIG. 5 shows an E25-specific IgE chimeric antibody engineered as a positive control antibody for the assay system. The variable regions of the chimeric antibody are from antibody AME2 which specifically binds to Fab fragment of E25, and the constant regions of the chimeric antibody are from a human IgE antibody.

FIG. 5 shows a positive control antibody that may be used in the assay system described herein. This antibody has the heavy and light chain variable regions from AME2 and constant regions from a human IgE.

Figure 6B:
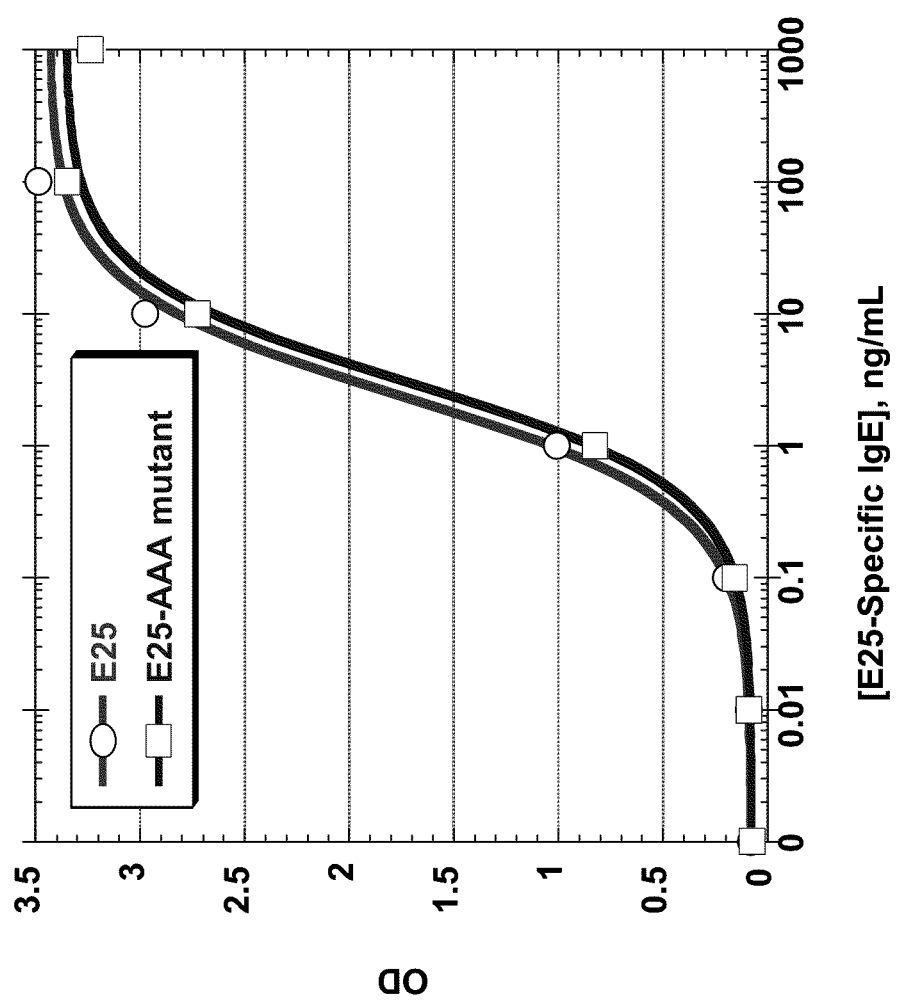
FIG. 6B is a graph showing that the chimeric E25-specific IgE positive control antibody binds to E25 and 25-AAA mutant with similar affinity.

The positive control antibody was tested using an assay shown in FIG. 6A. The surface of an ELISA plate was coated with human FcεRIα IgG chimeric receptor. E25-specific IgE positive control antibody was added to the plate and incubated to allow binding to the immobilized receptor. Either E25 or E25-AAA mutant with increasing concentration was added to the plate and incubated to allow binding of E25 or E25-AAA mutant. Binding of E25 or E25-AAA mutant to the plate was measured using HRP-anti-human IgG antibody. The results are shown in FIG. 6B. The experiment indicates that the positive control antibody shown in FIG. 3 binds equally well to E25 and E25-AAA mutant and may be used in the assay system described herein as a positive control for the assay or for screening additional mutant antibodies.

Example 4

Detection of Anti-Drug Antibodies of IgE Isotype in a Sample Using Direct ELISA Format FIG. 7 shows an assay system for detecting E25-specific IgE. E25-AAA mutant antibody is used to coat the surface of an ELISA plate. Alternatively, the mutant antibody is immobilized on the surface of a cellulose polymer sponge (ImmunoCAP® design, Phadia). A patient serum sample is added to the surface and incubated under a condition to allow binding of any E25-specific IgE to E25-AAA mutant. A biotin labeled human FcεRIα-IgG chimeric receptor (e.g., as described in WO 08/028,068) is added to the ELISA plate (or Immuno- CAP®) to detect any E25-specific IgE bound to E25-AAA mutant. SA-HRP (streptavidin-horseradish peroxidase conjugate) is added to detect biotin-FcεRI-IgG.

Alternatively, another detecting system is used for detecting binding E25-specific IgE to E25-AAA mutant. The following steps are used for a direct ELISA assay: a) coating a plate overnight at 2-8° C. with E25-AAA mutant; b) adding assay diluent (PBS, 0.5% BSA, 0.05% polysorbate 20, and 0.05% ProClin 300) to the plate and incubating it for 2 hours at room temperature with agitation; c) adding 1:2 diluted serum samples containing E25-specific IgE and non-E25-specific IgE to the plate and incubating it overnight at room temperature with agitation; d) adding biotin-labeled FcεR1-IgG to the plate and incubating it for 1 hour at room temperature with agitation; e) adding Amdex-streptavidin-HRP to the plate and incubating it 1 hour at room temperature with agitation; f) adding tetramethylbenzidine (TMB) substrate to the plate and incubating it for about 15 minutes; and g) adding 1M phosphoric acid to the plate and reading the absorbance at $A_{450}$-$A_{650}$. The plate is also washed three times between each of the steps before step f).

Example 5

Figure 10:
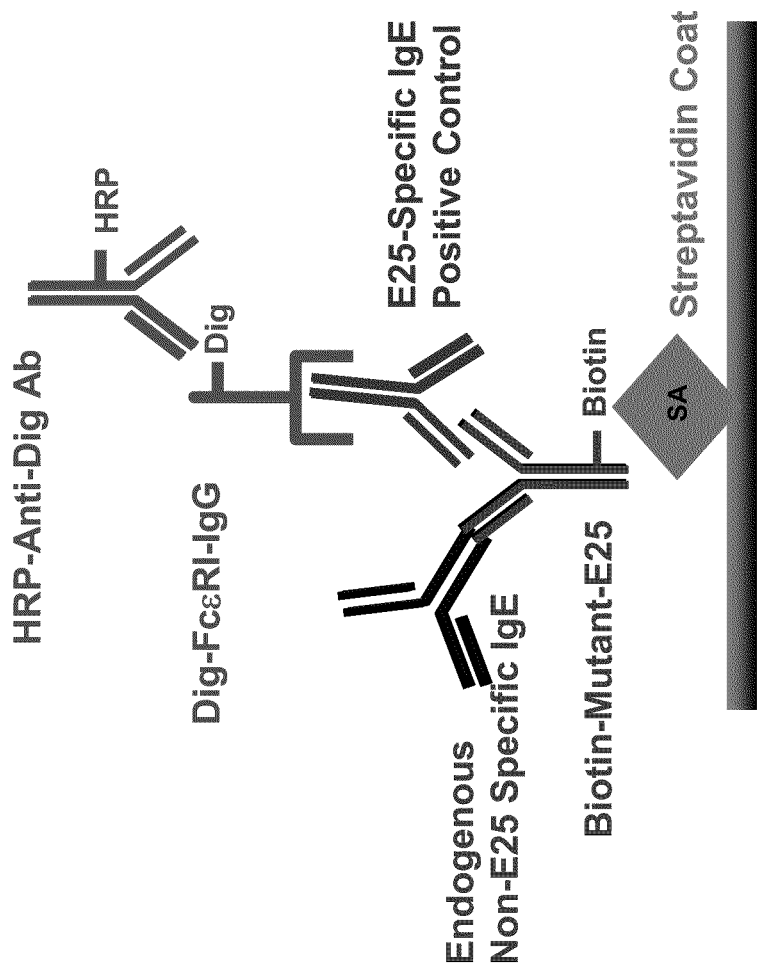
FIG. 10 is a diagrammatic representation of an assay for detecting E25-specific antibodies of IgE isotype using a semi-homogenous ELISA format.

Detection of Anti-Drug Antibodies of IgE Isotype in a Sample Using Semi-Homogeneous and Homogeneous Assays FIG. 10 shows a semi-homogeneous ELISA format to detect E25-specific IgE in a sample. The following steps are used: a) preincubating serum samples containing E25-specific IgE and non-E25-specific IgE with biotin-labeled E25-AAA mutant for overnight at room temperature with agitation; b) adding assay diluent (PBS, 0.5% BSA, 0.05% Polysorbate 20, and 0.05% ProClin 300) to a streptavidin-coated plate and incubating it for 1-2 hours at room temperature with agitation or using a pre-blocked streptavidin-coated plate (such as Reacti-Bind Streptavidin Coated High Binding Capacity (HBC) Clear 96-well Plate(s) with Super Blocker BSA, Pierce cat. #15500); c) adding the preincubated serum samples to the plate and incubating them for 0.5-2 hours (e.g., 1 hour) at room temperature with agitation; d) adding digoxigenin-labeled FcεR1-IgG to the plate and incubating it for 1 hour at room temperature with agitation; e) adding HRP-labeled anti-digoxigenin antibody to the plate and incubating it for 1 hour at room temperature with agitation; f) adding TMB substrate to the plate and incubating it for about 15 minutes; and g) adding 1M phosphoric acid to the plate and reading the absorbance at $A_{450}$-$A_{650}$. The plate is washed three times between steps, for example, after each of the steps of b) to e).

For example, 1 ug/mL of biotin-labeled E25-AAA Mutant in Assay Diluent (PBS, 0.5% BSA, 0.05% Polysorbate 20, 0.05% ProClin 300) is diluted 1:1 with human serum and pre-incubated together overnight at room temperature with agitation. The 1:2 pre-incubated serum sample is then added to a streptavidin-coated microtiter plate (Pierce cat. #15500), incubated for 1 hour at room temperature with agitation, then washed. Bound E25-specific IgE is detected by incubation with ~250 ng/mL of DIG-labeled FcεR1-IgG in Assay Diluent for 1 hour at room temperature with agitation. The plate is washed and incubated with ~1:6000 HRP-labeled mouse anti-DIG MAb (Jackson ImmunoResearch cat. #200-032-156) in Assay Diluent for 1 hour at room temperature with agitation. The plate is washed a final time and incubated with TMB substrate for 15-30 minutes for color development and measurement.

FIG. 11 shows a semi-homogeneous MSD-ECLA format to detect E25-specific IgE in a sample. The following steps are used: a) preincubating serum samples containing E25-specific IgE and non-E25-specific IgE with biotin-labeled mutant E25 (such as E25-AAA mutant) for overnight at room temperature with agitation; b) adding assay diluent (PBS, 0.5% BSA, 0.05% Polysorbate 20, and 0.05% ProClin 300) to a MSD streptavidin-coated plate (Meso Scale Discovery (MSD), Gaithersburg, Md., USA) and incubating it for 1-2 hours at room temperature with agitation; c) adding the preincubated serum samples to the streptavidin-coated plate and incubating it for 1-2 hours at room temperature with agitation; d) adding ruthenium-labeled FcεR1-IgG and incubating for 1-2 hours at room temperature with agitation; and e) adding MSD TPA read buffer and immediately reading the signal. The plate is washed between steps, for example, after each of the steps of b) to d).

FIG. 12 shows a "blocking" homogeneous ELISA format to detect E25-specific IgE in a sample. The following steps are used: a) preincubating serum samples containing E25-specific IgE and non-E25 specific IgE with a biotin-labeled mutant E25 (such as E25-AAA mutant) and a greater than 10 fold excess FcεR1-IgG for overnight at room temperature with agitation; b) adding assay diluent (PBS, 0.5% BSA, 0.05% Polysorbate 20, and 0.05% ProClin 300) to a streptavidin-coated plate and incubating it for 1-2 hours at room temperature with agitation; c) adding the preincubated serum samples to the plate and incubating it for 1-2 hours at room temperature with agitation; d) adding HRP-labeled anti-Human IgE antibody to the plate and incubating it for 1-2 hours at room temperature with agitation; e) adding TMB substrate to the plate and incubating it for about 15 minutes; and f) adding 1M phosphoric acid to the plate and reading the absorbance at $A_{450}$-$A_{650}$. The plate is washed between steps, for example, after each of the steps of b) to d).

FIG. 13 shows a "blocking" homogeneous ELISA format to detect E25-specific IgE in a sample. The following steps are used: a) preincubating serum samples containing E25-specific IgE and non-E25 specific IgE with a biotin-labeled mutant-E25 (such as E25-AAA mutant) and greater than 10-fold excess of digoxigenin-labeled FcεR1-IgG for overnight at room temperature with agitation; b) adding assay diluent (PBS, 0.5% BSA, 0.05% Polysorbate 20, and 0.05% ProClin 300) to a streptavidin-coated plate and incubating it for 1-2 hours at room temperature with agitation; c) adding the preincubated serum samples to the plate and incubating it for 1-2 hours at room temperature with agitation; d) adding HRP-labeled anti-digoxigenin antibody to the plate and incubating it for 1-2 hours at room temperature with agitation; e) adding TMB substrate to the plate and incubating for about 15 minutes; and f) adding 1M phosphoric acid to the plate and reading the absorbance at $A_{450}$-$A_{650}$. The plate is washed between steps, for example, after each of the steps of b) to d).

FIG. 14 shows a homogeneous "blocking" MSD-ECLA format to detect E25-specific IgE in a sample. The following steps are used: a) preincubating serum samples containing E25-specific IgE and non-E25 specific IgE with a biotin-labeled mutant E25 (such as E25-AAA mutant) and a greater than 10 fold excess of ruthenium-labeled FcεR1-IgG for overnight at room temperature with agitation; b) adding assay diluent (PBS, 0.5% BSA, 0.05% Polysorbate 20, and 0.05% ProClin 300) to a streptavidin-coated plate and incubating it for 1-2 hours at room temperature with agitation; c) adding the preincubated serum samples to the plate and incubating it for 1-2 hours at room temperature with agitation; d) adding MSD TPA read buffer and immediately reading the signal. The plate is washed between steps, for example, after each of the steps of b) to c).

FIG. 15 shows a semi-homogeneous "blocking" ELISA format to detect E25-specific IgE in a sample. The following steps are used: a) coating a plate overnight at 2-8° C. with E25 (or an E25 mutant (such as E25-AAA mutant)) (FIG. 15, right panel) or adding biotin-labeled E25 (or a biotin-labeled E25 mutant (such as E25-AAA mutant)) (FIG. 15, left panel) to a pre-coated streptavidin plate and incubating it for 1-2 hours at room temperature with agitation; b) adding assay diluent (PBS, 0.5% BSA, 0.05% polysorbate 20, and 0.05% ProClin 300) to the plate and incubating it for 2 hours at room temperature with agitation; c) preincubating serum samples containing E25-specific IgE and non-E25 specific IgE with greater than 10-fold excess of unlabeled FcεR1-IgG and incubating them overnight at room temperature with agitation; d) adding the preincubated serum samples to the plate and incubating it for 1-2 hours at room temperature with agitation; e) adding HRP-labeled anti-human IgE antibody to the plate and incubating it for 1-2 hours at room temperature with agitation; f) adding TMB substrate to the plate and incubating for about 15 minutes; and g) adding 1M phosphoric acid to the plate and reading the absorbance at $A_{450}$-$A_{650}$. The plate is washed between steps, for example, after each of the steps of a), b), d), and e).

FIG. 16 shows a semi-homogeneous "blocking" ELISA format to detect E25-specific IgE in a sample. The following steps are used: a) coating a plate overnight at 2-8° C. with E25 (or an E25 mutant (such as E25-AAA mutant)) (FIG. 16, right panel) or adding biotin-labeled E25 (or a biotin-labeled E25 mutant (such as E25-AAA mutant)) (FIG. 16, left panel) to a pre-coated streptavidin plate and incubating it for 1-2 hours at room temperature with agitation; b) adding assay diluent (PBS, 0.5% BSA, 0.05% polysorbate 20, and 0.05% ProClin 300) to the plate and incubating it for 2 hours at room temperature with agitation; c) preincubating serum samples containing E25-specific IgE and non-E25 specific IgE with greater than 10-fold excess of digoxigenin-labeled FcεR1-IgG for overnight at room temperature with agitation; d) adding the preincubated serum samples to the plate and incubating it for 1-2 hours at room temperature with agitation; e) adding HRP-labeled anti-digoxigenin antibody to the plate and incubating it for 1-2 hours at room temperature with agitation; f) adding TMB substrate to the plate and incubating for about 15 minutes; and g) adding 1M phosphoric acid to the plate and reading the absorbance at $A_{450}$-$A_{650}$. The plate is washed between steps, for example, after each of the steps of a), b), d) and e).

FIG. 17 shows a semi-homogeneous "blocking" MSD-ECLA format to detect E25-specific IgE in a sample. The following steps are used: a) coating a plate overnight at 2-8° C. with E25 (or an E25 mutant (such as E25-AAA mutant)) (FIG. 17, right panel) or adding biotin-labeled E25 (or a biotin-labeled E25 mutant) (FIG. 17, left panel) to a pre-coated streptavidin plate and incubating it for 1-2 hours at room temperature with agitation; b) adding assay diluent (PBS, 0.5% BSA, 0.05% polysorbate 20, and 0.05% ProClin 300) to the plate and incubating it for 2 hours at room temperature with agitation; c) preincubating serum samples containing E25-specific IgE and non-E25 specific IgE with greater than 10-fold excess of ruthenium-labeled FcεR1-IgG for overnight at room temperature with agitation; d) adding the preincubated serum samples to the plate and incubating it for 1-2 hours at room temperature with agitation; and e) adding MSD TPA read buffer and immediately reading the signal. The plate is washed between steps, for example, after each of the steps of a), b) and d).

Example 6

Assay Sensitivity for Anti-Drug-Specific Antibody of IgE Isotype

The sensitivity for E25 specific IgE antibodies of the assay system described in Example 4 (FIG. 7) was determined. A microtiter plate was coated overnight at 4° C. with E25-AAA Mutant in 0.05M Na Carbonate Buffer, pH 9.6, washed 3× with Wash Buffer (PBS, 0.05% Polysorbate 20, pH 7.2) and then blocked with Assay Diluent (PBS, 0.05% Polysorbate 20, 0.5% BSA, 0.05% ProClin 300, pH 7.2) for two hours at room temperature. A E25-specific IgE (Positive Control shown in FIG. 5) Standard Curve was prepared by adding 0.4-1000 ng/mL of Positive Control (PC) to neat normal human serum pool (NHS Pool) and then diluting each standard sample 1:2 in Assay Diluent. The 1:2 Positive Control Standard Curve Samples were added to the E25-AAA Mutant coated microtiter plate and allowed to incubate overnight at room temperature with agitation. The microtiter plate was then washed 6× with Wash Buffer.

Biotin-labeled rhuFcεR1-IgG diluted in Assay Diluent (PBS, 0.5% BSA, 0.05% Polysorbate 20, and 0.05% ProClin 300) was added to the microtiter plate and allowed to incubate for 1 hour at room temperature with agitation. The microtiter plate was then washed 6× with Wash Buffer. Amdex Streptavidin-Horseradish Peroxidase (Amdex SA-HRP) diluted in Assay Diluent was added to the microtiter plate and allowed to incubate for 1 hour at room temperature with agitation. The microtiter plate was then washed 6× with Wash Buffer. TMB Substrate was then added to the microtiter plate and allowed to incubate for 15 minutes at room temperature. Phosphoric Acid was then added to the microtiter plate to stop the color development and the absorbance signal of each well read using a plate reader at 450 nm with a 650 nm reference.

Figure 8:
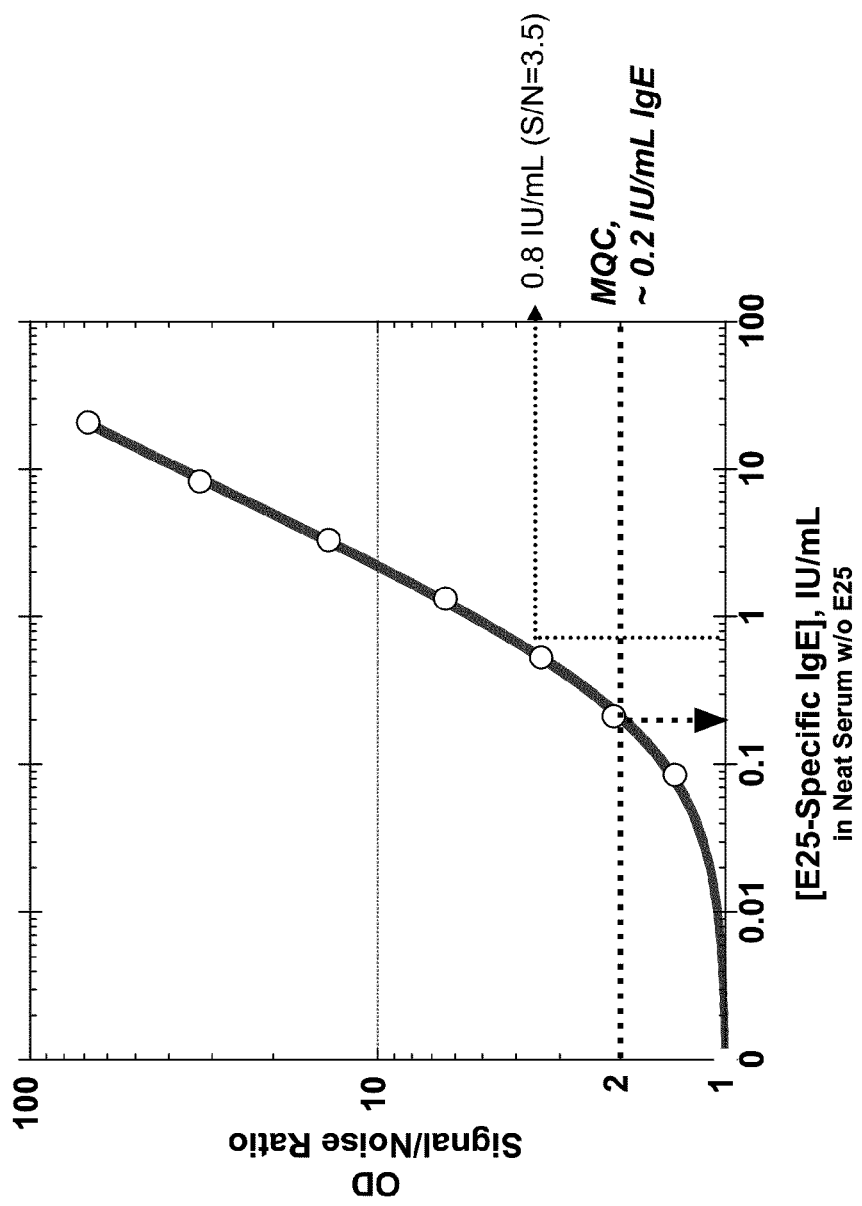
FIG. 8 shows a E25-specific IgE standard curve to determine the sensitivity of an assay for detecting E25-specific antibodies of IgE isotype using E25-AAA mutant antibody. This figure shows the results using the assay format described in FIG. 7.

The E25-specific IgE (PC) Standard Curve is shown in FIG. 8. The minimum quantifiable concentration (MQC) of E25-specific IgE antibodies was 0.2 IU/ml (0.48 ng/ml) for this assay system.

The sensitivity for E25 specific IgE antibodies of the assay system described in FIG. 10 was determined. A E25-specific IgE (Positive Control shown in FIG. 5) Standard Curve was prepared by adding 0.1-100 IU/mL of Positive Control (PC) to neat normal human serum pool (NHS Pool) and then diluting each standard sample 1:2 in Assay Diluent (PBS, 0.05% Polysorbate 20, 0.5% BSA, 0.05% ProClin 300, pH 7.2) containing 1 µg/mL of biotin-labeled E25-AAA Mutant. The 1:2 Positive Control Standard Curve Samples were allowed to pre-incubate overnight at room temperature with agitation. A microtiter plate pre-coated with streptavidin (Pierce cat. #15125) was washed 3× with Wash Buffer (PBS, 0.05% Polysorbate 20, pH 7.2). The pre-incubated 1:2 Positive Control Standard Curve Samples were added to the streptavidin coated microtiter plate and allowed to incubate for 1 hour at room temperature with agitation. The microtiter plate was then washed 3× with Wash Buffer. Digoxigenin-labeled rhuFcεR1-IgG diluted in Assay Diluent was added to the microtiter plate and allowed to incubate for 1 hour at room temperature with agitation. The microtiter plate was then washed 3× with Wash Buffer. Anti-Digoxigenin monoclonal antibody-Horseradish Peroxidase (HRP-Anti-DIG MAb, Jackson ImmunoResearch Laboratories Inc. cat. #200-032-156) diluted in Assay Diluent was added to the microtiter plate and allowed to incubate for 1 hour at room temperature with agitation. The microtiter plate was then washed 3× with Wash Buffer. TMB Substrate was then added to the microtiter plate and allowed to incubate for 15 minutes at room temperature. Phosphoric Acid was then added to the microtiter plate to stop the color development and the absorbance signal of each well read using a plate reader at 450 nm with a 650 nm reference. The E25-specific IgE (PC) Standard Curve is shown in Table 3 below. The minimum quantifiable concentration (MQC) of E25-specific IgE antibodies was 0.1 IU/ml (0.24 ng/ml) for this assay system. The method for Table 4 below is the same as described above for Table 3 with the following changes: 1) A E25-specific IgE (Positive Control shown in FIG. 5) Standard Curve was prepared by adding 0.1-6.4 IU/mL instead of 0.1-100 IU/mL of Positive Control (PC) to neat normal human serum pool (NHS Pool); and 2) The pre-coated streptavidin plate was Pierce cat. #15500 instead of Pierce cat. #15125.

TABLE 3

Semi-homogeneous ELISA format sensitivity

| Xolair-Specific IgE, IU/mL | Pierce SA-Plate OD | Signal/ Noise Ratio |
|---|---|---|
| 100 | 3.905 | 92.8 |
| 30 | 3.899 | 92.6 |
| 10 | 3.379 | 80.3 |
| 3 | 1.365 | 32.4 |
| 1 | 0.472 | 11.2 |
| 0.3 | 0.182 | 4.3 |
| 0.1 | 0.087 | 2.1 |
| 0 | 0.042 | 1.00 |

Standard Curve in NHS Pool with about 159 IU/ml total IgE.

TABLE 4

Semi-homogeneous ELISA format sensitivity

| Xolair-Specific IgE, IU/mL | Pierce SA-Plate OD | Signal/ Noise Ratio |
|---|---|---|
| 6.4 | 1.708 | 33.7 |
| 3.2 | 1.029 | 20.3 |
| 1.6 | 0.575 | 11.4 |
| 0.8 | 0.287 | 5.7 |
| 0.4 | 0.167 | 3.3 |
| 0.2 | 0.109 | 2.2 |
| 0.1 | 0.078 | 1.5 |
| 0 | 0.051 | 1.00 |

Example 7

Figure 9:
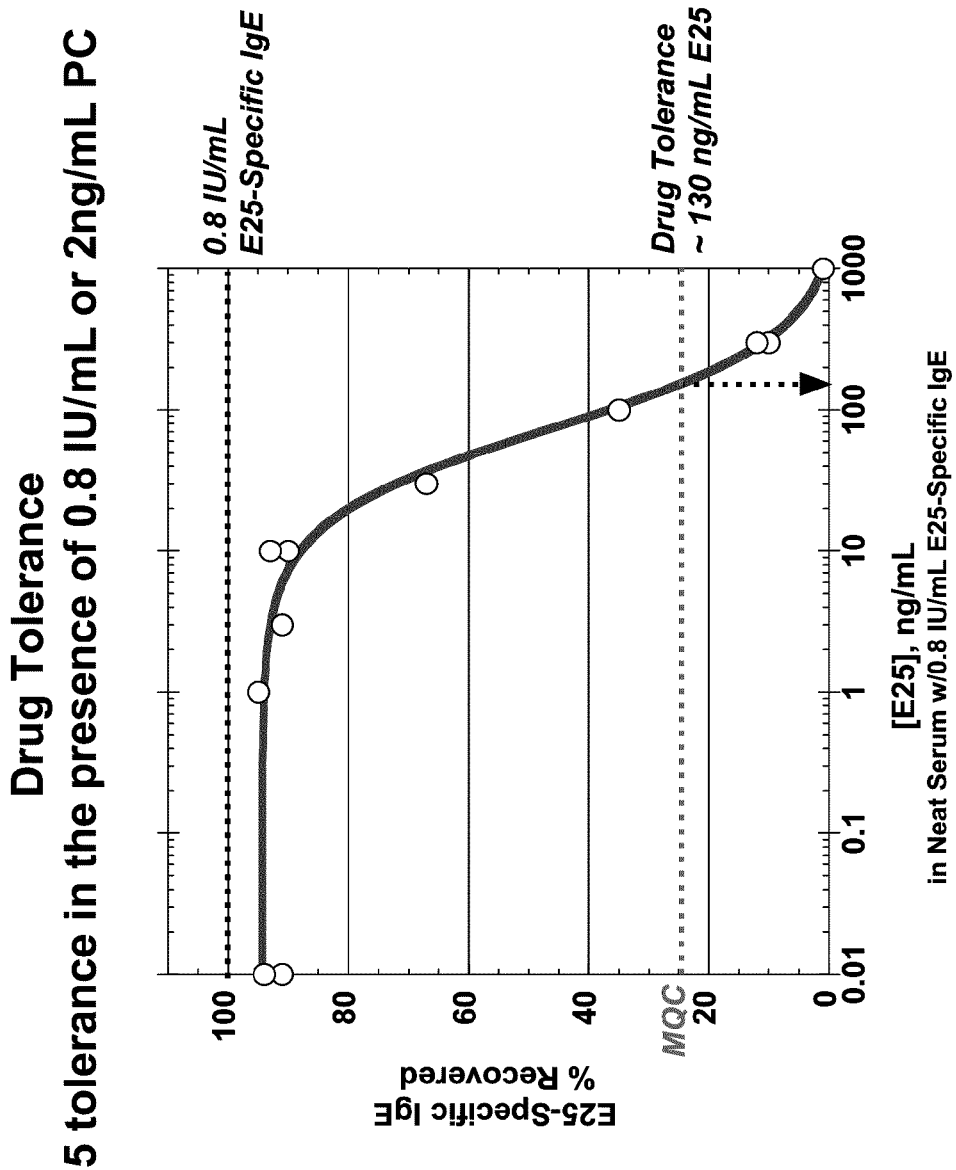
FIG. 9 shows the drug tolerance of the assay for detecting E25-specific antibodies of IgE isotype using E25-AAA mutant antibody in the presence of increasing concentrations of E25.

Drug-Tolerance of Assay System for Detection of Anti-Drug-Specific Antibody of IgE Isotype The drug tolerance of the assay system described in Example 4 (FIG. 7) was tested in the presence of 0.8 IU/ml (2 ng/ml) of Positive Control (E25-specific IgE shown in FIG. 5) and increasing concentrations of E25. Microtiter plates were coated with E25-AAA mutant as described in Example 6. E25 Drug-Tolerance Test Samples were prepared by adding 1-1000 ng/mL E25 to neat NHS Pool containing 2 ng/mL of PC and then diluting each drug-tolerance sample 1:2 in Assay Diluent. The 1:2 E25 Drug-Tolerance Samples were then added to the E25-AAA Mutant coated microtiter plate and further processed to detect E25 specific antibodies as described in Example 6. The results of this assay are shown in FIG. 9. In the presence of 0.8 IU (2 ng/ml) of E25-specific antibodies, the E25 tolerance of the assay was ~130 ng/ml E25.

The drug tolerance of the assay system described in FIG. 10 was tested in the presence of 0.2, 1, and 5 IU/ml (0.48, 2.4, and 12 ng/ml) of Positive Control (E25-specific IgE shown in FIG. 5) and 0, 10, 50, and 150 ng/mL concentrations of E25. A E25-specific IgE (Positive Control) Standard Curve was prepared by adding 0.1-6.4 IU/mL of Positive Control (PC) to neat normal human serum pool (NHS Pool). E25 Drug-Tolerance Test Samples were prepared by adding 0, 10, 50, and 150 ng/mL E25 to neat NHS Pool or 3 individual Allergic Asthma human sera with up to 812 IU/ml of non-specific IgE containing 0.2, 1, and 5 IU/ml of PC. Both the Standard Curve and Drug Tolerance samples were then diluted 1:2 in Assay Diluent (PBS, 0.05% Polysorbate 20, 0.5% BSA, 0.05% ProClin 300, pH 7.2) containing 1 ug/mL of biotin-labeled E25-AAA Mutant. The 1:2 Samples were allowed to pre-incubate overnight at room temperature with agitation. A microtiter plate pre-coated with streptavidin (Pierce cat. #15500) was washed 3× with Wash Buffer (PBS, 0.05% Polysorbate 20, pH 7.2). The pre-incubated 1:2 Samples were added to the streptavidin coated microtiter plate and allowed to incubate for 1 hour at room temperature with agitation. The microtiter plate was then washed 3× with Wash Buffer. Digoxigenin-labeled rhuFcɛR1-IgG diluted in Assay Diluent was added to the microtiter plate and allowed to incubate for 1 hour at room temperature with agitation. The microtiter plate was then washed 3× with Wash Buffer. Anti-Digoxigenin monoclonal antibody-Horseradish Peroxidase (HRP-Anti-DIG MAb, Jackson ImmunoResearch Laboratories Inc. cat. #200-032-156) diluted in Assay Diluent was added to the microtiter plate and allowed to incubate for 1 hour at room temperature with agitation. The microtiter plate was then washed 3× with Wash Buffer. TMB Substrate was then added to the microtiter plate and allowed to incubate for 15 minutes at room temperature. Phosphoric Acid was then added to the microtiter plate to stop the color development and the absorbance signal of each well read using a plate reader at 450 nm with a 650 nm reference. The results of this assay are shown in Table 5 below. In the presence of 0.2 IU (0.48 ng/ml) of E25-specific antibodies, the E25 tolerance of the assay was ~50 ng/ml E25.

TABLE 5

Semi-homogeneous ELISA format drug tolerance

| Serum Total IgE, IU/Ml | E25-Specific IgE Added, IU/mL | E25 Added, ng/mL | Drug-specific IgE Detected, IU/mL |
|---|---|---|---|
| 1 = 107 IU/mL | 0.2 | 0 | 0.26 |
|  |  | 16.7 | 0.17 |
|  |  | 50 | 0.13 |
|  |  | 150 | QNS |
| Pool = 159 IU/mL | 0.2 | 0 | 0.32 |
|  |  | 16.7 | 0.24 |
|  |  | 50 | 0.18 |
|  |  | 150 | <0.1 |
| 5 = 419 IU/mL | 0.2 | 0 | 0.37 |
|  |  | 16.7 | 0.29 |
|  |  | 50 | 0.17 |
|  |  | 150 | <0.1 |
| 7 = 812 IU/mL | 0.2 | 0 | 0.37 |
|  |  | 16.7 | 0.33 |
|  |  | 50 | 0.26 |
|  |  | 150 | 0.14 |

The total IgE interference for the assay system described in FIG. 10 was also tested. A E25-specific IgE (Positive Control)

Standard Curve was prepared by adding 0.1-6.4 IU/mL of Positive Control (PC) to neat normal human serum pool (NHS Pool). Ten Total IgE Interference Samples consisting of 9 human serum samples from individuals diagnosed with Allergic Asthma (Sera provided by the company Bioreclamation, Westbury, N.Y.) and a normal human serum pool with varying Total IgE levels of 107-2446 IU/mL were chosen for analysis. Both the Standard Curve and the ten Total IgE Interference samples were then diluted 1:2 in Assay Diluent (PBS, 0.05% Polysorbate 20, 0.5% BSA, 0.05% ProClin 300, pH 7.2) containing 1 ug/mL of biotin-labeled E25-AAA Mutant. The 1:2 Samples were allowed to pre-incubate overnight at room temperature with agitation. A microtiter plate pre-coated with streptavidin (Pierce cat. #15500) was washed 3× with Wash Buffer (PBS, 0.05% Polysorbate 20, pH 7.2). The pre-incubated 1:2 Samples were added to the streptavidin coated microtiter plate and allowed to incubate for 1 hour at room temperature with agitation. The microtiter plate was then washed 3× with Wash Buffer. Digoxigenin-labeled rhuFcεR1-IgG diluted in Assay Diluent was added to the microtiter plate and allowed to incubate for 1 hour at room temperature with agitation. The microtiter plate was then washed 3× with Wash Buffer. Anti-Digoxigenin monoclonal antibody-Horseradish Peroxidase (HRP-Anti-DIG MAb, Jackson ImmunoResearch Laboratories Inc. cat. #200-032-156) diluted in Assay Diluent was added to the microtiter plate and allowed to incubate for 1 hour at room temperature with agitation. The microtiter plate was then washed 3× with Wash Buffer. TMB Substrate was then added to the microtiter plate and allowed to incubate for 15 minutes at room temperature. Phosphoric Acid was then added to the microtiter plate to stop the color development and the absorbance signal of each well read using a plate reader at 450 nm with a 650 nm reference.

Table 6 below shows that there was no total IgE interference if total IgE in the sample was at ≤800 IU/ml.

TABLE 6

Semi-homogeneous ELISA format total IgE interference

| Serum Total IgE, IU/mL | OD | Non-Specific IgE Detected, IU/mL |
|---|---|---|
| 1 = 107 IU/mL | 0.034 | <0.1 |
| 2 = 145 IU/mL | 0.042 | <0.1 |
| Pool = 159 IU/mL | 0.051 | <0.1 |
| 3 = 213 IU/mL | 0.041 | <0.1 |
| 4 = 286 IU/mL | 0.050 | <0.1 |
| 5 = 419 IU/mL | 0.050 | <0.1 |
| 6 = 664 IU/mL | 0.048 | <0.1 |
| 7 = 812 IU/mL | 0.052 | <0.1 |
| 8 = 1767 IU/mL | 0.084 | 0.12 |
| 9 = 1855 IU/mL | 0.115 | 0.23 |
| 10 = 2446 IU/mL | 0.128 | 0.28 |

The accuracy of the assay system described in FIG. 10 was also tested. The accuracy of the assay system described in FIG. 10 was tested in the presence of 0, 0.2, 1, and 5 IU/ml (0.48, 2.4, and 12 ng/ml) of Positive Control (E25-specific IgE shown in FIG. 5). A E25-specific IgE (Positive Control) Standard Curve was prepared by adding 0.1-6.4 IU/mL of Positive Control (PC) to neat normal human serum pool (NHS Pool). Accuracy Test Samples were prepared by adding 0, 0.2, 1, and 5 IU/ml of PC to neat NHS Pool or 3 individual Allergic Asthma human sera with up to 812 IU/ml of non-specific IgE. Both the Standard Curve and Accuracy samples were then diluted 1:2 in Assay Diluent (PBS, 0.05% Polysorbate 20, 0.5% BSA, 0.05% ProClin 300, pH 7.2) containing 1 ug/mL of biotin-labeled E25-AAA Mutant. The 1:2 Samples were allowed to pre-incubate overnight at room temperature with agitation. A microtiter plate pre-coated with streptavidin (Pierce cat. #15500) was washed 3× with Wash Buffer (PBS, 0.05% Polysorbate 20, pH 7.2). The pre-incubated 1:2 Samples were added to the streptavidin coated microtiter plate and allowed to incubate for 1 hour at room temperature with agitation. The microtiter plate was then washed 3× with Wash Buffer. Digoxigenin-labeled rhuFcεR1-IgG diluted in Assay Diluent was added to the microtiter plate and allowed to incubate for 1 hour at room temperature with agitation. The microtiter plate was then washed 3× with Wash Buffer. Anti-Digoxigenin monoclonal antibody-Horseradish Peroxidase (HRP-Anti-DIG MAb, Jackson ImmunoResearch Laboratories Inc. cat. #200-032-156) diluted in Assay Diluent was added to the microtiter plate and allowed to incubate for 1 hour at room temperature with agitation. The microtiter plate was then washed 3× with Wash Buffer. TMB Substrate was then added to the microtiter plate and allowed to incubate for 15 minutes at room temperature. Phosphoric Acid was then added to the microtiter plate to stop the color development and the absorbance signal of each well read using a plate reader at 450 nm with a 650 nm reference. The results are shown in Table 7 below. There seems to be a trend toward over-recovery of IgE with increasing levels of total IgE.

TABLE 7

Semi-homogeneous ELISA format accuracy

| Serum Total IgE, IU/mL | E25-Specific IgE Added, IU/mL | Drug-specific IgE Detected, IU/mL | % Recovery of Expected IgE |
|---|---|---|---|
| 1 = 107 IU/mL | 0 | <0.1 | |
| | 0.2 | 0.26 | 130 |
| | 1 | 1.20 | 120 |
| | 5 | 4.00 | 80 |
| Pool = 159 IU/mL | 0 | <0.1 | |
| | 0.2 | 0.32 | 160 |
| | 1 | 1.19 | 119 |
| | 5 | 4.35 | 87 |
| 5 = 419 IU/mL | 0 | <0.1 | |
| | 0.2 | 0.37 | 185 |
| | 1 | 1.44 | 144 |
| | 5 | 5.87 | 117 |
| 7 = 812 IU/mL | 0 | <0.1 | |
| | 0.2 | 0.37 | 185 |
| | 1 | 1.33 | 133 |
| | 5 | 5.68 | 114 |

The Total IgE (non-specific IgE) levels of the individual Allergic Asthma sera were determined by the sera vendor (Bioreclamation) using the commercial Total IgE assay from Phadia.

The Total IgE level of the NHS Pool was determined using a method for detecting total free IgE in a human serum sample. Samples drawn prior to administration of E25 were incubated with a plate coated with rhuFcεRI-IgG. Binding between IgE in the sample and the rhuFcεRI-IgG was detected by adding biotin-conjugated anti-human IgE antibodies to the plate, and followed by adding streptavidin-conjugated-beta-galactosidase reagent. The plate was washed and incubated with 0.34 mg/mL MUG (4-methylumbelliferyl b-D-galactoside) in 0.1 M Sodium Phosphate, 1 mM $MgCl_2$, pH 7.5. This reaction was then stopped with the addition of 0.3M Glycine, pH 10.5 and the fluorescent signal read. The signal correlates with the level of IgE in the serum sample.

Although the foregoing invention has been described in some detail by way of illustration and example for purposes of clarity of understanding, the descriptions and examples should not be construed as limiting the scope of the invention.

What is claimed is:

1. A method for detecting an anti-drug antibody of IgE isotype that may be present in a sample from a human patient, wherein variable regions of the anti-drug antibody specifically bind to a therapeutic anti-IgE antibody, comprising the steps of:
   (a) contacting the sample with a mutant of the therapeutic antibody comprising one, two, three, four, five, or six amino acid mutations in complementarity determining region (CDR) sequences of a heavy or light chain of the therapeutic anti-IgE antibody, wherein relative binding affinity of the mutant therapeutic antibody to an Fc region of human IgE is about 10% or less of relative binding affinity of the therapeutic anti-IgE antibody to said Fc region of human IgE; and
   (b) detecting specific binding of the anti-drug antibody of IgE isotype in the sample to the mutant therapeutic antibody, wherein the detection of the specific binding indicates presence or level of the anti-drug antibody of IgE isotype in the patient.

2. The method of claim 1, wherein the relative binding affinity of the mutant therapeutic antibody to the human IgE is about 5% or less of the relative binding affinity of the therapeutic anti-IgE antibody to the human IgE.

3. The method of claim 1, wherein the relative binding affinity of the mutant therapeutic antibody to the human IgE is about 2.5% or less of the relative binding affinity of the therapeutic anti-IgE antibody to the human IgE.

4. The method of claim 1, wherein the relative binding affinity of the mutant therapeutic antibody to the human IgE is about 1% or less of the relative binding affinity of the therapeutic anti-IgE antibody to the human IgE.

5. The method of claim 1, wherein the relative binding affinity is measured by comparing the binding to the human IgE in an enzyme-linked immunosorbent assay (ELISA).

6. The method of claim 1, wherein the sample is human serum or plasma from the human patient or a dilution thereof.

7. The method of claim 6, wherein the serum or plasma sample contains the therapeutic antibody.

8. The method of claim 6, wherein the serum or plasma sample does not contain the therapeutic antibody.

9. The method of claim 1, wherein the therapeutic anti-IgE antibody is omalizumab.

10. The method of claim 1, wherein the therapeutic anti-IgE antibody is omalizumab, and the mutant therapeutic antibody comprises one, two, or three amino acid mutations in the first CDR sequence of the light chain of omalizumab.

11. The method of claim 10, wherein the mutant therapeutic antibody comprises the heavy chain amino acid sequence of SEQ ID NO:2 and the light chain amino acid sequence of SEQ ID NO: 1, wherein Asp amino acid residues at positions 30, 32, and 34 are substituted in the light chain.

12. The method of claim 10, wherein the mutant therapeutic antibody comprises the heavy chain amino acid sequence of SEQ ID NO:2 and the light chain amino acid sequence of SEQ ID NO:1 with amino acid substitutions of Asp to Ala at positions 30, 32, and 34.

13. The method of claim 1, further comprising a step of comparing the binding of the anti-drug antibodies of the IgE isotype to the mutant therapeutic antibody detected in step b) to a reference.

14. The method of claim 13, wherein the reference is detected binding between the mutant therapeutic antibody and a control antibody.

15. The method of claim 14, wherein the control antibody is a positive control antibody that binds both the therapeutic anti-IgE antibody and the mutant therapeutic antibody, wherein difference between relative binding affinities of the positive control antibody to the therapeutic anti-IgE antibody and to the mutant therapeutic antibody is less than 50%.

16. The method of claim 15, wherein the positive control antibody comprises a heavy chain variable region comprising the amino acid sequence shown in SEQ ID NO:7 and a light chain variable region comprising the amino acid sequence shown in SEQ ID NO:8.

17. A method for detecting an anti-drug antibody of IgE isotype that may be present in a sample from a human patient, wherein variable regions of the anti-drug antibody specifically bind to a therapeutic anti-IgE antibody, comprising the steps of:
(a) contacting the sample with a mutant of the therapeutic antibody comprising one, two, three, four, five, or six amino acid mutations in complementarity determining region (CDR) sequences of a heavy or light chain of the therapeutic anti-IgE antibody, wherein potency of the mutant therapeutic antibody to human IgE is about 10% or less of potency of the therapeutic anti-IgE antibody to said human IgE; and
(b) detecting specific binding of the anti-drug antibody of IgE isotype in the sample to the mutant therapeutic antibody, wherein the detection of the specific binding indicates presence or level of the anti-drug antibody of IgE isotype in the patient.

18. The method of claim 1 or claim 17, wherein the mutant therapeutic antibody is captured to a surface.

19. The method of claim 18, wherein the mutant therapeutic antibody is captured by direct immobilization to the surface.

20. The method of claim 18, wherein the mutant therapeutic antibody is labeled and is captured to the surface through a capture agent that specifically binds to the label, wherein the capture agent is immobilized to the surface.

21. The method of claim 20, wherein the label is biotin and the capture agent is streptavidin.

22. The method of claim 20, wherein the label is digoxigenin and the capture agent is an anti-digoxigenin antibody.

23. The method of claim 1 or claim 17, wherein the sample is contacted with the mutant therapeutic antibody that is captured to a surface.

24. The method of claim 1 or claim 17, wherein the sample is contacted with the mutant therapeutic antibody before the mutant therapeutic antibody is captured to a surface.

25. The method of claim 1 or claim 17, wherein the binding of the anti-drug antibodies of the IgE isotype to the mutant therapeutic antibody is detected with a detecting agent.

26. The method of claim 25, wherein the detecting agent is an FcεRIα polypeptide that binds to an Fc region of a human IgE.

27. The method of claim 26, wherein the FcεRIα polypeptide comprises an extracellular domain of an FcεRIα subunit.

28. The method of claim 27, wherein the FcεRIα polypeptide comprises an extracellular domain of an FcεRIα subunit fused to an IgG constant region.

29. The method of claim 26, wherein the FcεRIα polypeptide is labeled.

30. The method of claim 29, wherein the label on the FcεRIα polypeptide is selected from the group consisting of biotin, digoxigenin, ruthenium, a radiologic label, a photoluminescent label, a chemiluminescent label, a fluorescent label, an electrochemiluminescent label, and an enzyme label.

31. The method of claim 29, wherein the label on the FcεRIα polypeptide is detected by a second detecting agent that specifically binds to the label on the FcεRIα polypeptide.

32. A method for detecting an anti-drug antibody of IgE isotype that may be present in a sample from a human patient, wherein variable regions of the anti-drug antibody specifically bind to a therapeutic anti-IgE antibody, comprising the steps of:
(a) contacting the sample that may contain the anti-drug antibody with (i) a mutant of the therapeutic antibody and (ii) an FcεRIα polypeptide that binds to an Fc region of a human IgE, wherein the mutant therapeutic antibody comprises one, two, three, four, five, or six amino acid mutations in complementarity determining region (CDR) sequences of a heavy or light chain of the therapeutic anti-IgE antibody, and wherein relative binding affinity of the mutant therapeutic antibody to an Fc region of human IgE is about 10% or less of relative binding affinity of the therapeutic anti-IgE antibody to said Fc region of human IgE; wherein the sample contains whole blood, serum or plasma from the human patient;
(b) capturing the contacted mutant therapeutic antibody to a surface; and
(c) detecting specific binding of the anti-drug antibody of IgE isotype in the sample to the mutant therapeutic antibody, wherein the detection of the specific binding indicates presence or level of the anti-drug antibody of IgE isotype in the patient.

33. The method of claim 32, wherein excess amount of FcεRIα polypeptide is contacted with the sample in step (a).

34. The method of claim 33, wherein at least about 10-fold excess of FcεRIα polypeptide is contacted with the sample in step (a).

35. The method of claim 32, wherein the FcεRIα polypeptide comprises an extracellular domain of an FcεRIα subunit.

36. The method of claim 32, wherein the mutant therapeutic antibody is labeled and is captured to the surface by a surface-immobilized capture agent that specifically binds to the label.

37. The method of claim 36, wherein the label is biotin and the surface is coated with streptavidin as the capture agent.

38. The method of claim 32, wherein the binding of the anti-drug antibody of the IgE isotype to the mutant therapeutic antibody is detected by a labeled anti-human IgE antibody.

39. The method of claim 32, wherein the FcεRIα polypeptide is labeled and the binding of the anti-drug antibody of the IgE isotype to the mutant therapeutic antibody is detected by a detecting agent that specifically binds to the label on the FcεRIα polypeptide.

40. The method of claim 1, 17, or 32, wherein the mutant therapeutic antibody comprises one, two, three, four, five, or six amino acid mutations in the CDR sequences of the heavy and light chain of the therapeutic anti-IgE antibody.

* * * * *

SEQUENCE LISTING

<160> NUMBER OF SEQ ID NOS: 31

<210> SEQ ID NO 1
<211> LENGTH: 216
<212> TYPE: PRT
<213> ORGANISM: Artificial Sequence
<220> FEATURE:
<223> OTHER INFORMATION: Synthetic construct

<400> SEQUENCE: 1

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 2
<211> LENGTH: 451
<212> TYPE: PRT
<213> ORGANISM: Artificial Sequence
<220> FEATURE:
<223> OTHER INFORMATION: Synthetic construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

```
Leu Gln Met Asn Ser Leu Arg Ala Glu Asp Thr Ala Val Tyr Tyr Cys
                 85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 3
<211> LENGTH: 232
<212> TYPE: PRT
<213> ORGANISM: Cynomolgus macaque

<400> SEQUENCE: 3
```

```
Val Pro Gln Lys Pro Thr Val Ser Leu Asn Pro Pro Trp Asn Arg Ile
1               5                   10                  15

Phe Lys Gly Glu Asn Val Thr Leu Thr Cys Asn Gly Ser Asn Phe Phe
            20                  25                  30

Glu Val Ser Ser Met Lys Trp Phe His Asn Gly Ser Leu Ser Glu Val
        35                  40                  45

Ala Asn Ser Ser Leu Asn Ile Val Asn Ala Asp Phe Glu Asp Ser Gly
50                  55                  60

Glu Tyr Lys Cys Gln His Gln Gln Phe Asp Asp Ser Glu Pro Val His
65              70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Ser Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Thr Thr Val Glu
130                 135                 140

Asp Ser Gly Thr Tyr Tyr Cys Thr Gly Lys Leu Trp Gln Leu Asp Cys
145                 150                 155                 160

Glu Ser Glu Pro Leu Asn Ile Thr Val Ile Lys Ala Gln His Asp Lys
                165                 170                 175

Tyr Trp Leu Gln Phe Leu Ile Pro Leu Leu Val Ala Ile Leu Phe Ala
            180                 185                 190

Val Asp Thr Gly Leu Phe Ile Ser Thr Gln Gln Gln Val Thr Phe Leu
            195                 200                 205

Leu Lys Ile Lys Arg Thr Arg Lys Gly Phe Lys Leu Leu Asn Pro His
210                 215                 220

Pro Lys Pro Asn Pro Lys Ser Asn
225                 230

<210> SEQ ID NO 4
<211> LENGTH: 232
<212> TYPE: PRT
<213> ORGANISM: Macaca mulatta

<400> SEQUENCE: 4

Val Pro Gln Lys Pro Thr Val Ser Leu Asn Pro Pro Trp Asn Arg Ile
1               5                   10                  15

Phe Lys Gly Glu Asn Val Thr Leu Thr Cys Asn Gly Ser Asn Phe Phe
            20                  25                  30

Glu Val Ser Ser Met Lys Trp Phe His Asn Gly Ser Leu Ser Glu Val
        35                  40                  45

Ala Asn Ser Ser Leu Asn Ile Val Asn Ala Asp Phe Glu Asp Ser Gly
50                  55                  60

Glu Tyr Lys Cys Gln His Gln Gln Phe Asp Asp Ser Glu Pro Val His
65              70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Ser Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
```

```
                130             135             140
Asp Ser Gly Thr Tyr Tyr Cys Thr Gly Lys Leu Trp Gln Leu Asp Cys
145                 150                 155                 160

Glu Ser Glu Pro Leu Asn Ile Thr Val Ile Lys Ala Gln His Asp Lys
                165                 170                 175

Tyr Trp Leu Gln Phe Leu Ile Pro Leu Leu Val Ala Ile Leu Phe Ala
                180                 185                 190

Val Asp Thr Gly Leu Phe Ile Ser Thr Gln Gln Val Thr Phe Leu
                195                 200                 205

Leu Lys Ile Lys Arg Thr Arg Lys Gly Phe Lys Leu Leu Asn Pro His
                210                 215                 220

Pro Lys Pro Asn Pro Lys Ser Asn
225                 230

<210> SEQ ID NO 5
<211> LENGTH: 232
<212> TYPE: PRT
<213> ORGANISM: Pan troglodytes

<400> SEQUENCE: 5

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
                35                  40                  45

Thr Asn Ser Ser Leu Asn Ile Val Asn Ala Lys Phe Glu Asp Ser Gly
                50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
                115                 120                 125

Tyr Trp Tyr Glu Asn His Asn Ile Ser Ile Thr Asn Ala Thr Val Glu
                130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Phe Phe Ile Pro Leu Leu Val Ala Ile Leu Phe Ala
                180                 185                 190

Val Asp Thr Gly Leu Phe Ile Ser Thr Gln Gln Val Thr Phe Leu
                195                 200                 205

Leu Lys Ile Lys Arg Thr Arg Lys Gly Phe Arg Leu Leu Thr Pro His
                210                 215                 220

Pro Lys Pro Asn Pro Lys Asn Asn
225                 230

<210> SEQ ID NO 6
<211> LENGTH: 232
<212> TYPE: PRT
<213> ORGANISM: Homo sapiens
```

```
<400> SEQUENCE: 6

Val Pro Gln Lys Pro Lys Val Ser Leu Asn Pro Pro Trp Asn Arg Ile
 1               5                  10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Phe Phe Ile Pro Leu Leu Val Val Ile Leu Phe Ala
                180                 185                 190

Val Asp Thr Gly Leu Phe Ile Ser Thr Gln Gln Gln Val Thr Phe Leu
            195                 200                 205

Leu Lys Ile Lys Arg Thr Arg Lys Gly Phe Arg Leu Leu Asn Pro His
        210                 215                 220

Pro Lys Pro Asn Pro Lys Asn Asn
225                 230

<210> SEQ ID NO 7
<211> LENGTH: 122
<212> TYPE: PRT
<213> ORGANISM: Murine

<400> SEQUENCE: 7

Gln Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Ser His
                20                  25                  30

Trp Ile Glu Trp Val Lys Gln Arg Ser Gly His Gly Leu Glu Trp Ile
            35                  40                  45

Gly Glu Ile Leu Pro Gly Ser Gly Ser Ile Asn Tyr Asn Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Ala Ser Glu Asp Ser Ala Val Tyr Tyr Cys
                85                  90                  95

Gly Arg Glu Gly Ala Asp Tyr Gly Tyr Asp Val Ala Met Asp Tyr Trp
                100                 105                 110

Gly Gln Gly Ala Ser Val Thr Val Ser Ser
            115                 120
```

<210> SEQ ID NO 8
<211> LENGTH: 107
<212> TYPE: PRT
<213> ORGANISM: Murine

<400> SEQUENCE: 8

Gln Ile Val Ile Thr Gln Ser Pro Ala Ile Met Ser Ala Ser Pro Gly
1               5                   10                  15

Glu Lys Val Thr Ile Thr Cys Ser Ala Thr Ser Ser Val Asn Tyr Met
            20                  25                  30

His Trp Phe Gln Gln Lys Pro Gly Thr Ser Pro Lys Leu Trp Ile Tyr
        35                  40                  45

Gly Thr Ser His Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Arg Tyr Pro Phe Thr
                85                  90                  95

Phe Gly Ser Gly Thr Lys Leu Glu Ile Lys Arg
            100                 105

<210> SEQ ID NO 9
<211> LENGTH: 366
<212> TYPE: DNA
<213> ORGANISM: Murine

<400> SEQUENCE: 9
caagttcaac tgcagcagtc tggcgctgag ctgatgaagc tggggcctc agtgaagata      60 tcctgcaagg ctactggcta cacattcagt agccactgga tagagtgggt gaaacagagg    120
tctggacatg gccttgagtg gattggagag attctacctg gaagtggtag tattaattac    180
aatgagaagt tcaagggcaa ggccacattc acagcagaca catcctccaa cacagcctac    240
atgcaactca gcagcctggc atctgaggac tctgccgtct attattgtgg aagagagggg    300
gccgactatg gttacgacgt tgctatggac tactggggtc aaggagcctc ggtcaccgtc    360
tcctcg                                                               366

<210> SEQ ID NO 10
<211> LENGTH: 321
<212> TYPE: DNA
<213> ORGANISM: Murine

<400> SEQUENCE: 10
caaattgtta tcacccagtc tccagcaatc atgtctgcat ctccagggga gaaggtcacc      60
ataacctgta gtgccaccte aagtgtaaat tacatgcact ggttccagca gaagccaggc    120
acttctccca aactctggat ttatggcaca tcccacctgg cttctggagt ccctgctcgc    180
ttcagtggca gtggatctgg gacctcttac tctctcacaa tcagccgaat ggaggctgaa    240
gatgctgcca cttattactg ccagcaaagg agtcgttacc cattcacgtt cggctcgggg    300
acaaagctcg agatcaaacg g                                              321

<210> SEQ ID NO 11
<211> LENGTH: 236
<212> TYPE: PRT
<213> ORGANISM: Artificial Sequence
<220> FEATURE:
<223> OTHER INFORMATION: Synthetic construct

<400> SEQUENCE: 11

```
Met Gly Gly Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Leu Asp Gln Leu Leu Glu Val Pro Gln Lys Pro Thr Val Ser Leu
50                  55                  60

Asn Pro Pro Trp Asn Arg Ile Phe Lys Gly Glu Asn Val Thr Leu Thr
65                  70                  75                  80

Cys Asn Gly Ser Asn Phe Phe Glu Val Ser Ser Met Lys Trp Phe His
                85                  90                  95

Asn Gly Ser Leu Ser Glu Val Ala Asn Ser Ser Leu Asn Ile Val Asn
            100                 105                 110

Ala Asp Phe Glu Asp Ser Gly Glu Tyr Lys Cys Gln His Gln Gln Phe
        115                 120                 125

Asp Asp Ser Glu Pro Val His Leu Glu Val Phe Ser Asp Trp Leu Leu
130                 135                 140

Leu Gln Ala Ser Ala Glu Val Val Met Glu Gly Gln Pro Leu Phe Leu
145                 150                 155                 160

Arg Cys His Ser Trp Arg Asn Trp Asp Val Tyr Lys Val Ile Tyr Tyr
                165                 170                 175

Lys Asp Gly Glu Ala Leu Lys Tyr Trp Tyr Glu Asn His Asn Ile Ser
            180                 185                 190

Ile Thr Asn Thr Thr Val Asp Ser Gly Thr Tyr Tyr Cys Thr Gly Lys
        195                 200                 205

Leu Trp Gln Leu Asp Tyr Glu Ser Glu Pro Leu Asn Ile Thr Val Ile
210                 215                 220

Lys Ala Gln His Asp Lys His His His His His His
225                 230                 235
```

<210> SEQ ID NO 12
<211> LENGTH: 207
<212> TYPE: PRT
<213> ORGANISM: Artificial Sequence
<220> FEATURE:
<223> OTHER INFORMATION: Synthetic construct

<400> SEQUENCE: 12

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
        50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
```

```
            115                 120                 125
Phe Leu Arg Cys His Ser Trp Arg Asn Trp Asp Val Tyr Lys Val Ile
        130                 135                 140

Tyr Tyr Lys Asp Gly Glu Ala Leu Lys Tyr Trp Glu Asn His Asn
145                 150                 155                 160

Ile Ser Ile Thr Asn Thr Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
        180                 185                 190

Thr Val Ile Lys Ala Gln His Asp Lys His His His His His His
        195                 200                 205
```

<210> SEQ ID NO 13
<211> LENGTH: 207
<212> TYPE: PRT
<213> ORGANISM: Artificial Sequence
<220> FEATURE:
<223> OTHER INFORMATION: Synthetic construct

<400> SEQUENCE: 13

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
    50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
        130                 135                 140

Tyr Tyr Lys Asp Gly Glu Ala Leu Lys Tyr Trp Glu Asn His Asn
145                 150                 155                 160

Ile Ser Ile Thr Asn Thr Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
        180                 185                 190

Thr Val Ile Lys Ala Gln His Asp Lys His His His His His His
        195                 200                 205
```

<210> SEQ ID NO 14
<211> LENGTH: 55
<212> TYPE: PRT
<213> ORGANISM: Artificial Sequence
<220> FEATURE:
<223> OTHER INFORMATION: Synthetic construct

<400> SEQUENCE: 14

```
Met Gly Gly Ala Ala Ala Arg Leu Gly Ala Val Ile Leu Phe Val Val
1               5                   10                  15
```

```
Ile Val Gly Leu His Gly Val Arg Gly Lys Tyr Ala Leu Ala Asp Ala
         20                  25                  30

Ser Leu Lys Met Ala Asp Pro Asn Arg Phe Arg Gly Lys Asp Leu Pro
         35                  40                  45

Val Leu Asp Gln Leu Leu Glu
         50              55
```

<210> SEQ ID NO 15
<211> LENGTH: 237
<212> TYPE: PRT
<213> ORGANISM: Artificial Sequence
<220> FEATURE:
<223> OTHER INFORMATION: Synthetic construct

<400> SEQUENCE: 15

```
Met Gly Gly Ala Ala Ala Arg Leu Gly Ala Val Ile Leu Phe Val Val
 1               5                  10                  15

Ile Val Gly Leu His Gly Val Arg Gly Lys Tyr Ala Leu Ala Asp Ala
         20                  25                  30

Ser Leu Lys Met Ala Asp Pro Asn Arg Phe Arg Gly Lys Asp Leu Pro
         35                  40                  45

Val Leu Asp Gln Leu Leu Glu Val Pro Gln Lys Pro Thr Val Ser Leu
         50              55                  60

Asn Pro Pro Trp Asn Arg Ile Phe Lys Gly Glu Asn Val Thr Leu Thr
 65              70                  75                  80

Cys Asn Gly Ser Asn Phe Phe Glu Val Ser Ser Met Lys Trp Phe His
                 85                  90                  95

Asn Gly Ser Leu Ser Glu Val Ala Ser Ser Leu Asn Ile Val Asn
             100                 105                 110

Ala Asp Phe Glu Asp Ser Gly Glu Tyr Lys Cys Gln His Gln Gln Phe
         115                 120                 125

Asp Asp Ser Glu Pro Val His Leu Glu Val Phe Ser Asp Trp Leu Leu
     130                 135                 140

Leu Gln Ala Ser Ala Glu Val Val Met Glu Gly Gln Pro Leu Phe Leu
145                 150                 155                 160

Arg Cys His Ser Trp Arg Asn Trp Asp Val Tyr Lys Val Ile Tyr Tyr
                 165                 170                 175

Lys Asp Gly Glu Ala Leu Lys Tyr Trp Tyr Glu Asn His Asn Ile Ser
             180                 185                 190

Ile Thr Asn Thr Thr Val Glu Asp Ser Gly Thr Tyr Tyr Cys Thr Gly
         195                 200                 205

Lys Leu Trp Gln Leu Asp Cys Glu Ser Glu Pro Leu Asn Ile Thr Val
     210                 215                 220

Ile Lys Ala Gln His Asp Lys His His His His His His
225                 230                 235
```

<210> SEQ ID NO 16
<211> LENGTH: 293
<212> TYPE: PRT
<213> ORGANISM: Artificial Sequence
<220> FEATURE:
<223> OTHER INFORMATION: Synthetic construct

<400> SEQUENCE: 16

```
Met Gly Gly Ala Ala Ala Arg Leu Gly Ala Val Ile Leu Phe Val Val
 1               5                  10                  15

Ile Val Gly Leu His Gly Val Arg Gly Lys Tyr Ala Leu Ala Asp Ala
         20                  25                  30
```

```
Ser Leu Lys Met Ala Asp Pro Asn Arg Phe Arg Gly Lys Asp Leu Pro
        35                  40                  45

Val Leu Asp Gln Leu Leu Glu Val Pro Gln Lys Pro Thr Val Ser Leu
 50                  55                  60

Asn Pro Pro Trp Asn Arg Ile Phe Lys Gly Glu Asn Val Thr Leu Thr
 65                  70                  75                  80

Cys Asn Gly Ser Asn Phe Phe Glu Val Ser Ser Met Lys Trp Phe His
                 85                  90                  95

Asn Gly Ser Leu Ser Glu Val Ala Asn Ser Ser Leu Asn Ile Val Asn
            100                 105                 110

Ala Asp Phe Glu Asp Ser Gly Tyr Lys Cys Gln His Gln Gln Phe
            115                 120                 125

Asp Asp Ser Glu Pro Val His Leu Glu Val Phe Ser Asp Trp Leu Leu
130                 135                 140

Leu Gln Ala Ser Ala Glu Val Val Met Glu Gly Gln Pro Leu Phe Leu
145                 150                 155                 160

Arg Cys His Ser Trp Arg Asn Trp Asp Val Tyr Lys Val Ile Tyr Tyr
                165                 170                 175

Lys Asp Gly Glu Ala Leu Lys Tyr Trp Tyr Glu Asn His Asn Ile Ser
            180                 185                 190

Ile Thr Asn Ala Thr Val Glu Asp Ser Gly Thr Tyr Tyr Cys Thr Gly
        195                 200                 205

Lys Leu Trp Gln Leu Asp Cys Glu Ser Glu Pro Leu Asn Ile Thr Val
        210                 215                 220

Ile Lys Ala Gln His Asp Lys Tyr Trp Leu Gln Phe Leu Ile Pro Leu
225                 230                 235                 240

Leu Val Ala Ile Leu Phe Ala Val Asp Thr Gly Leu Phe Ile Ser Thr
                245                 250                 255

Gln Gln Gln Val Thr Phe Leu Leu Lys Ile Lys Arg Thr Arg Lys Gly
            260                 265                 270

Phe Lys Leu Leu Asn Pro His Pro Lys Pro Asn Pro Lys Ser Asn His
        275                 280                 285

His His His His His
        290

<210> SEQ ID NO 17
<211> LENGTH: 293
<212> TYPE: PRT
<213> ORGANISM: Artificial Sequence
<220> FEATURE:
<223> OTHER INFORMATION: Synthetic construct

<400> SEQUENCE: 17

Met Gly Gly Ala Ala Ala Arg Leu Gly Ala Val Ile Leu Phe Val Val
 1               5                  10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Gln Lys Pro Lys Val Ser Leu
 50                  55                  60

Asn Pro Pro Trp Asn Arg Ile Phe Lys Gly Glu Asn Val Thr Leu Thr
 65                  70                  75                  80

Cys Asn Gly Asn Asn Phe Phe Glu Val Ser Ser Thr Lys Trp Phe His
                 85                  90                  95
```

```
Asn Gly Ser Leu Ser Glu Glu Thr Asn Ser Ser Leu Asn Ile Val Asn
            100                 105                 110

Ala Lys Phe Glu Asp Ser Gly Glu Tyr Lys Cys Gln His Gln Gln Val
        115                 120                 125

Asn Glu Ser Glu Pro Val Tyr Leu Glu Val Phe Ser Asp Trp Leu Leu
    130                 135                 140

Leu Gln Ala Ser Ala Glu Val Val Met Glu Gly Gln Pro Leu Phe Leu
145                 150                 155                 160

Arg Cys His Gly Trp Arg Asn Trp Asp Val Tyr Lys Val Ile Tyr Tyr
                165                 170                 175

Lys Asp Gly Glu Ala Leu Lys Tyr Trp Tyr Glu Asn His Asn Ile Ser
            180                 185                 190

Ile Thr Asn Ala Thr Val Glu Asp Ser Gly Thr Tyr Tyr Cys Thr Gly
        195                 200                 205

Lys Val Trp Gln Leu Asp Tyr Glu Ser Glu Pro Leu Asn Ile Thr Val
    210                 215                 220

Ile Lys Ala Pro Arg Glu Lys Tyr Trp Leu Gln Phe Phe Ile Pro Leu
225                 230                 235                 240

Leu Val Ala Ile Leu Phe Ala Val Asp Thr Gly Leu Phe Ile Ser Thr
                245                 250                 255

Gln Gln Gln Val Thr Phe Leu Leu Lys Ile Lys Arg Thr Arg Lys Gly
            260                 265                 270

Phe Arg Leu Leu Thr Pro His Pro Lys Pro Asn Pro Lys Asn Asn His
        275                 280                 285

His His His His His
    290

<210> SEQ ID NO 18
<211> LENGTH: 406
<212> TYPE: PRT
<213> ORGANISM: Artificial Sequence
<220> FEATURE:
<223> OTHER INFORMATION: Synthetic construct

<400> SEQUENCE: 18

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Leu Trp Gln Leu Asp Tyr
145                 150                 155                 160
```

```
Glu Ser Glu Pro Leu Asn Ile Thr Val Ile Lys Ala Pro Arg Glu Lys
                165                 170                 175
Tyr Trp Leu Asp Lys Thr His Thr Cys Pro Pro Cys Pro Ala Pro Glu
            180                 185                 190
Leu Leu Gly Gly Pro Ser Val Phe Leu Phe Pro Pro Lys Pro Lys Asp
        195                 200                 205
Thr Leu Met Ile Ser Arg Thr Pro Glu Val Thr Cys Val Val Val Asp
    210                 215                 220
Val Ser His Glu Asp Pro Glu Val Lys Phe Asn Trp Tyr Val Asp Gly
225                 230                 235                 240
Val Glu Val His Asn Ala Lys Thr Lys Pro Arg Glu Glu Gln Tyr Asn
                245                 250                 255
Ser Thr Tyr Arg Val Val Ser Val Leu Thr Val Leu His Gln Asp Trp
            260                 265                 270
Leu Asn Gly Lys Glu Tyr Lys Cys Lys Val Ser Asn Lys Ala Leu Pro
        275                 280                 285
Ala Pro Ile Glu Lys Thr Ile Ser Lys Ala Lys Gly Gln Pro Arg Glu
    290                 295                 300
Pro Gln Val Tyr Thr Leu Pro Pro Ser Arg Glu Glu Met Thr Lys Asn
305                 310                 315                 320
Gln Val Ser Leu Thr Cys Leu Val Lys Gly Phe Tyr Pro Ser Asp Ile
                325                 330                 335
Ala Val Glu Trp Glu Ser Asn Gly Gln Pro Glu Asn Asn Tyr Lys Thr
            340                 345                 350
Thr Pro Pro Val Leu Asp Ser Asp Gly Ser Phe Phe Leu Tyr Ser Lys
        355                 360                 365
Leu Thr Val Asp Lys Ser Arg Trp Gln Gln Gly Asn Val Phe Ser Cys
    370                 375                 380
Ser Val Met His Glu Ala Leu His Asn His Tyr Thr Gln Lys Ser Leu
385                 390                 395                 400
Ser Leu Ser Pro Gly Lys
            405

<210> SEQ ID NO 19
<211> LENGTH: 229
<212> TYPE: PRT
<213> ORGANISM: Artificial Sequence
<220> FEATURE:
<223> OTHER INFORMATION: Synthetic construct
<220> FEATURE:
<223> OTHER INFORMATION: Fc domain of IgG

<400> SEQUENCE: 19

Val Thr Asp Lys Thr His Thr Cys Pro Pro Cys Pro Ala Pro Glu Leu
  1               5                  10                  15
Leu Gly Gly Pro Ser Val Phe Leu Phe Pro Pro Lys Pro Lys Asp Thr
                 20                  25                  30
Leu Met Ile Ser Arg Thr Pro Glu Val Thr Cys Val Val Val Asp Val
             35                  40                  45
Ser His Glu Asp Pro Glu Val Lys Phe Asn Trp Tyr Val Asp Gly Val
         50                  55                  60
Glu Val His Asn Ala Lys Thr Lys Pro Arg Glu Glu Gln Tyr Asn Ser
 65                  70                  75                  80
Thr Tyr Arg Val Val Ser Val Leu Thr Val Leu His Gln Asp Trp Leu
                 85                  90                  95
```

```
Asn Gly Lys Glu Tyr Lys Cys Lys Val Ser Asn Lys Ala Leu Pro Ala
             100                 105                 110

Pro Ile Glu Lys Thr Ile Ser Lys Ala Lys Gly Gln Pro Arg Glu Pro
         115                 120                 125

Gln Val Tyr Thr Leu Pro Pro Ser Arg Glu Glu Met Thr Lys Asn Gln
     130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 20
<211> LENGTH: 425
<212> TYPE: PRT
<213> ORGANISM: Artificial Sequence
<220> FEATURE:
<223> OTHER INFORMATION: Synthetic construct

<400> SEQUENCE: 20

Met Ala Pro Ala Met Glu Ser Pro Thr Leu Leu Cys Val Ala Leu Leu
 1               5                  10                  15

Phe Phe Ala Pro Asp Gly Val Leu Ala Val Pro Gln Lys Pro Thr Val
             20                  25                  30

Ser Leu Asn Pro Pro Trp Asn Arg Ile Phe Lys Gly Glu Asn Val Thr
         35                  40                  45

Leu Thr Cys Asn Gly Ser Asn Phe Phe Glu Val Ser Ser Met Lys Trp
     50                  55                  60

Phe His Asn Gly Ser Leu Ser Glu Val Ala Asn Ser Ser Leu Asn Ile
 65                  70                  75                  80

Val Asn Ala Asp Phe Glu Asp Ser Gly Glu Tyr Lys Cys Gln His Gln
                 85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
            180                 185                 190

Thr Val Ile Lys Val Thr Asp Lys Thr His Thr Cys Pro Pro Cys Pro
        195                 200                 205

Ala Pro Glu Leu Leu Gly Gly Pro Ser Val Phe Leu Phe Pro Pro Lys
    210                 215                 220
```

```
Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
                420                 425

<210> SEQ ID NO 21
<211> LENGTH: 426
<212> TYPE: PRT
<213> ORGANISM: Artificial Sequence
<220> FEATURE:
<223> OTHER INFORMATION: Synthetic construct

<400> SEQUENCE: 21

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
        50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160
```

Ile Ser Ile Thr Asn Ala Thr Val Glu Asp Ser Gly Thr Tyr Tyr Cys
            165                 170                 175

Thr Gly Lys Leu Trp Gln Leu Asp Tyr Glu Ser Glu Pro Leu Asn Ile
            180                 185                 190

Thr Val Ile Lys Ala Val Thr Asp Lys Thr His Thr Cys Pro Pro Cys
            195                 200                 205

Pro Ala Pro Glu Leu Leu Gly Gly Pro Ser Val Phe Leu Phe Pro Pro
            210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                    245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
            275                 280                 285

His Gln Asp Trp Leu Asn Gly Lys Glu Tyr Lys Cys Lys Val Ser Asn
            290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Glu Glu
                    325                 330                 335

Met Thr Lys Asn Gln Val Ser Leu Thr Cys Leu Val Lys Gly Phe Tyr
            340                 345                 350

Pro Ser Asp Ile Ala Val Glu Trp Glu Ser Asn Gly Gln Pro Glu Asn
            355                 360                 365

Asn Tyr Lys Thr Thr Pro Pro Val Leu Asp Ser Asp Gly Ser Phe Phe
            370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                    405                 410                 415

Gln Lys Ser Leu Ser Leu Ser Pro Gly Lys
            420                 425

<210> SEQ ID NO 22
<211> LENGTH: 427
<212> TYPE: PRT
<213> ORGANISM: Artificial Sequence
<220> FEATURE:
<223> OTHER INFORMATION: Synthetic construct

<400> SEQUENCE: 22

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
            20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
            50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                    85                  90                  95

```
Gln Phe Asp Asp Ser Glu Pro Val His Leu Glu Val Phe Ser Asp Trp
                100                 105                 110
Leu Leu Leu Gln Ala Ser Ala Glu Val Val Met Glu Gly Gln Pro Leu
            115                 120                 125
Phe Leu Arg Cys His Ser Trp Arg Asn Trp Asp Val Tyr Lys Val Ile
        130                 135                 140
Tyr Tyr Lys Asp Gly Glu Ala Leu Lys Tyr Trp Tyr Glu Asn His Asn
145                 150                 155                 160
Ile Ser Ile Thr Asn Ala Thr Val Glu Asp Ser Gly Thr Tyr Tyr Cys
                165                 170                 175
Thr Gly Lys Leu Trp Gln Leu Asp Tyr Glu Ser Glu Pro Leu Asn Ile
            180                 185                 190
Thr Val Ile Lys Ala Gln Val Thr Asp Lys Thr His Thr Cys Pro Pro
        195                 200                 205
Cys Pro Ala Pro Glu Leu Leu Gly Gly Pro Ser Val Phe Leu Phe Pro
210                 215                 220
Pro Lys Pro Lys Asp Thr Leu Met Ile Ser Arg Thr Pro Glu Val Thr
225                 230                 235                 240
Cys Val Val Val Asp Val Ser His Glu Asp Pro Glu Val Lys Phe Asn
                245                 250                 255
Trp Tyr Val Asp Gly Val Glu Val His Asn Ala Lys Thr Lys Pro Arg
            260                 265                 270
Glu Glu Gln Tyr Asn Ser Thr Tyr Arg Val Val Ser Val Leu Thr Val
        275                 280                 285
Leu His Gln Asp Trp Leu Asn Gly Lys Glu Tyr Lys Cys Lys Val Ser
290                 295                 300
Asn Lys Ala Leu Pro Ala Pro Ile Glu Lys Thr Ile Ser Lys Ala Lys
305                 310                 315                 320
Gly Gln Pro Arg Glu Pro Gln Val Tyr Thr Leu Pro Pro Ser Arg Glu
                325                 330                 335
Glu Met Thr Lys Asn Gln Val Ser Leu Thr Cys Leu Val Lys Gly Phe
            340                 345                 350
Tyr Pro Ser Asp Ile Ala Val Glu Trp Glu Ser Asn Gly Gln Pro Glu
        355                 360                 365
Asn Asn Tyr Lys Thr Thr Pro Pro Val Leu Asp Ser Asp Gly Ser Phe
370                 375                 380
Phe Leu Tyr Ser Lys Leu Thr Val Asp Lys Ser Arg Trp Gln Gln Gly
385                 390                 395                 400
Asn Val Phe Ser Cys Ser Val Met His Glu Ala Leu His Asn His Tyr
                405                 410                 415
Thr Gln Lys Ser Leu Ser Leu Ser Pro Gly Lys
            420                 425

<210> SEQ ID NO 23
<211> LENGTH: 428
<212> TYPE: PRT
<213> ORGANISM: Artificial Sequence
<220> FEATURE:
<223> OTHER INFORMATION: Synthetic construct

<400> SEQUENCE: 23

Met Ala Pro Ala Met Glu Ser Pro Thr Leu Leu Cys Val Ala Leu Leu
1               5                   10                  15
Phe Phe Ala Pro Asp Gly Val Leu Ala Val Pro Gln Lys Pro Thr Val
                20                  25                  30
```

```
Ser Leu Asn Pro Pro Trp Asn Arg Ile Phe Lys Gly Glu Asn Val Thr
            35                  40                  45
Leu Thr Cys Asn Gly Ser Asn Phe Phe Glu Val Ser Ser Met Lys Trp
 50                  55                  60
Phe His Asn Gly Ser Leu Ser Glu Val Ala Asn Ser Ser Leu Asn Ile
 65                  70                  75                  80
Val Asn Ala Asp Phe Glu Asp Ser Gly Glu Tyr Lys Cys Gln His Gln
                 85                  90                  95
Gln Phe Asp Asp Ser Glu Pro Val His Leu Glu Val Phe Ser Asp Trp
            100                 105                 110
Leu Leu Leu Gln Ala Ser Ala Glu Val Val Met Glu Gly Gln Pro Leu
            115                 120                 125
Phe Leu Arg Cys His Ser Trp Arg Asn Trp Asp Val Tyr Lys Val Ile
            130                 135                 140
Tyr Tyr Lys Asp Gly Glu Ala Leu Lys Tyr Trp Tyr Glu Asn His Asn
145                 150                 155                 160
Ile Ser Ile Thr Asn Ala Thr Val Glu Asp Ser Gly Thr Tyr Tyr Cys
                165                 170                 175
Thr Gly Lys Leu Trp Gln Leu Asp Tyr Glu Ser Glu Pro Leu Asn Ile
            180                 185                 190
Thr Val Ile Lys Ala Gln His Val Thr Asp Lys Thr His Thr Cys Pro
            195                 200                 205
Pro Cys Pro Ala Pro Glu Leu Leu Gly Gly Pro Ser Val Phe Leu Phe
            210                 215                 220
Pro Pro Lys Pro Lys Asp Thr Leu Met Ile Ser Arg Thr Pro Glu Val
225                 230                 235                 240
Thr Cys Val Val Val Asp Val Ser His Glu Asp Pro Glu Val Lys Phe
                245                 250                 255
Asn Trp Tyr Val Asp Gly Val Glu Val His Asn Ala Lys Thr Lys Pro
            260                 265                 270
Arg Glu Glu Gln Tyr Asn Ser Thr Tyr Arg Val Val Ser Val Leu Thr
            275                 280                 285
Val Leu His Gln Asp Trp Leu Asn Gly Lys Glu Tyr Lys Cys Lys Val
            290                 295                 300
Ser Asn Lys Ala Leu Pro Ala Pro Ile Glu Lys Thr Ile Ser Lys Ala
305                 310                 315                 320
Lys Gly Gln Pro Arg Glu Pro Gln Val Tyr Thr Leu Pro Pro Ser Arg
                325                 330                 335
Glu Glu Met Thr Lys Asn Gln Val Ser Leu Thr Cys Leu Val Lys Gly
            340                 345                 350
Phe Tyr Pro Ser Asp Ile Ala Val Glu Trp Glu Ser Asn Gly Gln Pro
            355                 360                 365
Glu Asn Asn Tyr Lys Thr Thr Pro Pro Val Leu Asp Ser Asp Gly Ser
370                 375                 380
Phe Phe Leu Tyr Ser Lys Leu Thr Val Asp Lys Ser Arg Trp Gln Gln
385                 390                 395                 400
Gly Asn Val Phe Ser Cys Ser Val Met His Glu Ala Leu His Asn His
                405                 410                 415
Tyr Thr Gln Lys Ser Leu Ser Leu Ser Pro Gly Lys
            420                 425

<210> SEQ ID NO 24
<211> LENGTH: 429
<212> TYPE: PRT
```

<213> ORGANISM: Artificial Sequence
<220> FEATURE:
<223> OTHER INFORMATION: Synthetic construct

<400> SEQUENCE: 24

```
Met Ala Pro Ala Met Glu Ser Pro Thr Leu Leu Cys Val Ala Leu Leu
 1               5                  10                  15

Phe Phe Ala Pro Asp Gly Val Leu Ala Val Pro Gln Lys Pro Thr Val
            20                  25                  30

Ser Leu Asn Pro Pro Trp Asn Arg Ile Phe Lys Gly Glu Asn Val Thr
        35                  40                  45

Leu Thr Cys Asn Gly Ser Asn Phe Phe Glu Val Ser Ser Met Lys Trp
    50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
            180                 185                 190

Thr Val Ile Lys Ala Gln His Asp Val Thr Asp Lys Thr His Thr Cys
        195                 200                 205

Pro Pro Cys Pro Ala Pro Glu Leu Leu Gly Gly Pro Ser Val Phe Leu
    210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Lys
                245                 250                 255

Phe Asn Trp Tyr Val Asp Gly Val Glu Val His Asn Ala Lys Thr Lys
            260                 265                 270

Pro Arg Glu Glu Gln Tyr Asn Ser Thr Tyr Arg Val Val Ser Val Leu
        275                 280                 285

Thr Val Leu His Gln Asp Trp Leu Asn Gly Lys Glu Tyr Lys Cys Lys
    290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
                325                 330                 335

Arg Glu Glu Met Thr Lys Asn Gln Val Ser Leu Thr Cys Leu Val Lys
            340                 345                 350

Gly Phe Tyr Pro Ser Asp Ile Ala Val Glu Trp Glu Ser Asn Gly Gln
        355                 360                 365

Pro Glu Asn Asn Tyr Lys Thr Thr Pro Pro Val Leu Asp Ser Asp Gly
    370                 375                 380

Ser Phe Phe Leu Tyr Ser Lys Leu Thr Val Asp Lys Ser Arg Trp Gln
```

```
                385                 390                 395                 400
        Gln Gly Asn Val Phe Ser Cys Ser Val Met His Glu Ala Leu His Asn
                        405                 410                 415

His Tyr Thr Gln Lys Ser Leu Ser Leu Ser Pro Gly Lys
                        420                 425

<210> SEQ ID NO 25
<211> LENGTH: 430
<212> TYPE: PRT
<213> ORGANISM: Artificial Sequence
<220> FEATURE:
<223> OTHER INFORMATION: Synthetic construct

<400> SEQUENCE: 25

Met Ala Pro Ala Met Glu Ser Pro Thr Leu Leu Cys Val Ala Leu Leu
 1               5                  10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
        50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
            180                 185                 190

Thr Val Ile Lys Ala Gln His Asp Lys Val Thr Asp Lys Thr His Thr
        195                 200                 205

Cys Pro Pro Cys Pro Ala Pro Glu Leu Leu Gly Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Lys Phe Asn Trp Tyr Val Asp Gly Val Glu Val His Asn Ala Lys Thr
            260                 265                 270

Lys Pro Arg Glu Glu Gln Tyr Asn Ser Thr Tyr Arg Val Val Ser Val
        275                 280                 285

Leu Thr Val Leu His Gln Asp Trp Leu Asn Gly Lys Glu Tyr Lys Cys
    290                 295                 300

Lys Val Ser Asn Lys Ala Leu Pro Ala Pro Ile Glu Lys Thr Ile Ser
305                 310                 315                 320

Lys Ala Lys Gly Gln Pro Arg Glu Pro Gln Val Tyr Thr Leu Pro Pro
```

325                 330                 335
Ser Arg Glu Glu Met Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
        355                 360                 365

Gln Pro Glu Asn Asn Tyr Lys Thr Thr Pro Pro Val Leu Asp Ser Asp
    370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
                405                 410                 415

Asn His Tyr Thr Gln Lys Ser Leu Ser Leu Ser Pro Gly Lys
            420                 425                 430

<210> SEQ ID NO 26
<211> LENGTH: 431
<212> TYPE: PRT
<213> ORGANISM: Artificial Sequence
<220> FEATURE:
<223> OTHER INFORMATION: Synthetic construct

<400> SEQUENCE: 26

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
        50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
            180                 185                 190

Thr Val Ile Lys Ala Gln His Asp Lys Tyr Val Thr Asp Lys Thr His
        195                 200                 205

Thr Cys Pro Pro Cys Pro Ala Pro Glu Leu Leu Gly Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys

```
                    260                 265                 270
Thr Lys Pro Arg Glu Gln Tyr Asn Ser Thr Tyr Arg Val Val Ser
            275                 280                 285

Val Leu Thr Val Leu His Gln Asp Trp Leu Asn Gly Lys Glu Tyr Lys
        290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Glu Glu Met Thr Lys Asn Gln Val Ser Leu Thr Cys Leu
                340                 345                 350

Val Lys Gly Phe Tyr Pro Ser Asp Ile Ala Val Glu Trp Glu Ser Asn
            355                 360                 365

Gly Gln Pro Glu Asn Asn Tyr Lys Thr Thr Pro Pro Val Leu Asp Ser
        370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
                420                 425                 430

<210> SEQ ID NO 27
<211> LENGTH: 432
<212> TYPE: PRT
<213> ORGANISM: Artificial Sequence
<220> FEATURE:
<223> OTHER INFORMATION: Synthetic construct

<400> SEQUENCE: 27

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
        50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
                100                 105                 110

Leu Leu Leu Gln Ala Ser Ala Glu Val Val Met Glu Gly Gln Pro Leu
        115                 120                 125

Phe Leu Arg Cys His Ser Trp Arg Asn Trp Asp Val Tyr Lys Val Ile
        130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Leu Trp Gln Leu Asp Tyr Glu Ser Glu Pro Leu Asn Ile
                180                 185                 190

Thr Val Ile Lys Ala Gln His Asp Lys Tyr Trp Val Thr Asp Lys Thr
```

```
                195                 200                 205
His Thr Cys Pro Pro Cys Pro Ala Pro Glu Leu Leu Gly Pro Ser
    210                 215                 220

Val Phe Leu Phe Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
            275                 280                 285

Ser Val Leu Thr Val Leu His Gln Asp Trp Leu Asn Gly Lys Glu Tyr
            290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Val Leu Asp
        370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 28
<211> LENGTH: 432
<212> TYPE: PRT
<213> ORGANISM: Artificial Sequence
<220> FEATURE:
<223> OTHER INFORMATION: Synthetic construct

<400> SEQUENCE: 28

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Thr Val
                20                  25                  30

Ser Leu Asn Pro Pro Trp Asn Arg Ile Phe Lys Gly Glu Asn Val Thr
            35                  40                  45

Leu Thr Cys Asn Gly Ser Asn Phe Phe Glu Val Ser Ser Met Lys Trp
        50                  55                  60

Phe His Asn Gly Ser Leu Ser Glu Val Ala Asn Ser Ser Leu Asn Ile
65                  70                  75                  80

Val Asn Ala Asp Phe Glu Asp Ser Gly Glu Tyr Lys Cys Gln His Gln
                85                  90                  95

Gln Phe Asp Asp Ser Glu Pro Val His Leu Glu Val Phe Ser Asp Trp
                100                 105                 110

Leu Leu Leu Gln Ala Ser Ala Glu Val Val Met Glu Gly Gln Pro Leu
            115                 120                 125

Phe Leu Arg Cys His Ser Trp Arg Asn Trp Asp Val Tyr Lys Val Ile
```

```
            130                 135                 140
Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Val Thr Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 29
<211> LENGTH: 428
<212> TYPE: PRT
<213> ORGANISM: Homo sapiens
    <220>
<221> NAME/KEY: misc_feature
<222> LOCATION: 160
<223> OTHER INFORMATION: x = any amino acid

<400> SEQUENCE: 29

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60
```

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
            85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
            115                 120                 125

Pro Thr Ile Gln Leu Leu Cys Leu Val Ser Gly Tyr Thr Pro Gly Thr
            130                 135                 140

Ile Asn Ile Thr Trp Leu Glu Asp Gly Gln Val Met Asp Val Asp Xaa
145                 150                 155                 160

Ser Thr Ala Ser Thr Thr Gln Glu Gly Glu Leu Ala Ser Thr Gln Ser
            165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
            195                 200                 205

Cys Ala Asp Ser Asn Pro Arg Gly Val Ser Ala Tyr Leu Ser Arg Pro
210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
            245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
            275                 280                 285

Arg Asp Trp Ile Glu Gly Glu Thr Tyr Gln Cys Arg Val Thr His Pro
290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
            325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
            370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
            405                 410                 415

Thr Val Gln Arg Ala Val Ser Val Asn Pro Gly Lys
            420                 425

<210> SEQ ID NO 30
<211> LENGTH: 106
<212> TYPE: PRT
<213> ORGANISM: Homo sapiens

<400> SEQUENCE: 30

Ala Asp Ala Ala Pro Thr Val Ser Ile Phe Pro Pro Ser Ser Glu Gln

```
                1               5              10              15

Leu Thr Ser Gly Gly Ala Ser Val Val Cys Phe Leu Asn Asn Phe Tyr
                20              25              30

Pro Lys Asp Ile Asn Val Lys Trp Lys Ile Asp Gly Ser Glu Arg Gln
            35              40              45

Asn Gly Val Leu Asn Ser Trp Thr Asp Gln Asp Ser Lys Asp Ser Thr
        50              55              60

Tyr Ser Met Ser Ser Thr Leu Thr Leu Thr Lys Asp Glu Tyr Glu Arg
65              70              75              80

His Asn Ser Tyr Thr Cys Glu Ala Thr His Lys Thr Ser Thr Ser Pro
                85              90              95

Ile Val Lys Ser Phe Asn Arg Asn Glu Cys
                100             105

<210> SEQ ID NO 31
<211> LENGTH: 7
<212> TYPE: PRT
<213> ORGANISM: Artificial Sequence
<220> FEATURE:
<223> OTHER INFORMATION: Synthetic construct

<400> SEQUENCE: 31

Ala Gln His Asp Lys Tyr Trp
1               5
```